US006821960B2

(12) United States Patent
Jørgensen et al.

(10) Patent No.: US 6,821,960 B2
(45) Date of Patent: Nov. 23, 2004

(54) GLUCAGON ANTAGONISTS/INVERSE AGONISTS

(75) Inventors: Anker Steen Jørgensen, København (DK); Peter Madsen, Bagsvaerd (DK)

(73) Assignee: Noyo Nordisk Pharmaceuticals, Inc., Princeton, NJ (US)

( * ) Notice: Subject to any disclaimer, the term of this patent is extended or adjusted under 35 U.S.C. 154(b) by 35 days.

(21) Appl. No.: 09/995,987

(22) Filed: Nov. 16, 2001

(65) Prior Publication Data

US 2003/0027849 A1 Feb. 6, 2003

Related U.S. Application Data

(60) Provisional application No. 60/252,322, filed on Nov. 20, 2000.

(30) Foreign Application Priority Data

Nov. 17, 2000 (DK) .................................. PA 2000 01733

(51) Int. Cl.$^7$ ........................ A61K 31/66; A61K 31/41; C07D 257/00; C07D 333/36; C07C 275/00
(52) U.S. Cl. ........................ 514/113; 514/364; 514/381; 514/417; 514/447; 514/563; 548/253; 548/473; 548/480; 549/69; 549/373; 562/439
(58) Field of Search ................................ 514/113, 364, 514/381, 417, 447, 563; 548/253, 473, 480; 549/69, 373; 562/439

(56) References Cited

U.S. PATENT DOCUMENTS

| 4,359,474 A | 11/1982 | Anderson et al. | 424/273 |
|---|---|---|---|
| 4,374,130 A | 2/1983 | Barcza | 424/184 |
| 5,776,954 A | 7/1998 | de Laszlo et al. | 514/340 |
| 5,837,719 A | 11/1998 | de Laszlo et al. | 514/343 |
| 5,880,139 A | 3/1999 | Chang | 514/326 |
| 6,297,269 B1 * | 10/2001 | Hulin et al. | 514/414 |

FOREIGN PATENT DOCUMENTS

| WO | WO 94/14426 | 7/1994 |
|---|---|---|
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/24780 | 6/1998 |
| WO | WO 98/24782 | 6/1998 |
| WO | WO 99/01423 | 1/1999 |
| WO | WO 99/24404 | 5/1999 |
| WO | WO 99/32448 | 7/1999 |
| WO | WO 00/39088 | 7/2000 |
| WO | WO 00/069810 | 11/2000 |

OTHER PUBLICATIONS

C.L. Brand et al., "Immunoneutralization of endogenous glucagons with Monoclonal glucagons antibody normalizes hyperglycaemia in moderately Streptozotocin–diabetic rats–"Diabetologia, vol. 37 pp. 985–993 (1994).
C.L. Brand et al., [535] Diabetes 43, [suppl 1], 172A (1994).
C.L. Brand et al., Am J. Physiol. 269, E469–E477 (1995).
C.L. Brand et al., [492] Diabetes 44 [suppl 1], 134A (1995).
C.L. Brand et al., "Evidence for a Major Role for Glucagon in Regulation of Plasma Glucose in Conscious, Nondiabetic, and Alloxan Induced Diabetic Rabbits", Diabetes vol. 45, pp. 1076–1083 (1996).
L.J. Jelinek et al., "Expression Cloning and Signaling Properties of the Rat Glucagon Receptor" Science vol. 259, pp. 1614–1616 (1993).
C.G. Unson et al., "Biological Activities of des–His$^1$[Glu$^9$]Glucagon Amide, A Glucagon Antagonist$^1$" Peptides, vol. 10 pp. 1171–1177(1998).
Post et al., "Mechanism of action of des–His$^1$[Glu$^9$ ]Glucagon Amide: A Peptide antagonist of the glucagons receptor system" Proc.Natl. Acad. Sci vol. 90., pp. 1662–1666 (1993).
Unson et al., "Multiple–site Replacement Analogs of Glucagon" The Journal of Biological Chemistry vol. 17, Issue of Apr. 29, pp. 12548–12551 (1994).
J.L. Collins et al., "CP–99, 711: A Non–Peptide Glucagon Receptor Antagonist"Biooorganic & Med.Chem. Ltr. vol. 2, No.9, pp. 915–918(1992).
Azizeh et al., "[des His$^1$, des Phe$^6$, Glu$^9$]Glucagon Amide: A Designed "Pure" Glucagon Antagonist", Bioorganic & vol. 5, No. 16 pp. 1849–1852 (1995).
P. Madsen et al., Discovery and Structure–Activity The First Non–Peptide Competitive Human Glucagon Receptor J. Med.Chem. vol. 41, pp. 5150–5157 (1998).

* cited by examiner

*Primary Examiner*—Paul A. Zucker
(74) *Attorney, Agent, or Firm*—Len Smith; Reza Green; Richard Bork

(57) ABSTRACT

A novel class of compounds, which act to antagonize the action of the glucagon hormone on the glucagon receptor. Owing to their antagonizing effect of the glucagon receptor the compounds may be suitable for the treatment and/or prevention of any diseases and disorders, wherein a glucagon antagonistic action is beneficial, such as hyperglycemia, Type 1 diabetes, Type 2 diabetes, disorders of the lipid metabolism and obesity.

36 Claims, No Drawings

GLUCAGON ANTAGONISTS/INVERSE AGONISTS

CROSS-REFERENCE TO RELATED APPLICATIONS

This application claims priority under 35 U.S.C. 119 of Danish application PA 2000 01733 filed Nov. 17, 2000, and U.S. application Ser. No. 60/252,322, filed Nov. 20, 2000, the contents of both of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as Type 1 diabetes, the insulin-dependent form, or Type 2 diabetes, which is non-insulin-dependent in character. Subjects with Type 1 diabetes are hyperglycemic and hypoinsulinemic, and the conventional treatment for this form of the disease is to provide insulin. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469-E477 (1995); Diabetes 44 [suppl 1], 134A (1995); Diabetes 45, 1076 (1996)). These studies suggest that glucagon suppression or an action that antagonizes glucagon could be a useful adjunct to conventional treatment of hyperglycemia in diabetic patients. The action of glucagon can be suppressed by providing an antagonist or an inverse agonist, ie substances that inhibit or prevent glucagon-induced responses. The antagonist can be peptidic or non-peptidic in nature.

Native glucagon is a 29 amino acid peptide having the sequence:

His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH Glucagon exerts its action by binding to and activating its receptor, which is part of the Glu-cagon-Secretin branch of the 7-transmembrane G-protein coupled receptor family (Jelinek et al., Science 259, 1614, (1993)). The receptor functions by activating the adenylyl cyclase second messenger system and the result is an increase in cAMP levels.

Several publications disclose peptides that are stated to act as glucagon antagonists. Probably, the most thoroughly characterized antagonist is DesHis[1][Glu$^9$]-glucagon amide (Unson et al., Peptides 10, 1171 (1989); Post et al., Proc. Natl. Acad. Sci. USA 90, 1662 (1993)). Other antagonists are DesHis[1],Phe[6][Glu$^9$]-glucagon amide (Azizh et al., Bioorganic & Medicinal Chem. Lett. 16, 1849 (1995)) and NLeu$^9$,Ala$^{11,16}$-glucagon amide (Unson et al., J. Biol. Chem. 269 (17), 12548 (1994)).

Peptide antagonists of peptide hormones are often quite potent. However, they are generally known not to be orally available because of degradation by physiological enzymes, and because of poor distribution in vivo. Therefore, orally available non-peptide antagonists of peptide hormones are generally preferred. Among the non-peptide glucagon antagonists, a quinoxaline derivative, (2-styryl-3-[3-(dimethylamino)propylmethylamino]-6,7-dichloroquinoxaline was found to displace glucagon from the rat liver receptor (Collins, J. L. et al., Bioorganic and Medicinal Chemistry Letters 2(9):915–918 (1992)). WO 94/14426 (The Wellcome Foundation Limited) discloses use of skyrin, a natural product comprising a pair of linked 9,10-anthracenedione groups, and its synthetic analogues, as glucagon antagonists. U.S. Pat. No. 4,359,474 (Sandoz) discloses the glucagon inhibiting properties of 1-phenyl pyrazole derivatives. U.S. Pat. No. 4,374,130 (Sandoz) discloses substituted disilacyclohexanes as glucagon inhibiting agents. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridylimidazoles as glucagon antagonists. Furthermore, WO 97/16442 and U.S. Pat. No. 5,837,719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists. These known glucagon antagonists differ structurally from the present compounds.

DEFINITIONS

The following is a detailed definition of the terms used to describe the compounds of the invention:

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadiynyl and the like.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{3-8}$-cycloalkyl" as used herein represents a saturated, carbocyclic group having from 3 to 8 carbon atoms. Representative examples are cyclopropyl, cyclobutyl, cyclopentyl, cyclohexyl, cycloheptyl, cyclooctyl and the like.

The term "$C_{4-8}$-cycloalkenyl" as used herein represents a non-aromatic, carbocyclic group having from 4 to 8 carbon atoms containing one or two double bonds. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a non-aromatic 3 to 10 membered ring containing one or more heteroatoms selected from nitrogen, oxygen and sulfur and optionally containing one or two double bonds. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic, aromatic ring systems such as 6 membered monocyclic and 9 to 14 membered bi- and tricyclic, carbocyclic, aromatic ring systems. Representative examples are phenyl, biphenylyl, naphthyl, anthracenyl, phenanthrenyl, fluorenyl, indenyl, azulenyl and the like. Aryl is also intended to include the partially hydrogenated derivatives of the ring systems enumerated above. Non-limiting examples of such partially hydrogenated derivatives are 1,2,3,4-tetrahydronaphthyl, 1,4-dihydronaphthyl and the like.

The term "arylene" as used herein is intended to include divalent, carbocyclic, aromatic ring systems such as 6 membered monocyclic and 9 to 14 membered bi- and tricyclic, divalent, carbocyclic, aromatic ring systems. Representative examples are phenylene, biphenylylene, naphthylene, anthracenylene, phenanthrenylene, fluorenylene, indenylene, azulenylene and the like. Arylene is also intended to include the partially hydrogenated derivatives of the ring systems enumerated above. Non-limiting examples of such partially hydrogenated derivatives are 1,2,3,4-tetrahydronaphthylene, 1,4-dihydronaphthylene and the like.

The term "aryloxy" as used herein denotes a group —O—aryl, wherein aryl is as defined above.

The term "aroyl" as used herein denotes a group —C(O)-aryl, wherein aryl is as defined above.

The term "heteroaryl" as used herein is intended to include aromatic, heterocyclic ring systems containing one or more heteroatoms selected from nitrogen, oxygen and sulfur such as 5 to 7 membered monocyclic or 8 to 14 membered bi- and tricyclic aromatic, heterocyclic ring systems containing one or more heteroatoms selected from nitrogen, oxygen and sulfur. Representative examples are furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the ring systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-$C_{1-6}$-alkyl", "heteroaryl-$C_{1-6}$-alkyl", "aryl-$C_{2-6}$-alkenyl" etc. mean $C_{1-6}$-alkyl or $C_{2-6}$-alkenyl as defined above, substituted by an aryl or heteroaryl as defined above, for example:

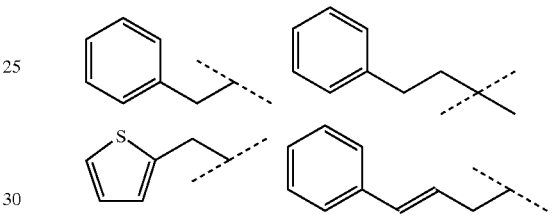

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

DESCRIPTION OF THE INVENTION

The present invention is based on the unexpected observation that the compounds of the general formula (I) disclosed below show a high binding affinity for the glucagon receptor and antagonize the action of glucagon.

Accordingly, the invention is concerned with compounds of the general formula (I):

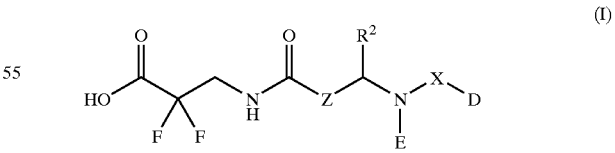

(I)

wherein
$R^2$ is hydrogen or $C_{1-6}$-alkyl,
Z is arylene or a divalent radical derived from a 5 or 6 membered heteroaromatic ring containing 1 or 2 heteroatoms selected from nitrogen, oxygen and sulfur,
which may optionally be substituted with one or two groups $R^7$ and $R^8$ selected from halogen, —CN, —$CF_3$, —$OCF_3$, —$NO_2$, —$OR^9$, —$NR^9R^{10}$ and $C_{1-6}$-alkyl, wherein $R^9$ and $R^{10}$ independently are hydrogen or $C_{1-6}$-alkyl, X is

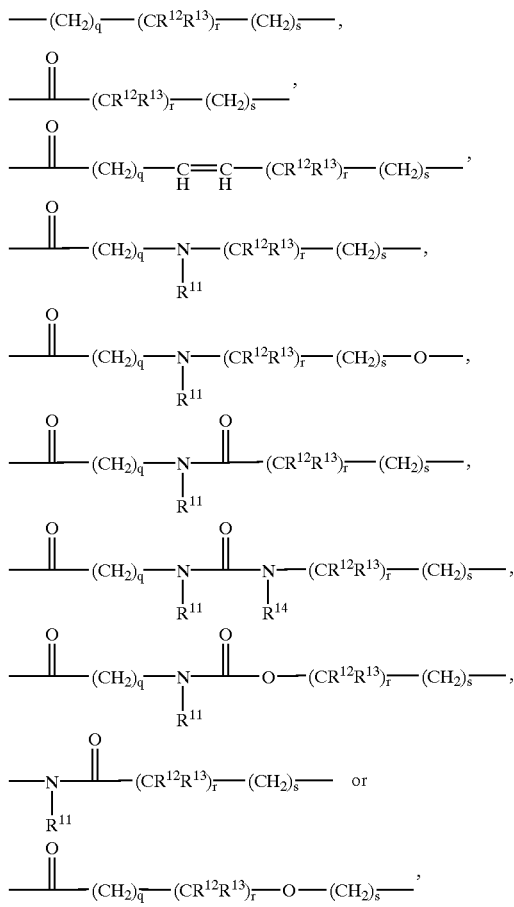

wherein r is 0 or 1, q and s independently are 0 1, 2 or 3, $R^{11}$, $R^{12}$, $R^{13}$ and $R^{14}$ independently are hydrogen or $C_{1-6}$-alkyl, D is

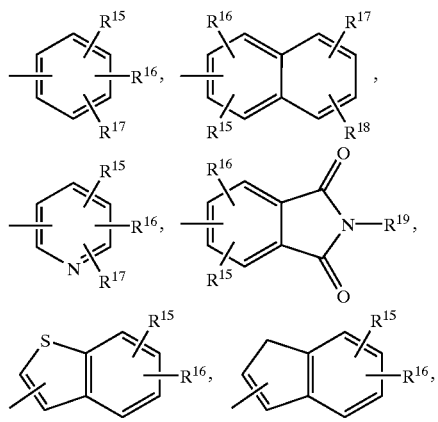

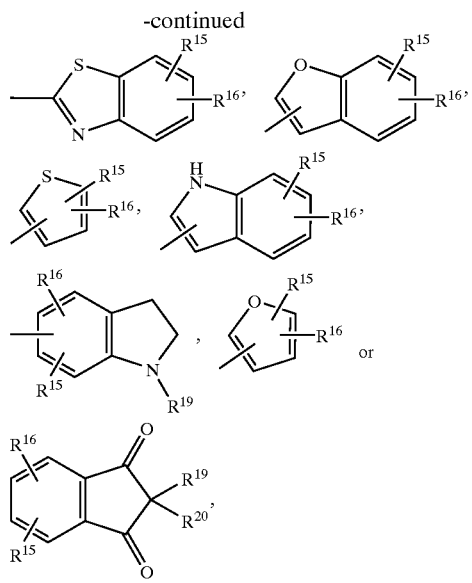

wherein $R^{15}$, $R^{16}$, $R^{17}$ and $R^{18}$ independently are hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$, $C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{21}$, —NR$^{21}$R$^{22}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
of which the cyclic moieties optionally may be substituted with one or more substituents selected from halogen, —CN, —CF$_3$, —OCF$_3$, —NO$_2$, —OR$^{21}$, —NR$^{21}$R$^{22}$ and $C_{1-6}$-alkyl, wherein $R^{21}$ and $R^{22}$ independently are hydrogen, $C_{1-6}$-alkyl or aryl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{15}$ to $R^{18}$ when placed in adjacent positions together may form a bridge —(CR$^{23}$R$^{24}$)$_a$—O—(CR$^{25}$R$^{26}$)$_c$—O—, wherein
a is 0, 1 or 2,
c is 1 or 2,
$R^{23}$, $R^{24}$, $R^{25}$ and $R^{26}$ independently are hydrogen, $C_{1-6}$-alkyl or fluorine,
$R^{19}$ and $R^{20}$ independently are hydrogen, $C_{1-6}$-alkyl, $C_{3-8}$-cycloalkyl or $C_{3-8}$-cycloalkyl-$C_{1-6}$-alkyl,
E is

[structures]

wherein
$R^{27}$ and $R^{28}$ independently are
hydrogen, halogen, —CN, —CF$_3$, —OCF$_3$, —OR$^{32}$, —NR$^{32}$R$^{33}$, $C_{1-6}$-alkyl, $C_{3-8}$-cycloalkyl, $C_{4-8}$-cycloalkenyl or aryl,
wherein the cyclic moieties optionally may be substituted with one or more substituents selected from halogen, —CN, —CF$_3$, —OCF$_3$, —NO$_2$, —OR$^{32}$, —NR$^{32}$R$^{33}$ and $C_{1-6}$-alkyl,
wherein
$R^{32}$ and $R^{33}$ independently are hydrogen or $C_{1-6}$-alkyl, or
$R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
$R^{29}$, $R^{30}$ and $R^{31}$ independently are
hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$,
$C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
of which the cyclic moieties optionally may be substituted with one or more substituents selected from halogen, —CN, —CF$_3$, —OCF$_3$, —NO$_2$, —OR$^{34}$, —NR$^{34}$R$^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or two of the groups $R^{29}$, $R^{30}$ and $R^{31}$ when attached to the same ring carbon atom or different ring carbon atoms together may form a radical —O—(CH$_2$)$_t$—CR$^{36}$R$^{37}$—(CH$_2$)$_l$—O—, —(CH$_2$)$_t$—CR$^{36}$R$^{37}$—(CH$_2$)$_l$— or —S—(CH$_2$)$_t$—CR$^{36}$R$^{37}$—(CH$_2$)$_l$—S—,
wherein
t and l independently are 0, 1, 2, 3, 4 or 5,
$R^{36}$ and $R^{37}$ independently are hydrogen or $C_{1-6}$-alkyl,
as well as any optical or geometric isomer or tautomeric form thereof including mixtures of these or a pharmaceutically acceptable salt thereof.

In one embodiment $R^2$ is hydrogen.
In another embodiment Z is

[structure with $R^7$, $R^8$]

wherein $R^7$ and $R^8$ are as defined for formula (I).
In still another embodiment Z is

[structure]

In a further embodiment X is

[structures showing —(CH$_2$)$_s$—, —C(O)—CH=CH—, —C(O)—(CH$_2$)$_q$—NH—(CH$_2$)$_s$—, etc., and —(CH$_2$)$_s$—]

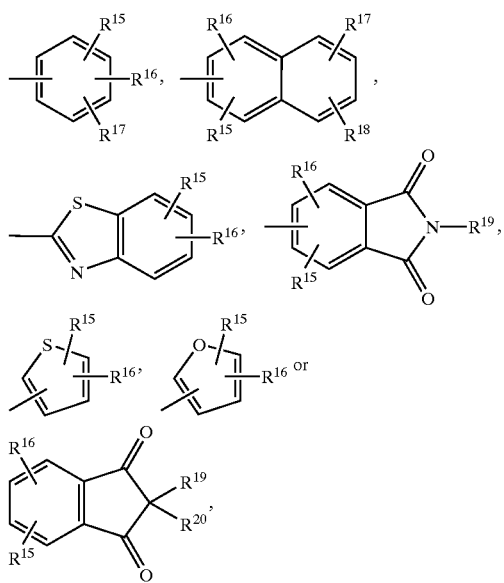

wherein q is 0 or 1, r is 0 or 1, s is 0, 1 or 2, and $R^{12}$ and $R^{13}$ independently are hydrogen or $C_{1-6}$-alkyl.

In still a further embodiment X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

In yet a further embodiment X is —C(O)NH—, —C(O)NHCH$_2$—, —C(O)NHCH(CH$_3$)—, —C(O)NHCH$_2$CH$_2$—, —C(O)CH$_2$—, —CH$_2$—, —C(O)— or —NHC(O)—, such as —C(O)NH—.

In another embodiment D is

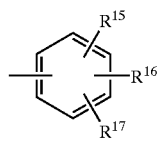

wherein $R^{15}$, $R^{16}$, $R^{17}$, $R^{18}$, $R^{19}$ and $R^{20}$ are as defined for formula (I).

In still another embodiment D is wherein $R^{15}$, $R^{16}$ and $R^{17}$ are as defined for formula (I).

In an embodiment thereof $R^{15}$, $R^{16}$ and $R^{17}$ independently are hydrogen, halogen, —CN, —NO$_2$, —CF$_3$, —OCF$_3$, —SCF$_3$, $C_{1-6}$-alkyl, $C_{1-6}$-alkoxy, —S—$C_{1-6}$-alkyl, —C(O)OR$^{21}$, —C(O)R$^{21}$, —CH$_2$OR$^{21}$, —C(O)NR$^{21}$R$^{22}$, —S(O)$_2$R$^{21}$, —S(O)$_2$CF$_3$, —S(O)$_2$NR$^{21}$R$^{22}$, $C_{3-8}$-cycloalkyl or aryl, or two of the groups $R^{15}$, $R^{16}$ and $R^{17}$ when placed in adjacent positions together form a bridge —(CR$^{23}$R$^{24}$)$_a$—

O—(CR$^{25}$R$^{26}$)$_c$—O—, wherein $R^{21}$ and $R^{22}$ independently are hydrogen or $C_{1-6}$-alkyl, and a, c, $R^{23}$, $R^{24}$, $R^{25}$ and $R^{26}$ are as defined for formula (I).

In another embodiment thereof $R^{15}$, $R^{16}$ and $R^{17}$ independently are hydrogen, halogen, —CN, —CF$_3$, —OCF$_3$ or $C_{1-6}$-alkoxy, such as hydrogen, halogen, —CF$_3$ or —OCF$_3$.

In a further embodiment E is

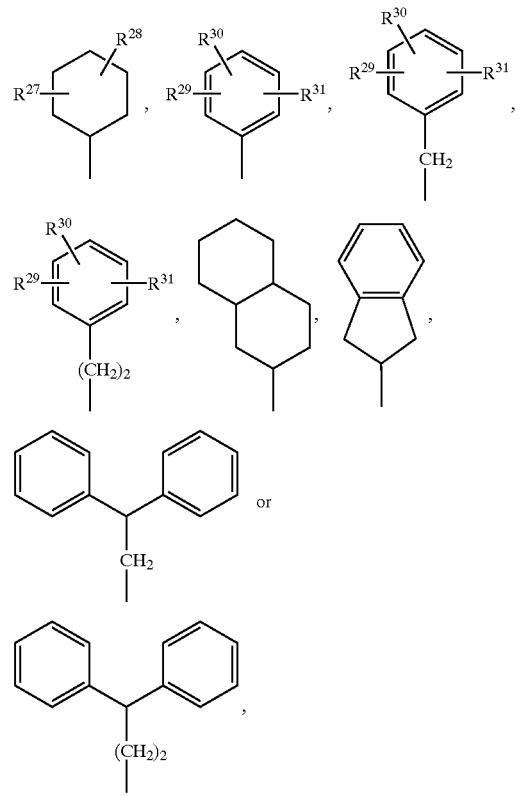

wherein $R^{27}$, $R^{28}$, $R^{29}$, $R^{30}$ and $R^{31}$ are as defined for formula (I).

In still a further embodiment E is

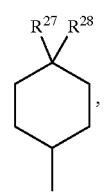

wherein $R^{27}$ and $R^{28}$ are as defined for formula (I).

In an embodiment thereof $R^{27}$ and $R^{28}$ are independently hydrogen, $C_{1-6}$-alkyl, $C_{3-8}$-cycloalkyl, $C_{4-8}$-cycloalkenyl or phenyl, which may optionally be substituted as defined for formula (I).

In another embodiment thereof $R^{27}$ is hydrogen and $R^{28}$ is $C_{1-6}$-alkyl, $C_{4-8}$-cycloalkenyl or $C_{3-8}$-cycloalkyl, which may optionally be substituted as defined for formula (I).

In another embodiment E is

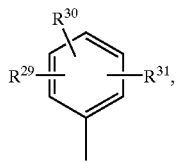

wherein $R^{29}$, $R^{30}$ and $R^{31}$ are as defined for formula (I).
In still another embodiment E is

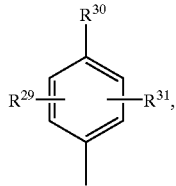

wherein $R^{29}$, $R^{30}$ and $R^{31}$ are as defined for formula (I).
In an embodiment thereof $R^{29}$, $R^{30}$ and $R^{31}$ are independently hydrogen, $-CHF_2$, $-CF_3$, $-OCF_3$, $-OCHF_2$, $-OCH_2CF_3$, $-OCF_2CHF_2$, $-SCF_3$, $-OR^{34}$, $-NR^{34}R^{35}$, $-SR^{34}$, $-S(O)R^{34}$, $-S(O)_2R^{34}$, $-C(O)NR^{34}R^{35}$, $-OC(O)NR^{34}R^{35}$, $-NR^{34}C(O)R^{35}$, $-OCH_2C(O)NR^{34}R^{35}$, $-C(O)R^{34}$ or $-C(O)OR^{34}$, $C_{1-6}$-alkyl, $C_{2-6}$-alkenyl or $C_{2-6}$-alkynyl,
which may optionally be substituted with one or more substituents selected from halogen, $-CN$, $-CF_3$, $-OCF_3$, $-NO_2$, $-OR^{34}$, $-NR^{34}R^{35}$ and $C_{1-6}$-alkyl, $C_{3-8}$-cycloalkyl or $C_{4-8}$-cycloalkenyl,
which may optionally be substituted with one or more substituents selected from halogen, $-CN$, $-CF_3$, $-OCF_3$, $-NO_2$, $-OR^{34}$, $-NR^{34}R^{35}$ and $C_{1-6}$-alkyl,
wherein $R^{34}$ and $R^{35}$ independently are hydrogen, $C_{1-6}$-alkyl or aryl,
or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

In another embodiment thereof $R^{29}$, $R^{30}$ and $R^{31}$ are independently hydrogen, $C_{1-6}$-alkoxy, $-CF_3$, $-OCF_3$ or $-NR^{34}R^{35}$, wherein $R^{34}$ and $R^{35}$ are as defined for formula (I), or $C_{1-6}$-alkyl, $C_{3-8}$-cycloalkyl or $C_{4-8}$-cycloalkenyl, which are optionally substituted as defined for formula (I).

In still another embodiment thereof $R^{29}$, $R^{30}$ and $R^{31}$ are independently hydrogen or $C_{1-6}$-alkyl, $C_{3-8}$-cycloalkyl or $C_{4-8}$-cycloalkenyl, which are optionally substituted as defined for formula (I).

In a further embodiment thereof $R^{29}$, $R^{30}$ and $R^{31}$ are independently hydrogen, $C_{1-6}$-alkyl, $C_{3-8}$-cycloalkyl or $C_{4-8}$-cycloalkenyl, wherein $C_{3-8}$-cycloalkyl or $C_{4-8}$-cycloalkenyl are optionally substituted with $C_1$-alkyl.

In still a further embodiment thereof $R^{29}$ and $R^{31}$ are both hydrogen and $R^{30}$ is $C_1$-alkyl, $C_{3-8}$-cycloalkyl or $C_{4-8}$-cycloalkenyl, wherein $C_{3-8}$-cycloalkyl or $C_{4-8}$-cycloalkenyl are optionally substituted with $C_{1-6}$-alkyl.

In yet a further embodiment thereof $R^{29}$ and $R^{31}$ are both hydrogen and $R^{30}$ is $C_{1-6}$-alkyl.

In still another embodiment thereof $R^{29}$ and $R^{30}$ are both hydrogen and $R^{30}$ is $C_{4-8}$-cycloalkenyl which is optionally substituted with $C_{1-6}$-alkyl.

In another aspect, the invention is concerned with compounds of the general formula (I'):

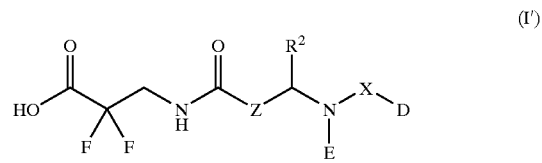

wherein
$R^2$ is hydrogen or $C_{1-6}$-alkyl,
Z is arylene or a divalent radical derived from a 5 or 6 membered heteroaromatic ring containing 1 or 2 heteroatoms selected from nitrogen, oxygen and sulfur,
which may optionally be substituted with one or two groups $R^7$ and $R^8$ selected from halogen, $-CN$, $-CF_3$, $-OCF_3$, $-NO_2$, $-OR^9$, $-NR^9R^{10}$ and $C_{1-6}$-alkyl,
wherein $R^9$ and $R^{10}$ independently are hydrogen or $C_{1-6}$-alkyl,
X is

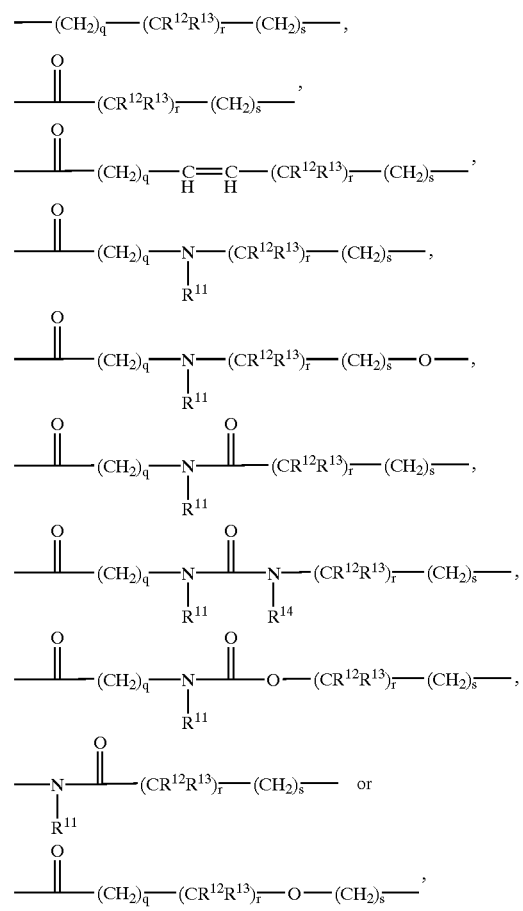

wherein
r is 0 or 1,
q and s independently are 0, 1, 2 or 3,
$R^{11}$, $R^{12}$, $R^{13}$ and $R^{14}$ independently are hydrogen or $C_{1-6}$-alkyl, D is

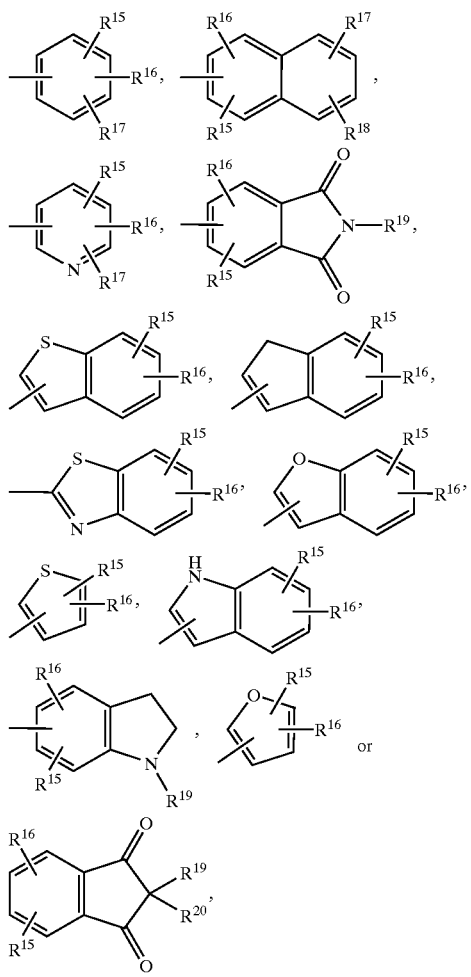

wherein
$R^{15}$, $R^{16}$, $R^{17}$ and $R^{18}$ independently are
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$, C$_{1-6}$-alkyl, C$_{2-6}$-alkenyl or C$_{2-6}$-alkynyl,
  which may optionally be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, wherein $R^{21}$ and $R^{22}$ independently are hydrogen, C$_{1-6}$alkyl or aryl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{15}$ to $R^{18}$ when placed in adjacent positions together may form a bridge —(CR$^{23}$R$^{24}$)$_a$—O—(CR$^{25}$R$^{26}$)$_c$—O—, wherein
a is 0, 1 or 2,
c is 0, 1 or 2,
$R^{23}$, $R^{24}$, $R^{25}$ and $R^{26}$ independently are hydrogen, C$_{1-6}$-alkyl or fluorine,
$R^{19}$ and $R^{20}$ independently are hydrogen, C$_{1-6}$-alkyl, C$_{3-8}$-cycloalkyl or C$_{3-8}$-cycloalkyl-C$_{1-6}$alkyl, E is

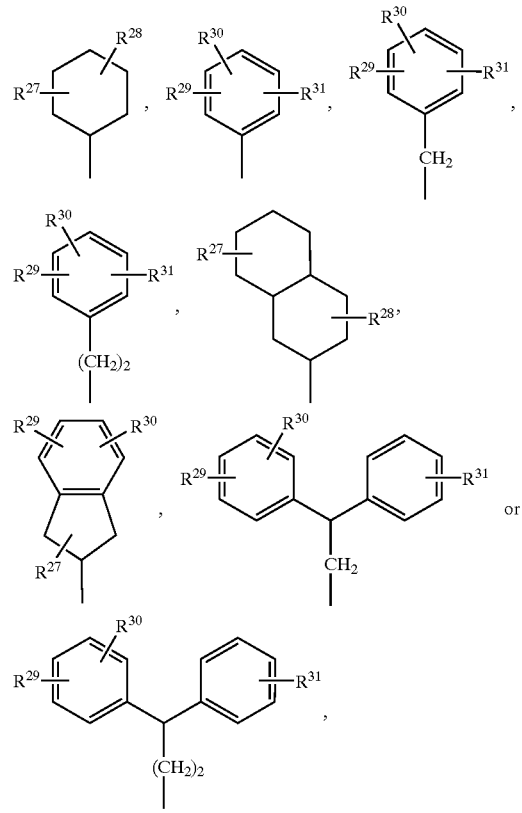

wherein
$R^{27}$ and $R^{28}$ independently are
hydrogen, halogen, —CN, —CF$_3$, —OCF$_3$, —OR$^{32}$, —NR$^{32}$R$^{33}$, C$_{1-6}$-alkyl, C$_{3-8}$-cycloalkyl, C$_{4-8}$-cycloalkenyl or aryl,
wherein the aryl group optionally may be substituted with one or more substituents selected from halogen, —CN, —CF$_3$, —OCF$_3$, —NO$_2$, —OR$^{32}$, —NR$^{32}$R$^{33}$ and C$_{1-6}$-alkyl,
wherein
$R^{32}$ and $R^{33}$ independently are hydrogen or C$_{1-6}$alkyl, or $R^{32}$ and $R^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{29}$, $R^{30}$ and $R^{31}$ independently are hydrogen, halogen, —$CHF_2$, —$CF_3$, —$OCF_3$, —$OCHF_2$, —$OCH_2CF_3$, —$OCF_2CHF_2$, —$SCF_3$, —$OR^{34}$— $NR^{34}R^{35}$, —$SR^{34}$, —$S(O)R^{34}$, —$S(O)_2R^{34}$, —$C(O)NR^{34}R^{35}$, —$OC(O)NR^{34}R^{35}$, —$NR^{34}C(O)R^{35}$, —$OCH_2C(O)NR^{34}R^{35}$, —$C(O)R^{34}$ or —$C(O)OR^{34}$, $C_{1-6}$-alkyl, $C_{2-6}$-alkenyl or $C_{2-6}$-alkynyl, which may optionally be substituted with one or more substituents selected from halogen, —CN, —$CF_3$, —$OCF_3$, —$NO_2$, —$OR^{34}$, —$NR^{34}R^{35}$ and $C_{1-6}$-alkyl, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl, heterocyclyl-$C_{2-6}$-alkynyl, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, hetero-aryl-$C_{2-6}$-alkenyl or heteroaryl-$C_{2-6}$-alkynyl, of which the cyclic moieties optionally may be substituted with one or more substituents selected from halogen, —CN, —$CF_3$, —$OCF_3$, —$NO_2$, —$OR^{34}$, —$NR^{34}R^{35}$ and $C_{1-6}$-alkyl, wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{29}$, $R^{30}$ and $R^{31}$ when attached to the same ring carbon atom or different carbon atoms together may form a radical —O—$(CH_2)_t$—$CR^{36}R^{37}$—$(CH_2)_l$—O—, —$(CH_2)_t$—$CR^{36}R^{37}$—$(CH_2)_l$— or —S—$(CH_2)_t$—$CR^{36}R^{37}$—$(CH_2)_l$—S—, wherein t and l independently are 0, 1, 2, 3, 4 or 5, $R^{36}$ and $R^{37}$ independently are hydrogen or $C_{1-6}$-alkyl, as well as any optical or geometric isomer or tautomeric form thereof including mixtures of these or a pharmaceutically acceptable salt thereof.

In specific embodiments thereof, $R^2$, Z, E, X and D are as described in the embodiments above.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, butyl-, tetramethylammonium salts and the like.

Also intended as pharmaceutically acceptable acid addition salts are the hydrates which the present compounds are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment and/or prevention of disorders and diseases in which such an antagonism is beneficial.

Accordingly, the present compounds may be applicable for the treatment and/or prevention of hyperglycemia, IGT (impaired glucose tolerance), insulin resistance syndromes, syndrome X, Type 1 diabetes, Type 2 diabetes, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

They may also be useful as tool or reference molecules in labelled form in binding assays to identify new glucagon antagonists.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment and/or prevention of a disorder or disease, wherein a glucagon antagonistic action is beneficial.

The invention also relates to a method for the treatment and/or prevention of disorders or diseases, wherein a glucagon antagonistic action is beneficial the method comprising administering to a subject in need thereof an effective amount of a compound according to the invention.

In a preferred embodiment of the invention the present compounds are used for the preparation of a medicament for the treatment and/or prevention of any glucagon-mediated conditions and diseases.

In a preferred embodiment of the invention the present compounds are used for the preparation of a medicament for the treatment and/or prevention of hyperglycemia.

In yet a preferred embodiment of the invention the present compounds are used for the preparation of a medicament for lowering blood glucose in a mammal. The present compounds are effective in lowering the blood glucose, both in the fasting and the postprandial stage.

In another preferred embodiment of the invention the present compounds are used for the preparation of a pharmaceutical composition for the treatment and/or prevention of IGT.

In still another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In yet a further preferred embodiment of the invention the present compounds are used for the preparation of a pharmaceutical composition for the treatment and/or prevention of disorders of the lipid metabolism.

In still a further preferred embodiment of the invention the present compounds are used for the preparation of a pharmaceutical composition for the treatment and/or prevention of an appetite regulation or energy expenditure disorder.

In a further aspect of the invention, treatment of a patient with the present compounds is combined with diet and/or exercise.

In still a further aspect of the invention the present compounds are administered in combination with one or more further active substances in any suitable ratios. Such further active substances may eg be selected from antiobesity agents, antidiabetics, antihypertensive agents, agents for the treatment of complications resulting from or associated with diabetes and agents for the treatment of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TRβ, agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Suitable antidiabetic agents include insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 368 187 (Aventis), eg Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, insulin secretagogues, such as glimepride, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention the present compounds are administered in combination with insulin, $N^{\epsilon B29}$-tetradecanoyl des (B30) human insulin, $Asp^{B28}$ human insulin, $Lys^{B28}Pro^{B29}$ human insulin or Lantus, or a mixpreparation comprising one or more of these.

In a further embodiment of the invention the present compounds are administered in combination with a sulfonylurea eg tolbutamide, chlorpropamide, tolazamide, glibenclamide, glipizide, glimepiride, glicazide or glyburide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/Cl-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose. In another embodiment of the invention the present compounds are administered in combination with an agent acting on the ATP-dependent potassium channel of the β-cells eg tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and a-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose approx. | 9 mg |
| Mywacett 9-40 T** approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

The compounds according to the invention may be prepared according to the general procedures outlined below. All starting materials are known or may easily be prepared from known starting materials.

All temperatures are set forth in degrees Celsius and unless otherwise indicated, all parts and percentages are by weight when referring to yields and all parts are by volume when referring to solvents and eluents.

The following terms are intended to have the following meanings:

| | |
|---|---|
| DCM | dichloromethane |
| DMF: | N,N-dimethylformamide |
| DMSO: | dimethyl sulphoxide |
| M.p.: | melting point |
| TFA: | trifluoroacetic acid |
| THF: | tetrahydrofuran |
| EDAC: | 1-ethyl-3-(3-dimethylaminopropyl)carbodiimide hydrochloride |
| HOBt: | 1-hydroxybenzotriazole |
| HOAt: | 3-hydroxy-3H-[1,2,3]triazolo[4,5-b]pyridine |
| EGTA: | ethylene glycol bis(β-aminoethyl ether) N,N,N',N'-tetracetic acid |
| IBMX: | isobutylmethylxanthine |

General Procedure (A) for Synthesis of Compounds of the General Formula (Ia) According to the Invention:

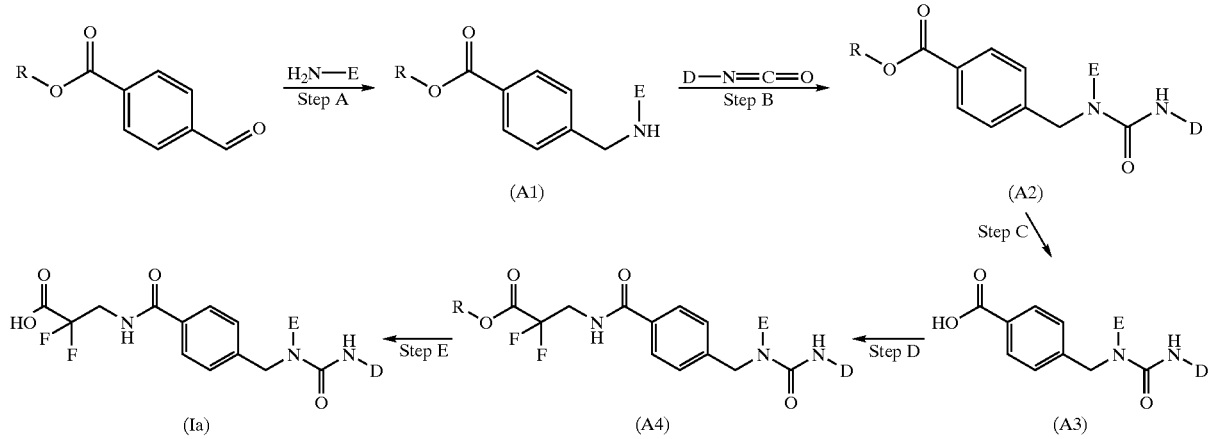

wherein D and E are as defined for formula (I) and R is $C_{1-6}$-alkyl.

Intermediates to be Used in Step A:

4-Cyclohex-1-enylphenylamine is described in the literature: v Brown et al., Justus Liebigs, Ann. Chem., 1929 (472), 1–89.

4-(4-tert-Butylcyclohex-1-enyl)phenylamine was prepared by similar method.

4-Cyclohexylphenylamine is commercially available (e.g. from Lancaster or Avocado).

Bicyclohexyl-4-ylamine is described in the literature: H. Booth et al., J. Chem. Soc. (B), 1971, 1047–1050.

Intermediates to be Used in Step D:

3-Amino-2,2-difluoropropionic acid methyl ester hydrochloride

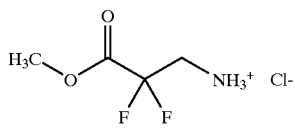

Step 1: 2,2-Difluorosuccinic acid 1-methyl ester

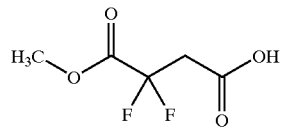

Commercially available 2,2-difluorosuccinic acid (8.0 g, 51.9 mmol) was dissolved in THF and cooled on ice before addition of 1,3-dicyclohexylcarbodiimide (11.8 g, 57.2 mmol). The mixture was stirred at room temperature for 3 hours, cooled and filtered. The filtrate was concentrated in vacuo. The residue was stirred with methanol (50 ml) for 3 hours at room temperature and then solvents were removed in vacuo to afford the crude ester as an oil (8.4 g). The oil was purified by column chromatography on silica gel column and elution with a 0–100% ethyl acetate/toluene gradient to afford 2,2-difluorosuccinic acid 1-methyl ester as a colorless oil (6.8 g).

$^1$H NMR (DMSO-$d_6$): δ3.37 (t, 2H), 3.85 (s, 3H), 13.22 (brs, 1H).

Step 2: 3-Benzyloxycarbonylamino-2,2-difluoropropionic acid methyl ester

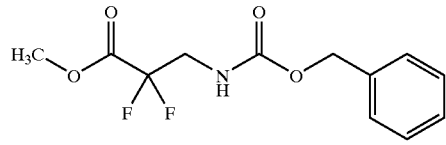

2,2-Difluorosuccinic acid 1-methyl ester (6.7 g, 39.9 mmol) and thionyl chloride were heated at reflux for 1 hour. The mixture was co-evaporated with dry toluene (3×) to leave an oil. The residue was dissolve in dry toluene (100 ml) and heated to 70° C. before adding trimethylsilyl azide (6.3 ml, 47.5 mmol) over 30 min. The mixture was stirred for 16 hours at 80° C. and evaporated to an oil. The residue was dissolved in dry toluene, charged with dry benzyl alcohol (5.0 ml, 50.2 mmol) and stirring was continued for 16 hours at 80° C. The mixture was concentrated in vacuo and the residue was partitioned between ethyl acetate (100 ml) and water (100 ml). The organic layer was washed twice with water and dried over magnesium sulphate, filtered and concentrated in vacuo. The residue was subjected to flash column chromatography using DCM as eluent (200 ml) removing highly polar impurities before a second column chromatography eluting with 10% ethyl acetate/toluene. Evaporation of proper fractions in vacuo afforded 3.3 g (23%) of 3-benzyloxycarbonylamino-2,2-difluoropropionic acid methyl ester as an oil.

$^1$H NMR (DMSO-$d_6$): δ3.62–3.77 (m, 2H), 3.78 (s, 3H), 5.05 (s, 2H), 7.35 (s, 5H), 7.90 (t, 1H),

Step 3: 3-Benzyloxycarbonylamino-2,2-difluoropropionic acid

3-Benzyloxycarbonylamino-2,2-difluoropropionic acid methyl ester (3.3 g, 12.1 mmol), THF (50 ml), methanol (50 ml) and 1 N sodium hydroxide solution (50ml) were mixed and stirred for 16 hours at room temperature. After adjusting the pH to acidic reaction and removal of organic solvent by evaporation, the aqueous residue was extracted twice with ethyl acetate. The combined organic layers were washed twice with 5% brine, dried over magnesium sulphate and filtered through a short silica column before concentration in vacuo to afford 2.6 g (83%) of 3-benzyloxycarbonylamino-2,2-difluoropropionic acid as an oil.

$^1$H NMR (DMSO-$d_6$): δ3.67 (dt, 2H), 5.05 (s, 2H), 7.35 (s, 5H), 7.83 (t, 1H).

Step 4: 3-Amino-2,2-difluoropropionic acid

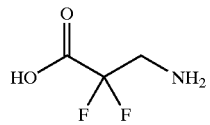

3-Benzyloxycarbonylamino-2,2-difluoropropionic acid (2.6 g, 10.0 mmol) was dissolved in abs. ethanol (100 ml) and Pd-C, 10% (100 mg) was added under a nitrogen atmosphere. The mixture is hydrogenated for 3 hours at 40 psi, filtered on micro filter, washed with abs. ethanol and a small amount of water. The colourless solution was concentrated to approx. 10 ml and acetone (75 ml) was added dropwise. The precipitate was filtered off and dried to afford 0.8 g (64%) of 3-amino-2,2-difluoropropionic acid as white crystals. M.p. 125–127° C.

$^1$H NMR (DMSO-$d_6$): δ3.28 (t, 2H), 8.42 (bs, 2H).

Step 5: 3-Amino-2,2-difluoropropionic acid methyl ester hydrochloride

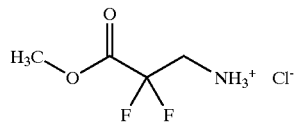

Thionyl chloride (1.2 ml, 16.5 mmol) was added dropwise to ice cold dry methanol (20 ml) over 10 min. 3-Amino-2,2-difluoropropionic acid (0.7 g, 5.6 mmol) was added and stirring was continued in the cold for additional 15 min. The cooling source was removed and stirring was continued at room temperature for 16 hours. The mixture was co-evaporated with toluene (3×) to give a white suspension, which upon filtration and drying at 40° C. for 16 hours gave 0.96 g (98%) of the title compound.

$^1$H NMR (DMSO-$d_6$): δ3.65 (t, 2H), 3.89 (s, 3H), 9.07 (br s, 3H). $^{13}$C NMR (DMSO-$d_6$): δ39.8 (CH$_2$), 54.6 (CH$_3$), 112.8 (CF$_2$), 162 (C=O).

Using the general procedure (A) the following compounds have been prepared. The procedure is further illustrated by the following example.

Example 1
3-{4-[1-(4-Cyclohex-1-enylphenyl)-3-(3,5-dichlorophenyl)ureidomethyl]benzoylamino-}-2,2-difluoropropionic acid)

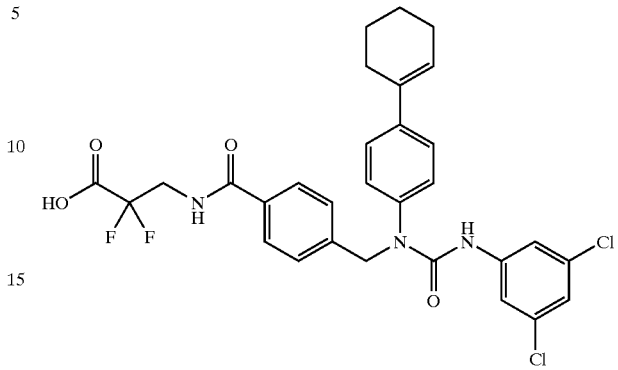

Step A:

To a solution of E—NH$_2$ (eg 4-cyclohexenylaniline, prepared as described above) (0.023 mol) and methyl 4-formylbenzoate (3.77 g, 0.023 mol) in DCM (50 ml) and methanol (15 ml) is added a catalytic amount of acetic acid. After stirring the solution for 3 hours, Na(OAc)$_3$BH (24 g, 0.115 mol) is added. The reaction is allowed to stir at room temperature for 16 hours. The reaction mixture is diluted with ethyl acetate and washed with aqueous sodium bicarbonate (3×), brine (2×), dried over magnesium sulphate, filtered, and concentrated to give a solid. The crude product is purified by column chromatography eluting with mixtures of ethyl acetate and heptane to give 4-[(4-cyclohex-1-enylphenylamino)methyl]benzoic acid methyl ester (A1) (5 g, 0.015 mol).

$^1$H NMR (DMSO-$d_6$): δ1.56 (m, 2H), 1.67 (m, 2H), 2.11 (m, 2H), 2.25 (m, 2H), 3.81 (s, 3H), 4.34 (d, 2H), 5.89 (t, 1H), 6.34 (t, 1H), 6.49 (d, 2H), 7.10 (d, 2H), 7.47 (d, 2H).

Step B:

The above 4-[(4-cyclohex-1-enylphenylamino)methyl]benzoic acid methyl ester (5 g, 0.015 mol) is dissolved in anhydrous DCM and diisopropylethylamine (5.8 g, 0.045 mol) is added. To this solution is added an isocyanate (D—N=C=O) (0.018 mol), eg. 3,5-dichlorophenyl isocyanate. After stirring the reaction mixture for 3 hours, the solution is diluted with ethyl acetate and washed with 1N hydrochloric acid (2×), water, brine, dried over magnesium sulphate, filtered, and concentrated in vacuo. The residue is purified by column chromatography eluting with mixtures of ethyl acetate and heptane to give (A2).

Step C:

To a solution of (A2) (2 mmol) in THF (30 ml) and methanol (10 ml) is added an excess of 2 M lithium hydroxide (10 ml). After stirring the reaction mixture for 3 hours, the solution is concentrated. The residue is taken up in ethyl acetate and washed with 1 N hydrochloric acid (2×), water (2×), brine, and dried over magnesium sulphate. Evaporation of the solvent affords (A3).

Step D:

To a solution of (A3) (0.81 mmol) in DMF (4 ml) are added 3-[(dimethyliminium)(dimethylamino)methyl]-1,2,3-benzotriazol-1-ium-1-olate hexafluorophosphate (0.37 g, 0.90 mmol), diisopropylethylamine (0.30 g, 2.4 mmol), and 3-amino-2,2-difluoropropionic acid methyl ester hydrochloride (2.4 mmol). After stirring the solution for 16 hours, the reaction is diluted with ethyl acetate and washed with 1N hydrochloric acid (3×), brine (3×), dried over magnesium sulphate, filtered, and concentrated. The residue is purified by column chromatography and eluted with mixtures of ethyl acetate and heptane to afford (A4).

Step E:

(A4) is dissolved in THF (6 ml) and methanol (3 ml). A solution of 2 M lithium hydroxide (3 ml) is then added and the reaction is stirred at room temperature for 30 min. The solvents are evaporated under reduced pressure. The residue is taken up in ethyl acetate and washed with 1 N hydrochloric acid (2×), brine (2×), dried over magnesium sulphate, filtered, and concentrated in vacuo to afford the title compound of the general formula (Ia).

$^1$H NMR (DMSO-$d_6$): δ1.60 (m, 2H), 1.70 (m, 2H), 2.18 (m, 3H), 2.33 (m, 2H), 3.93 (m, 2H), 6.18 (m, 1H), 7.12–7.22 (m, 3H), 7.37 (d, 2H), 7.41 (d, 2H), 7.62 (d, 2H), 7.78 (s, 2H), 8.54 (s, 1H), 8.85 (t, 1H).

Example 2
3-{4-[1-[4-(4-tert-Butylcyclohex-1-enyl)phenyl]-3-(3,5-dichlorophenyl)ureidomethyl]benzoylamino}-2,2-difluoropropionic acid

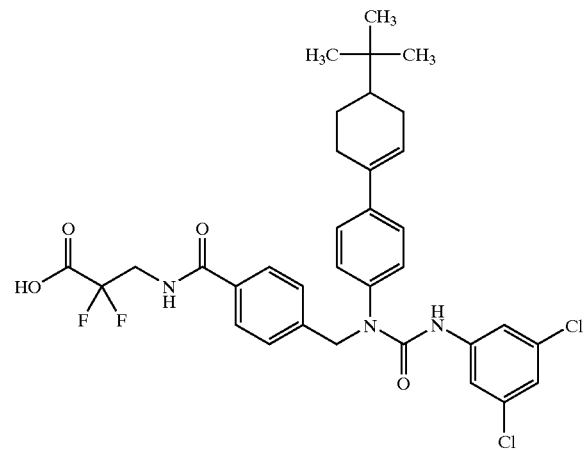

$^1$H-NMR (DMSO-$d_6$): δ0.88 (s, 9H), 1.23 (m, 2H), 1.92 (bm, 2H), 2.13-2.43 (m, 3H), 3.93 (m, 2H), 4.94 (s, 2H), 6.18 (m, 1H), 7.13 (m, 1H), 7.17 (d, 2H), 7.32 (d, 2H), 7.39 (d, 2H), 7.62 (s, 2H), 7.74 (d, 2H), 8.47 (t, 1H), 8.53 (s, 1H), 8.83 (t, 1H); M.p. 125–127° C.

General Procedure (B) for the Synthesis of Compounds of the General Formula (Ia) According to the Invention:

wherein D and E are as defined for formula (I) and R is $C_{1-6}$alkyl.

Preparation of methyl 2,2-difluoro-3-[(4-formylbenzoyl)amino]propionate as starting material:

To a solution of the 4-formylbenzoic acid in a suitable solvent such as DCM, DMF or THF is added diisopropylethylamine (3 eq) and 3-[(dimethyliminium)(dimethylamino)methyl]-1,2,3-benzotriazol-1-ium-1-olate hexafluorophosphate (1.1 eq). The reaction is allowed to stir for 30 min before ethyl or methyl 3-amino-2,2-difluoropropionate hydrochloride (1.1 eq) is added. The solution is stirred at room temperature for 4 hours. The solvents are evaporated under reduced pressure. The residue is taken up in ethyl acetate and 1N hydrochloric acid. The organic layer is separated and washed with water (2×), aqueous sodium hydrogen carbonate (3×), brine (2×), dried over magnesium sulphate and concentrated to give the desired product.

Step A:

The aldehyde (0.011 mmol) in DCM is dispensed into the wells of a deepwell plate containing the desired amines (E—NH$_2$) in DCM. To this solution is added sodium triacetoxyborohydride (1.5 eq) followed by a catalytic amount of acetic acid. The reaction is left to proceed for 15 hours.

Step B:

To the resulting amines from step A is added the desired isocyanate (D—N=C=O) (0.011 mmol) in DCM. The reaction mixtures are agitated for three hours and the solvents are removed under reduced pressure to give the desired ureas.

Step C:

The residue obtained in step B is dissolved in DMF and aqueous 2 M lithium hydroxide (10 eq.) is added into each reaction well. The samples are shaken overnight and filtered. Aqueous 1 N hydrochloric acid is then added to give the desired carboxylic acids.

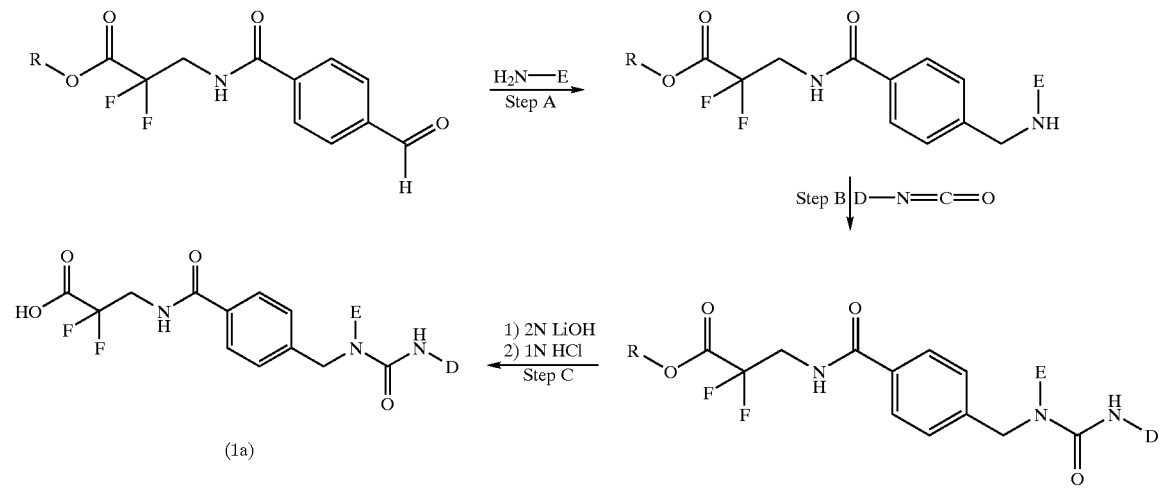

General Procedure (C) for Solid Phase Synthesis of Compounds of the General Formula (Ia) According to the Invention:

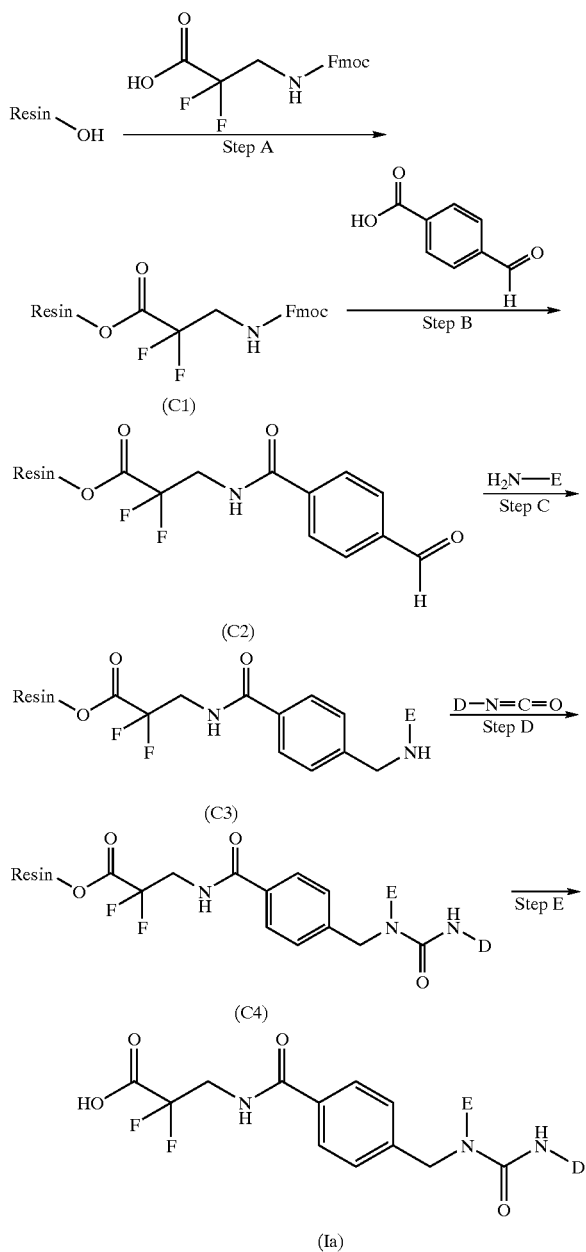

wherein D and E are as defined for formula (I), R is $C_{1-6}$-alkyl and Resin denotes a polystyrene resin with a linker such as the Wang linker:

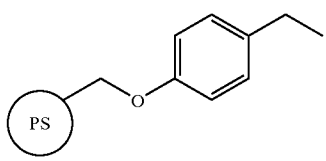

wherein PS denotes polystyrene.

Step A:

The reaction is known (Wang S. J., J. Am. Chem. Soc. 95, 1328, 1973) and is generally performed by stirring polystyrene resin loaded with a linker such as the Wang linker with a 4–10 molar excess of Fmoc-protected amino acid activated with a 2–5 molar excess of diisopropylcarbodiimide or dicyclohexylcarbodiimide in the presence of a catalyst such as N,N-4-dimethylaminopyridine. The esterification is carried out in a solvent such as THF, dioxane, toluene, DCM, DMF, N-methylpyrrolidinone or a mixture of two or more of these. The reactions are performed between 0° C. to 80° C., preferably between 20° C. to 40° C. When the esterification is complete excess of reagents is removed by filtration. The resin is successively washed with the solvent used in the reaction, followed by washings with methanol. The resin bound product can be further dried and analyzed.

Step B:

The Fmoc protecting group is removed using a solution of 20% piperidine in DMF which is added to the resin and vortexed for 0.5 hours. After draining the resin is washed with DMF containing HOBt (50 mg/ml) and DMF. The acylation (The combinatorial index, Ed. Bunin, B. A. 1998, Academic Press, p. 78) is performed by adding an excess of acid in a solvent such as DMF, N-methylpyrrolidinone, THF, DCM, 1,2-dichloroethane, acetonitrile, DMSO or a mixture of two or more of these, optionally in the presence of a base such as N-methylmorpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazole-1-yl)-1,1,3,3-tetramethyluronium hexafluorophosphate or bromo-tris-pyrrolidinophosphonium hexafluorophosphate in a solvent such as DMF, N-methylpyrrolidinone, THF, DCM, 1,2-dichloroethane, acetonitrile, DMSO or a mixture of two or more of these, optionally in the presence of a side reaction inhibitor such as 3-hydroxy4-oxo-3,4-dihydro-1,2,3-benzotriazine, HOBt or 1-hydroxy-7-azabenzotriazole. The reaction is performed between 20° C. and 40° C., preferably at 25° C. Excess reagents are filtered off and the resin is washed several times with the solvent used during the reaction.

Step C:

The reaction is generally known (The combinatorial index, Ed. Bunin, B. A. 1998, Academic Press, p. 133) and is generally performed by stirring resin bound aldehyde or ketone with an excess of amine at low pH (by addition of an acid, such as acetic acid or formic acid) in a solvent such as THF, DMF, N-methylpyrrolidinone, methanol, ethanol, DMSO, DCM, 1,2-dichloroethane, trimethyl orthoformate, triethyl orthoformate, or a mixture of two or more of these. As reducing agent sodium cyanoborohydride may be used. The reaction is performed between 20° C. and 120° C., preferably at 25° C.

Step D:

The reaction is generally known (Organic synthesis on solid phase. Dörwald, F. Z. 2000, Wiley VCH, p. 331) and is generally performed by stirring resin bound amine with an excess of isocyanate in a solvent such as THF, DMF, N-methylpyrrolidinone, DCM, 1,2-dichloroenthane, toluene or a mixture of two or more of these. The reaction is performed between 20° C. and 80° C., preferably at 25° C.

Step E:

The reaction is known (The combinatorial index, Ed. Bunin B. A., 1998, Academic press, p. 21) and is generally performed by stirring resin bound intermediate obtained in step D with a 50–95% solution of TFA. The final cleavage is carried out in a solvent such as THF, DCM, 1,2-dichloroethane, 1,3-dichloropropane, toluene or a mixture of two or more of these. The reaction is performed between 0° C. and 80° C., preferably between 20° C. and 40° C. When the reaction is complete the product is removed by filtration. The resin is successively washed with DCM. The product and washings are collected. The solvent is removed and the product is dried in vacuo.

Optionally, the resin can be a 2-chlorotrityl resin. In that case, step A is a nucleophilic reaction of Fmoc-protected beta alanine with 2-chlorotritylchloride resin in the presence of a base, such as triethylamine or N,N-diisopropyl-N-ethylamine. All other steps are identical to those described above with the exception of step E, cleavage from the resin. This can be done with only 5% TFA in DCM.

More specifically, preparation of the compounds of the invention according to the general procedure (C) may be prepared as follows:

Step A: Resin Bound Fmoc δ-Alanine (C1)

150 μmol Fmoc α,α-difluoro-β-alanine is dissolved in 500 μl of a mixture of DMF and diisopropylethylamine (430:70) and added to 50 mg polystyrene resin functionalised with a Wang linker. 200 μmol PyBrOP dissolved in DMF (500 μl) is added. After shaking the suspension for 4 hours at 25° C., the resin is isolated by filtration and washed with 3×1 ml DMF.

Step B: Resin Bound 3-(4-formylbenzoylamino) propionic Acid (C2)

To the above resin bound Fmoc (α,α-difluoro-β-alanine (C1) is added 1000 μl of a 20% solution of piperidine in DMF. Upon shaking for 30 min, the resin is drained and washed with 1 ml DMF containing HOBt (50 mg/ml) and DMF (2×1 ml). Then 200 μmol 4-formylbenzoic acid (30 mg) and diisopropylethylamine (70 μl) are dissolved in DMF (430 μl) and added to the resin followed by 200 μmol PyBrOP dissolved in DMF (500 μl). The mixture is shaken for 4 hours at 25° C. followed by filtration and washing of the resin with DMF (3×1 ml) and trimethylorthoformate (1×1 ml).

Step C: (C3)

The above resin bound 3-(4-formylbenzoylamino) propionic acid (C2) (50 mg) is treated with a solution of E—NH₂ (500 μmol) in a mixture of DMF (500 pi) and trimethylorthoformate (500 μl). Glacial acetic acid (100 μl) is added and the mixture is shaked for 1 hour at 25° C. Sodium cyanoborohydride (750 μmol) suspended in a mixture of DMF and trimethylorthoformate (1:1, 1 ml) is added and the mixture is vortexed at 25° C. for 16 hours followed by filtration and washing with a mixture of DMF and water (4:1, 2×1 ml) followed by 3×1 ml DMF and 2×1 ml DCM to afford (C3).

Step D: (C4)

200 μmol isocyanate (D—N=C=O) dissolved in 500 μl DCM is added to (C3) (50 mg). Shaking the mixture for 16 hours at 25° C. followed by filtration and washing of the resin with 4×1 ml DMF, 2×1 ml water, 3×1 ml THF and 5×1 ml DCM afford (C4).

Step E:

(C4) (50 mg) is treated with 1 ml 50% TFA in DCM for 1 hour at 25° C. The product is filtered off and the resin is washed with 1 ml DCM. The combined extracts are concentrated in vacuo. The residue is purified by chromatography and/or crystallisation to afford the compounds of the general formula (Ia) according to the invention.

The following preferred compounds are within the scope of the present invention and may be prepared according to the general procedures disclosed above.

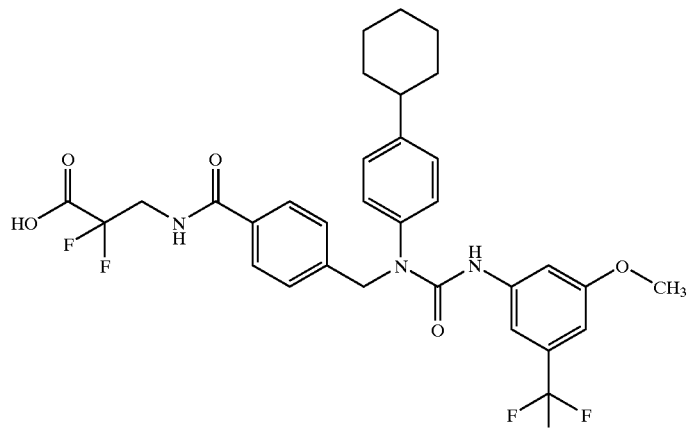

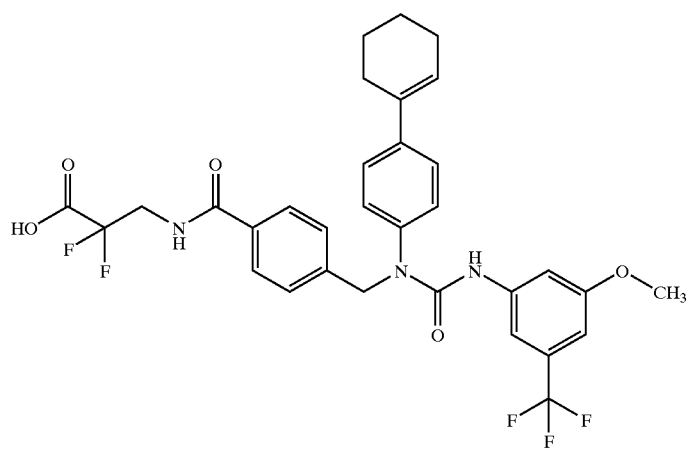

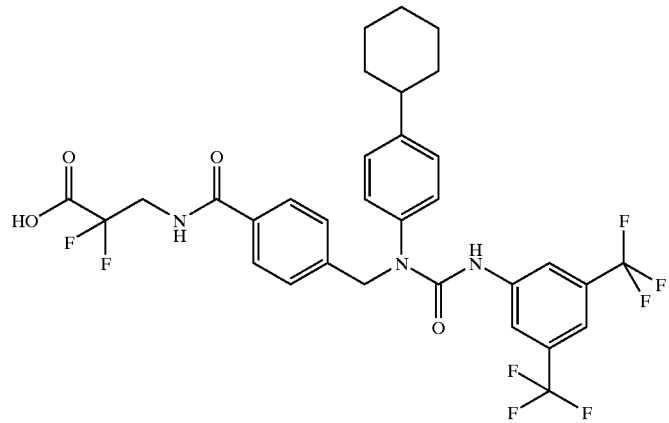
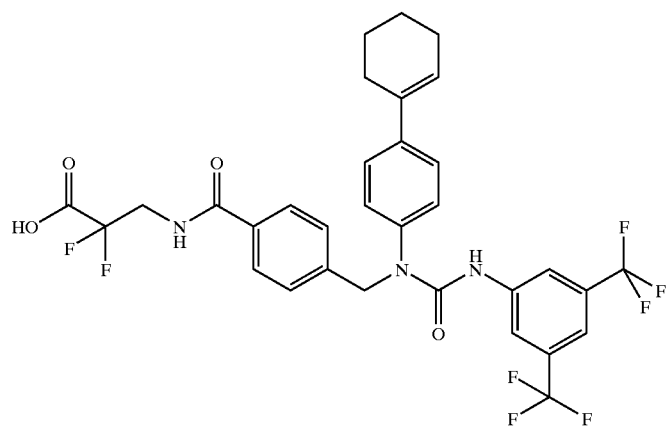
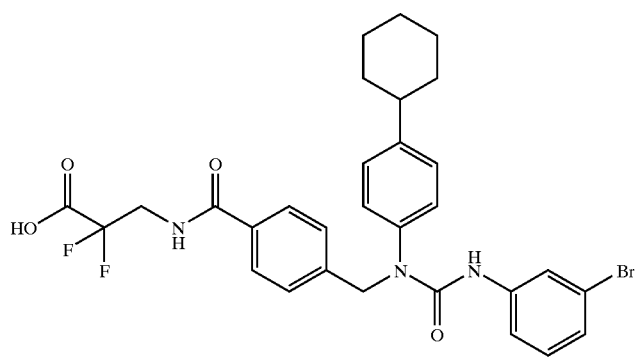
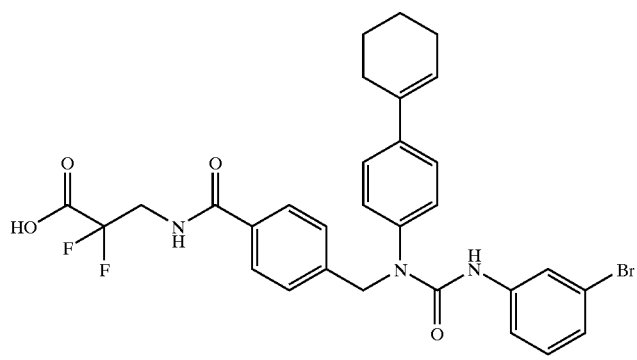

-continued
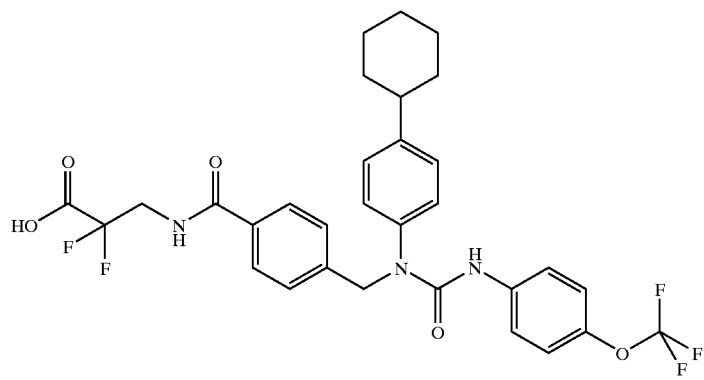
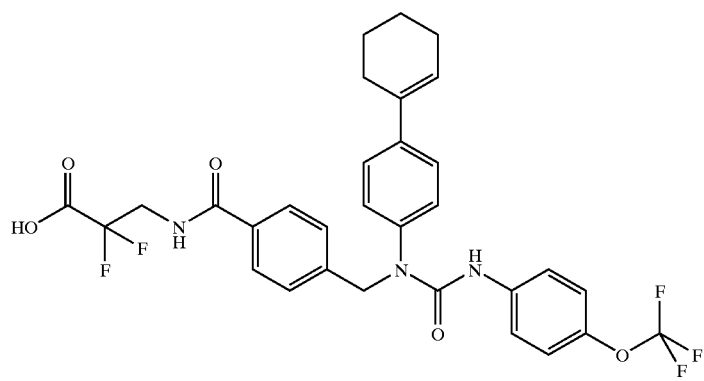
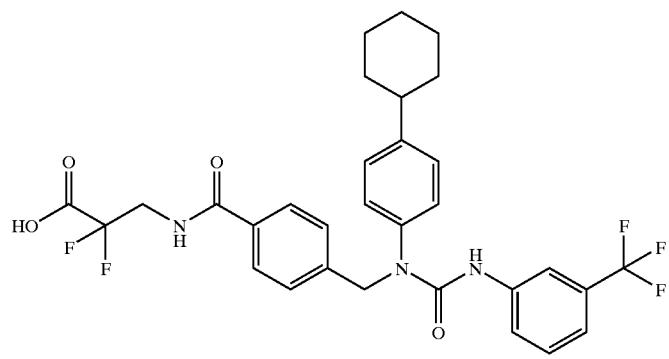
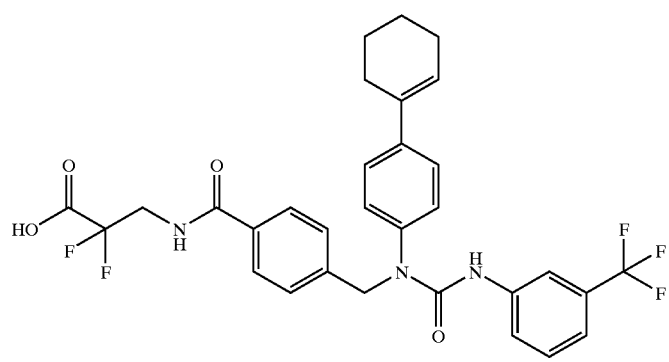

-continued
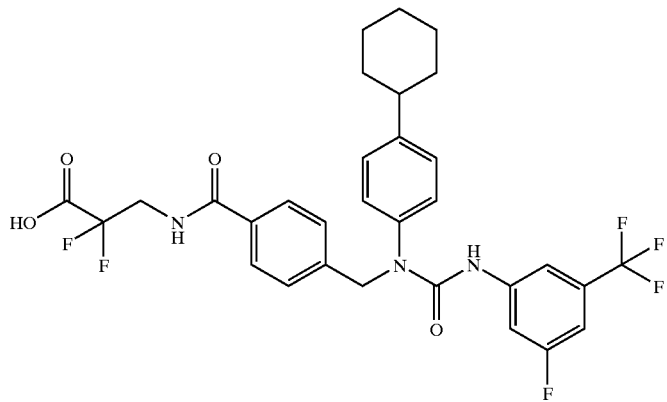
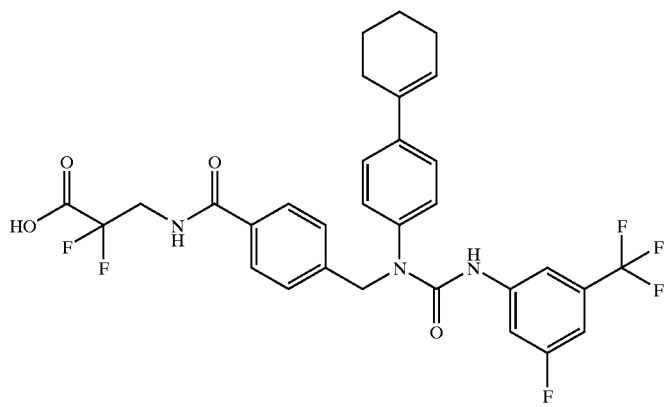
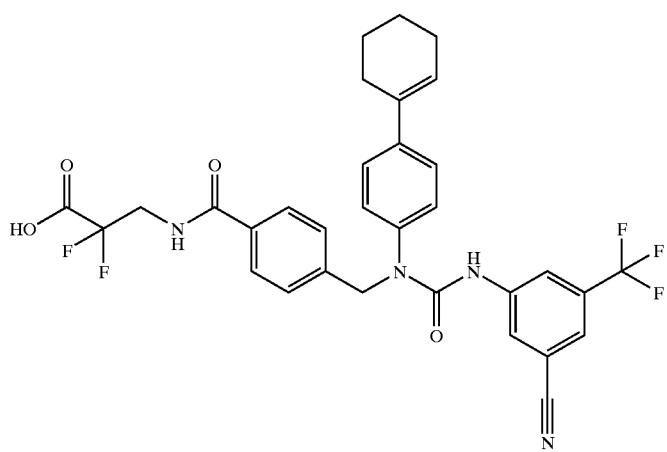

-continued
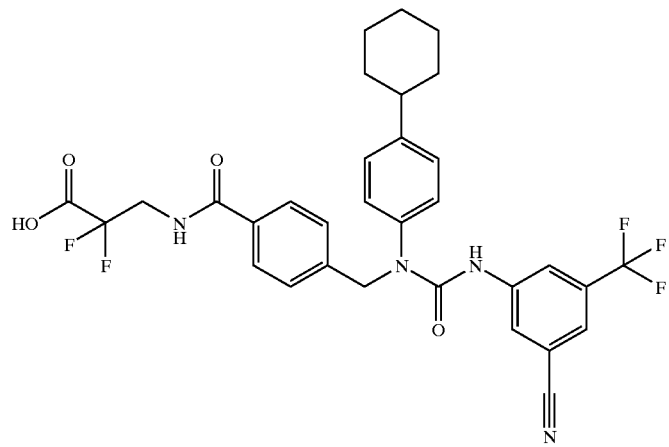
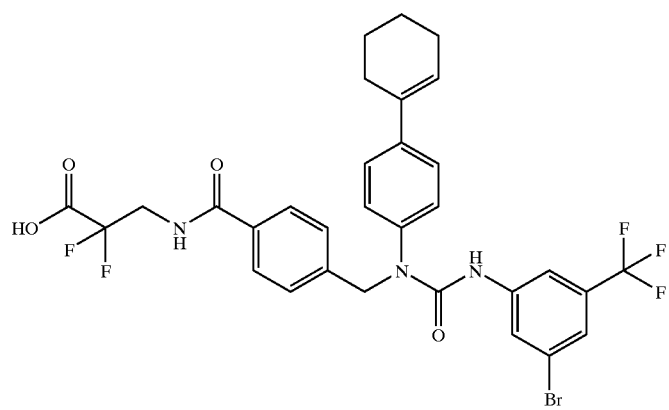
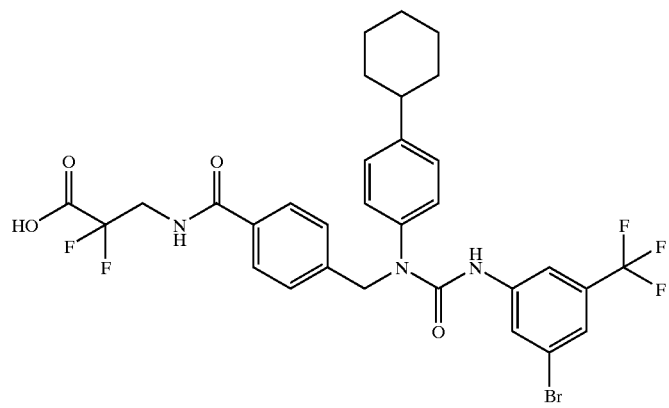
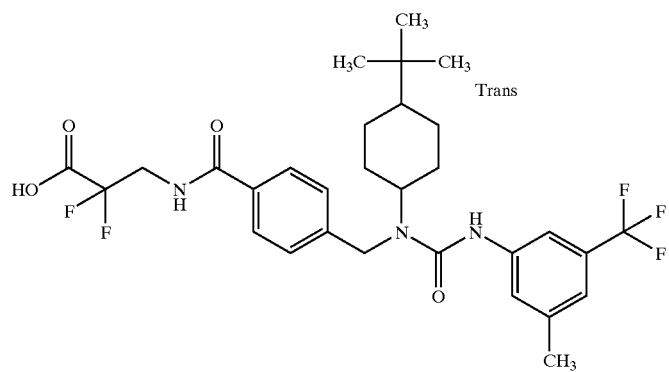

-continued
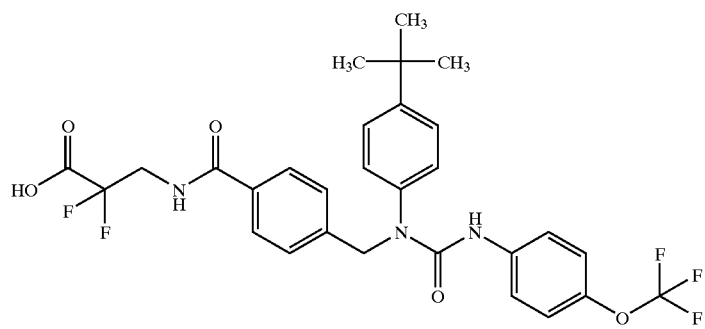
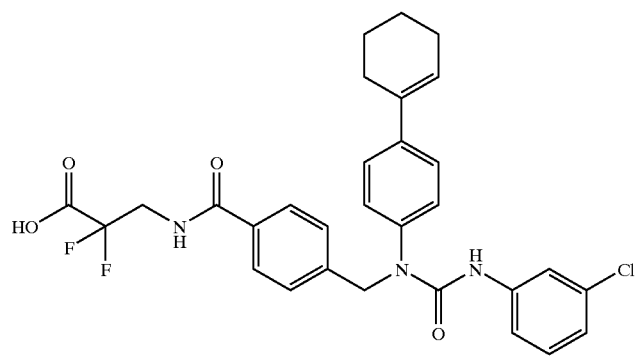
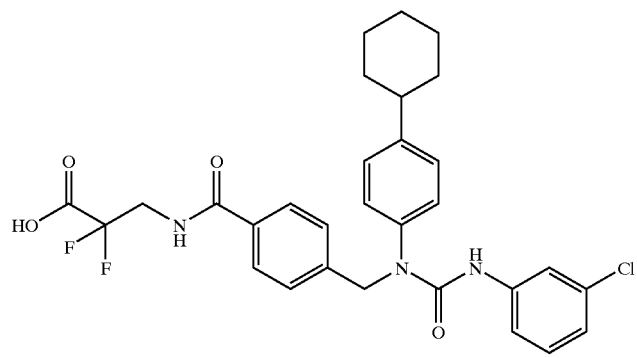
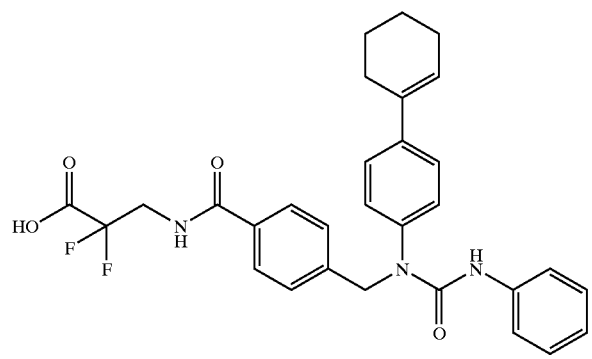

-continued
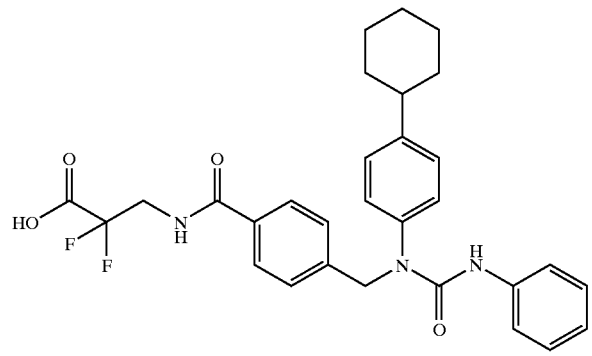
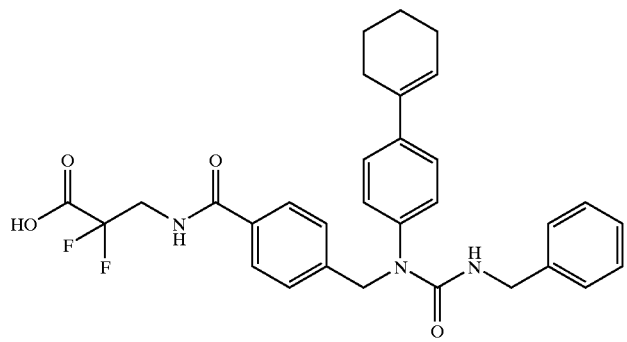
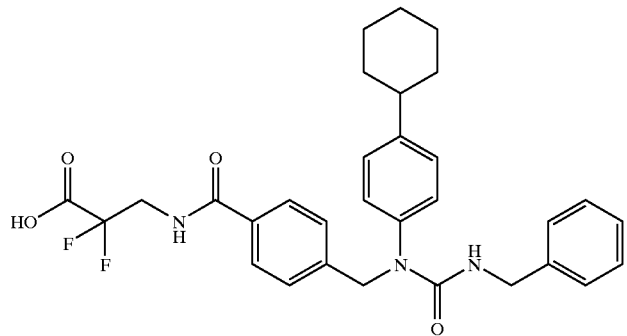
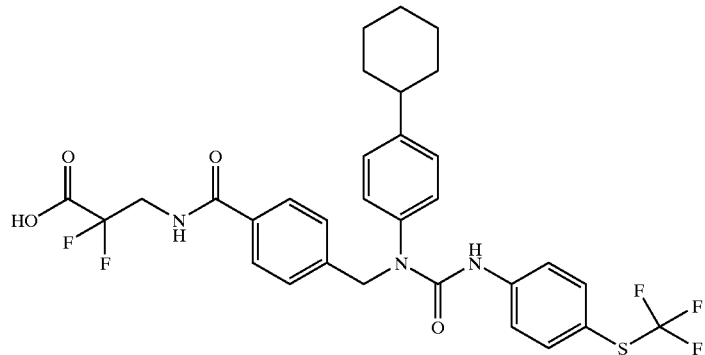

-continued
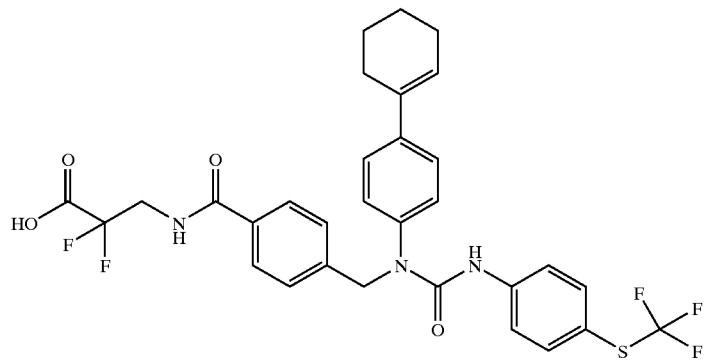
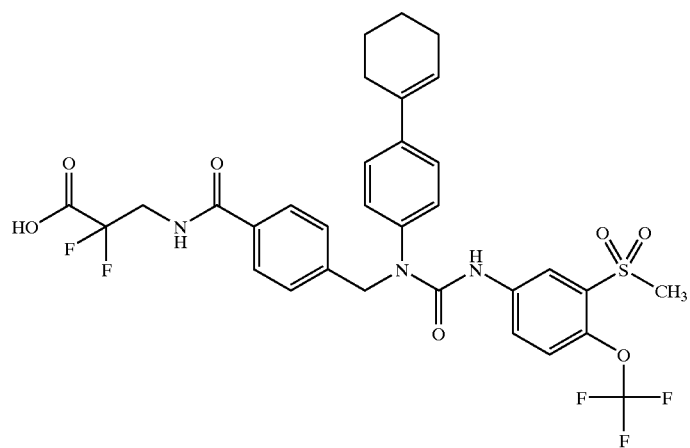
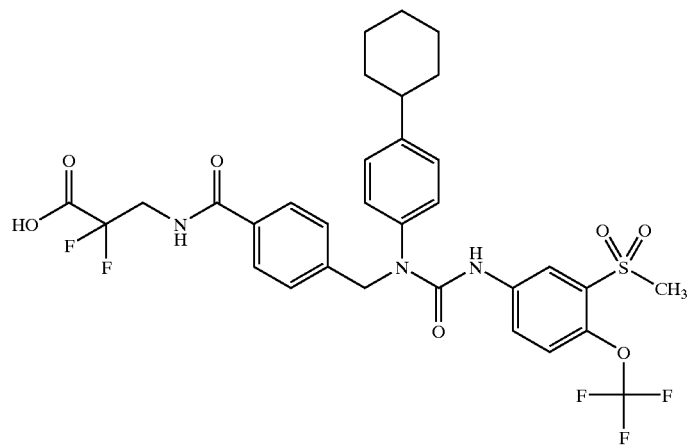
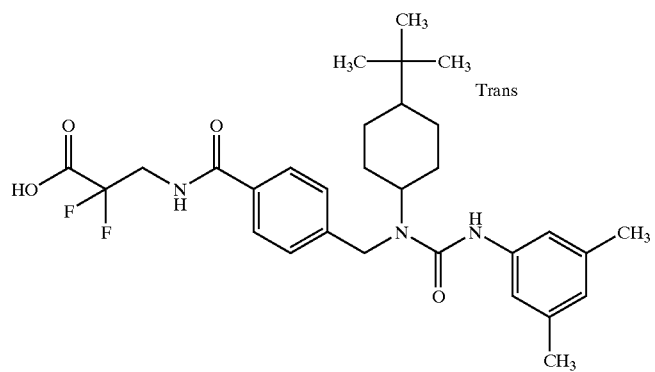

-continued
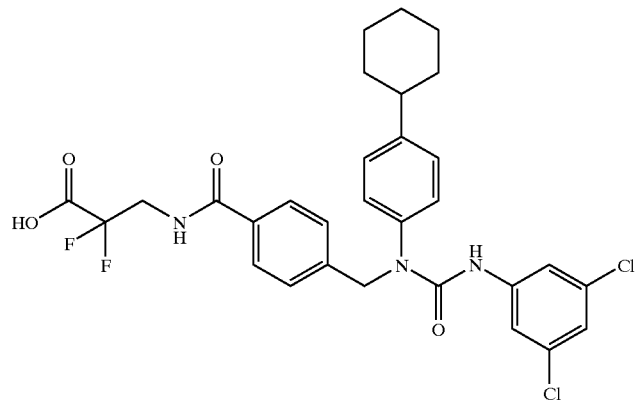
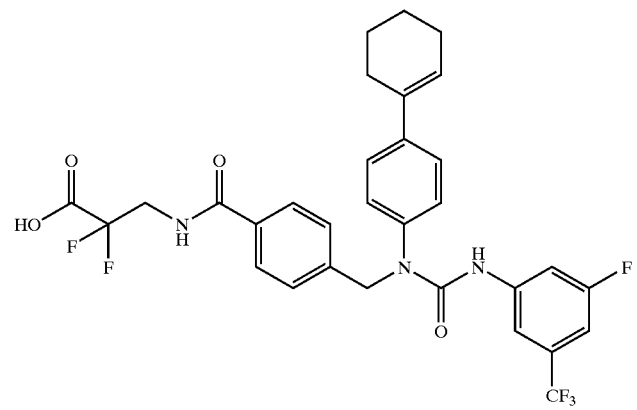
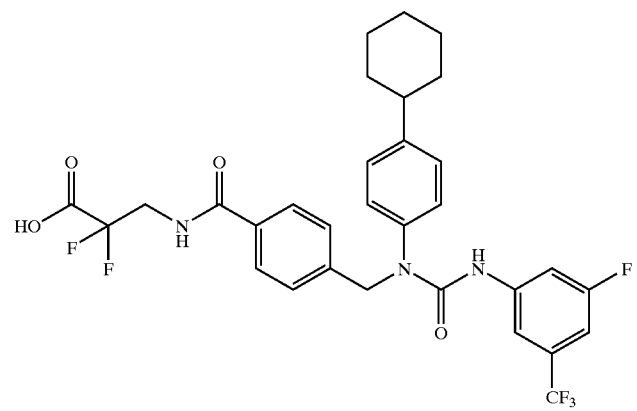
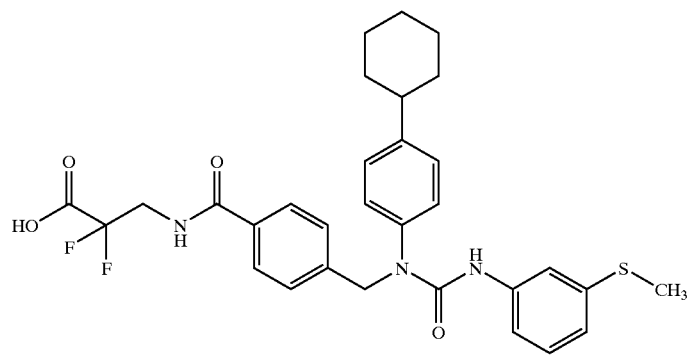

-continued
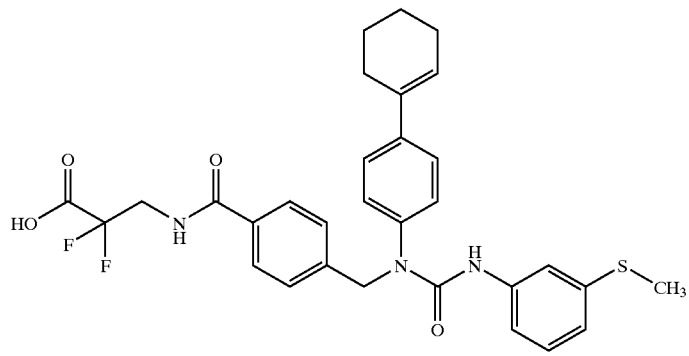
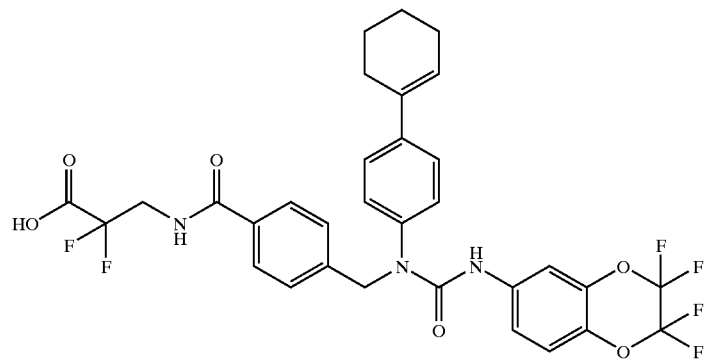
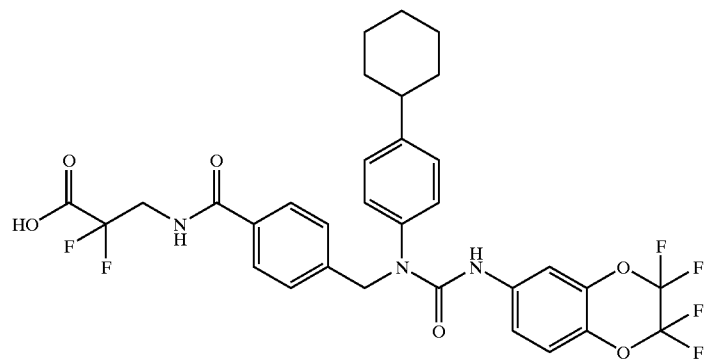
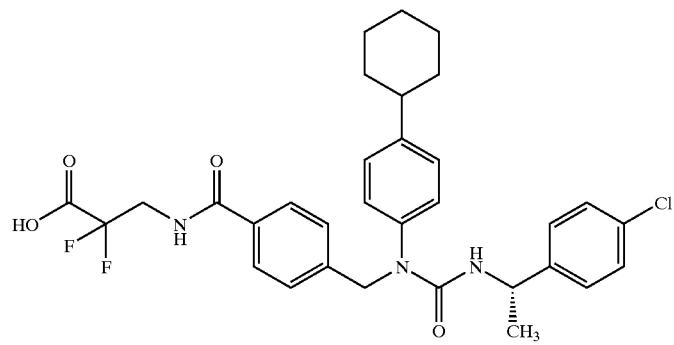

-continued
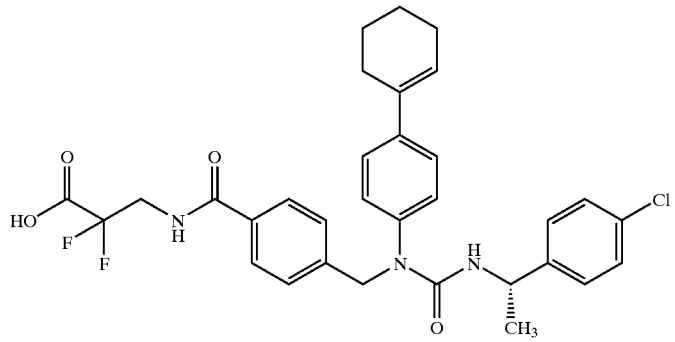
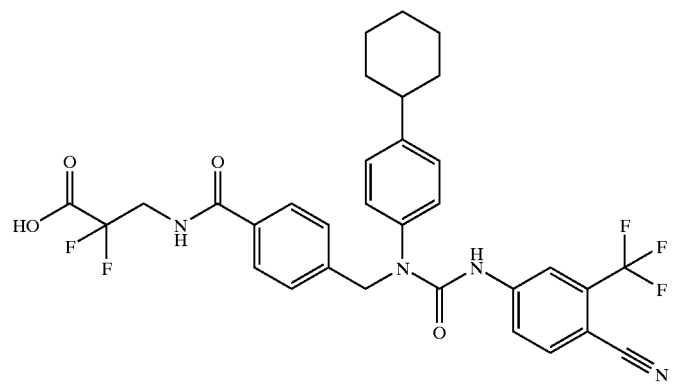
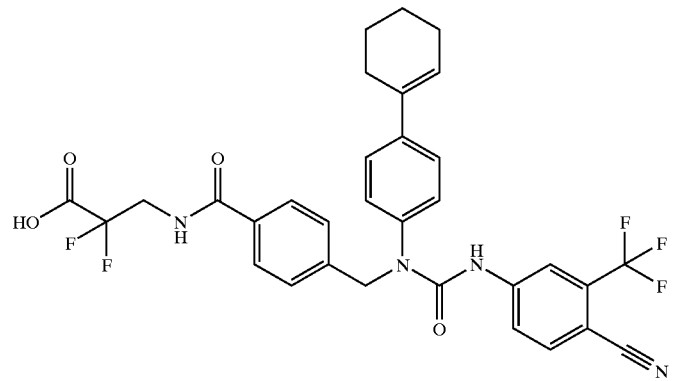
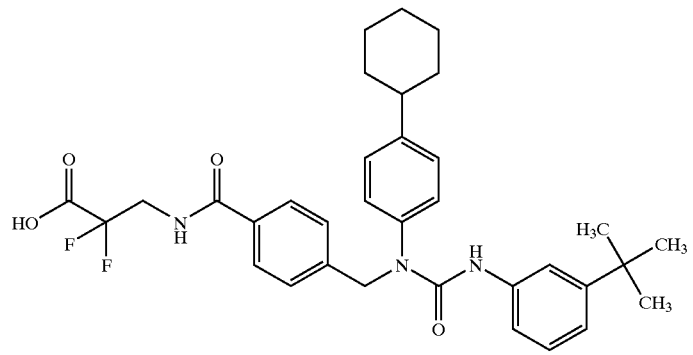

-continued
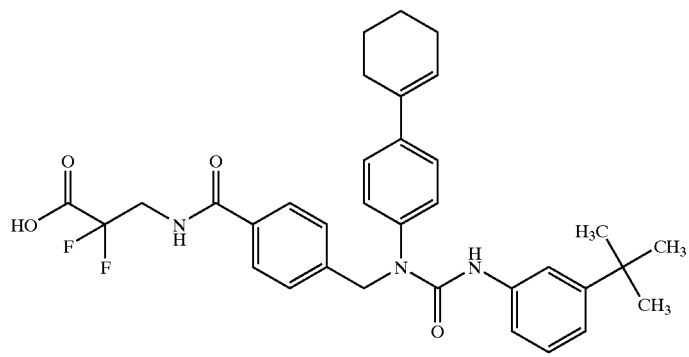
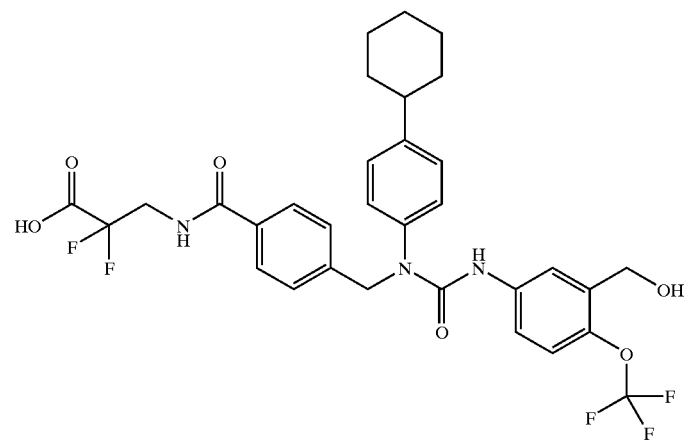
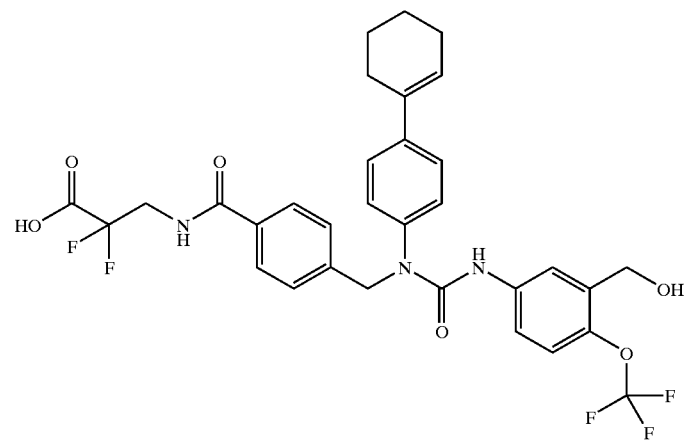
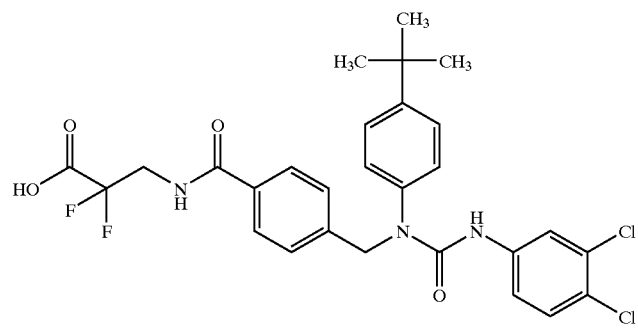

-continued
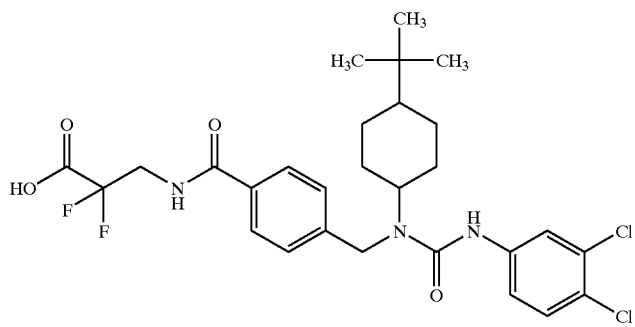
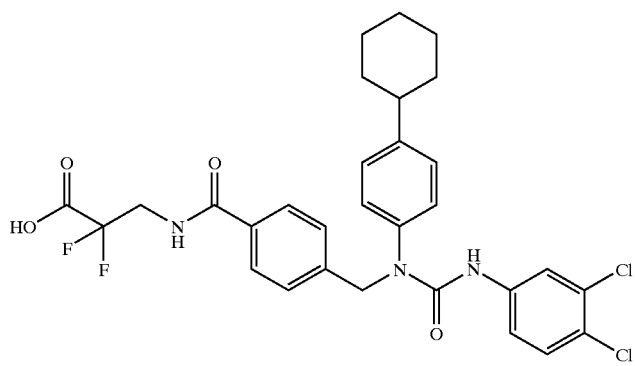
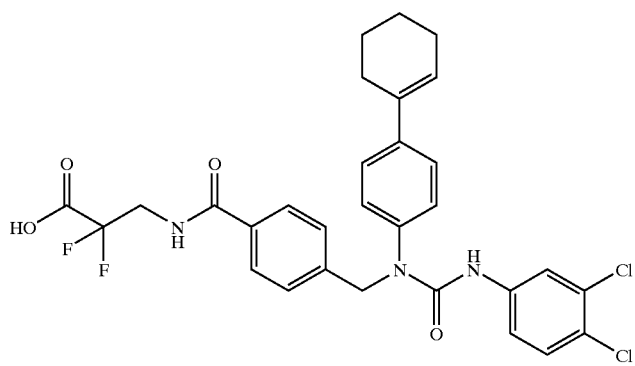
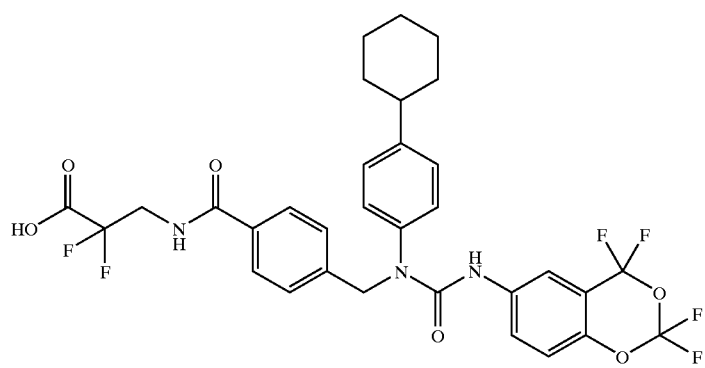

-continued
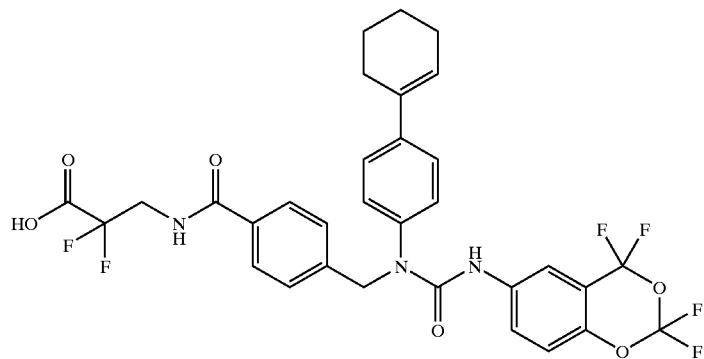
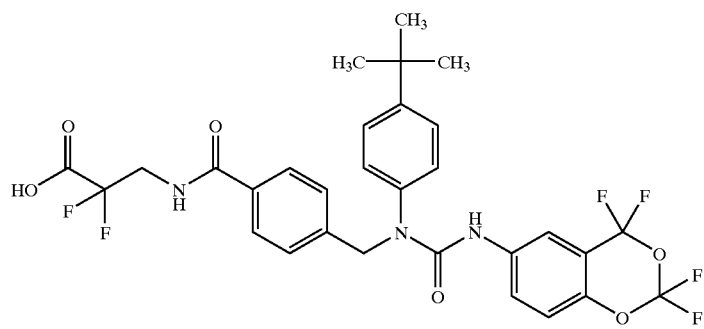
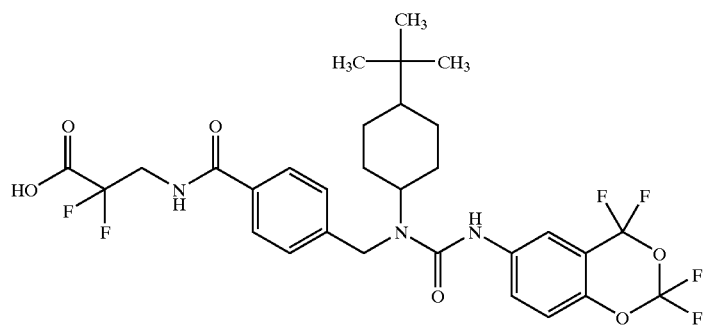
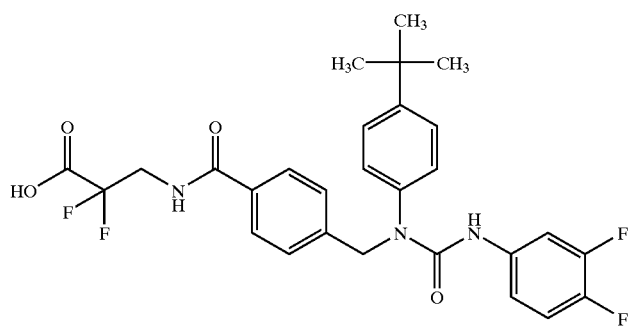

-continued
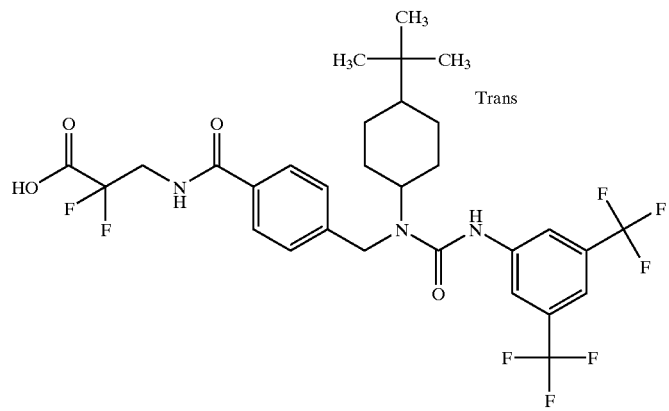
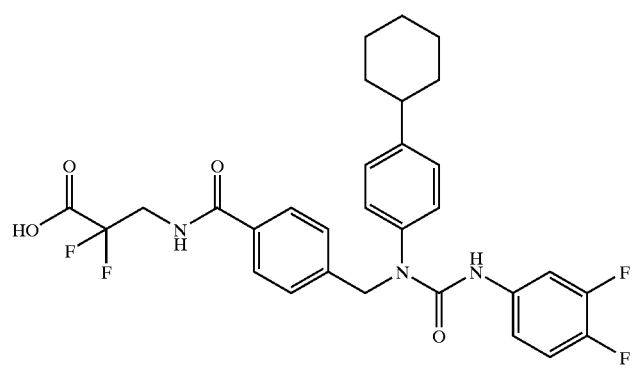
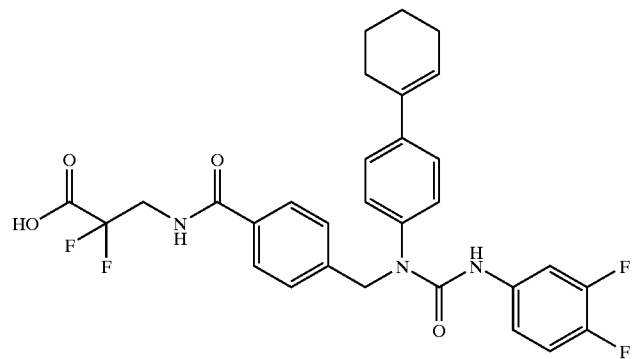
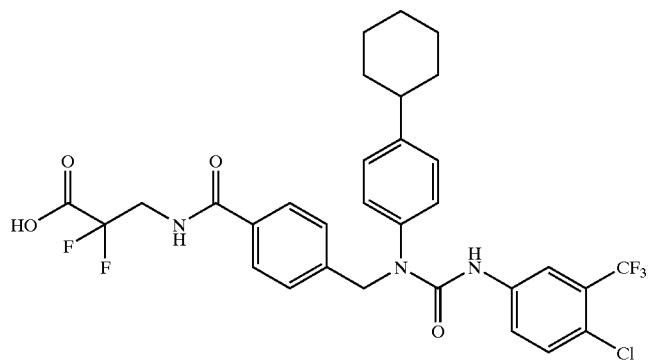

-continued
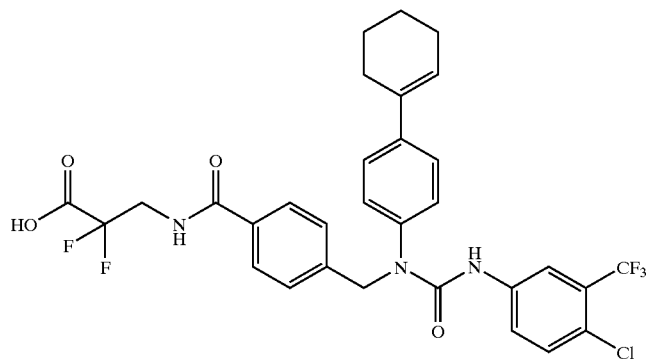
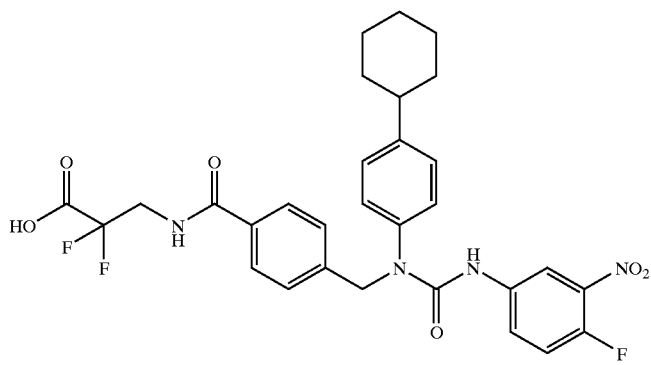
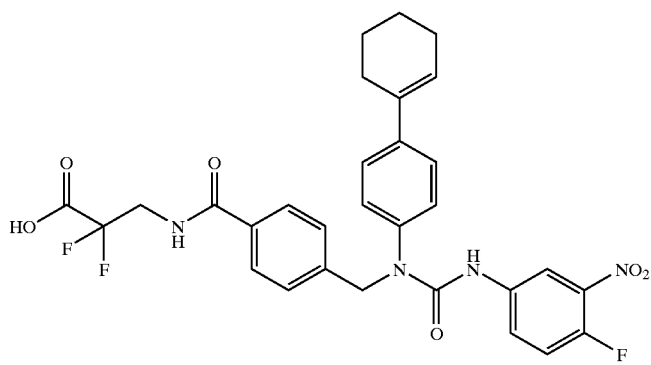
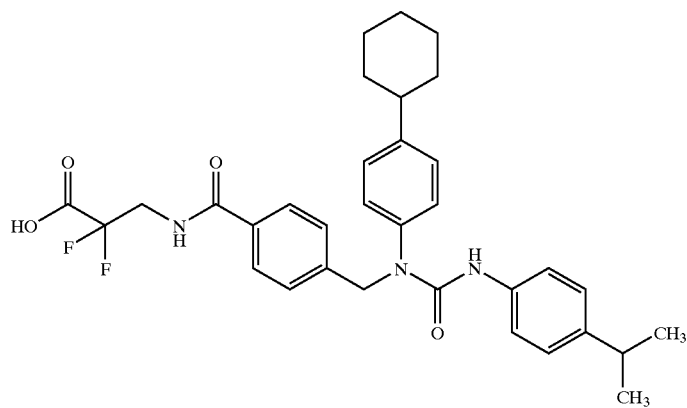

-continued
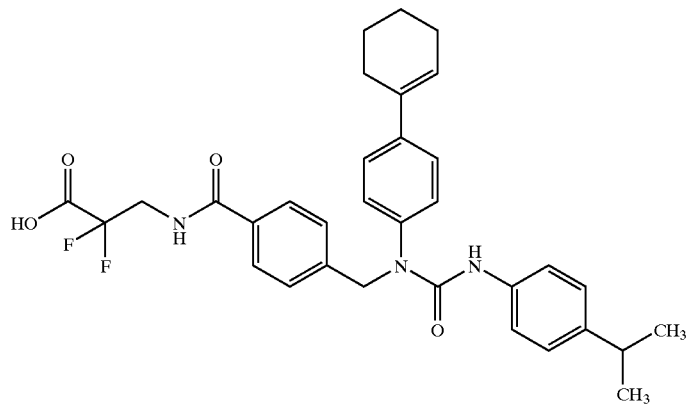
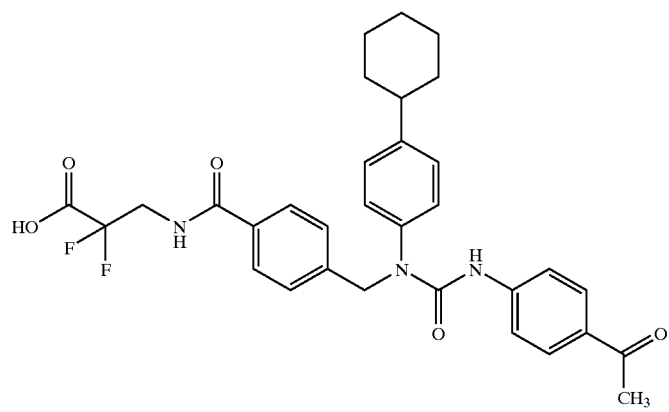
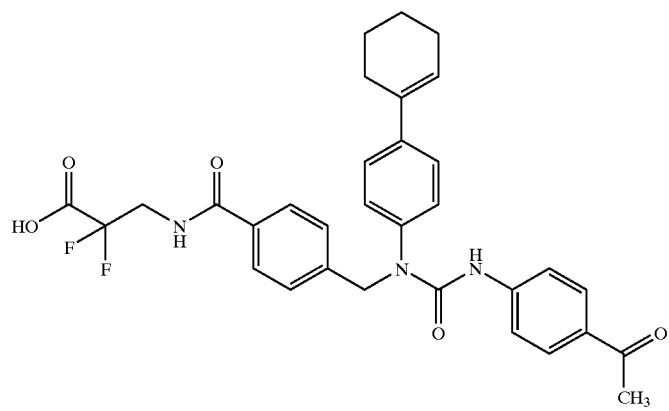
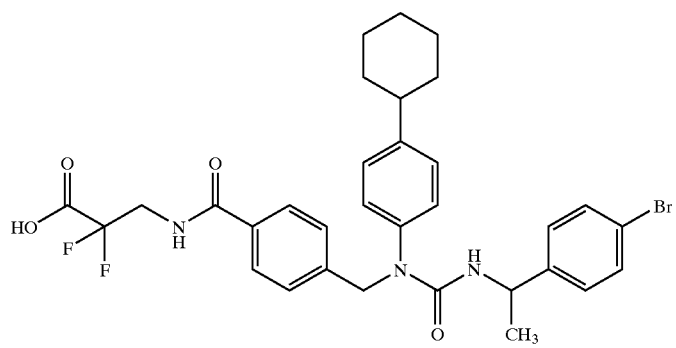

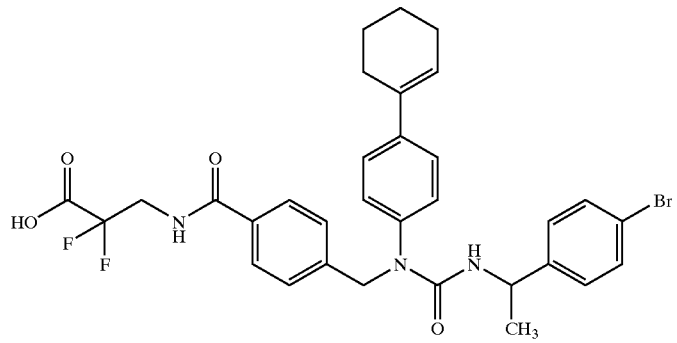
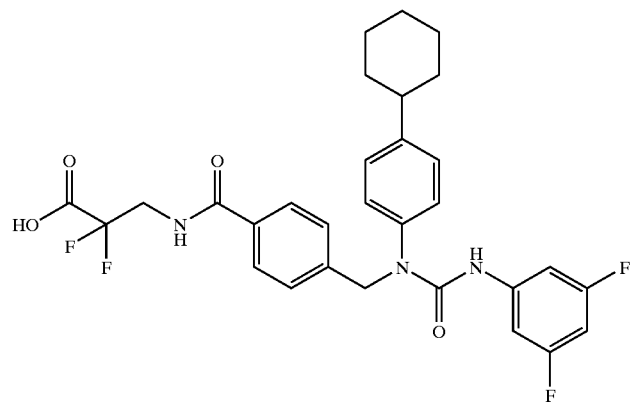
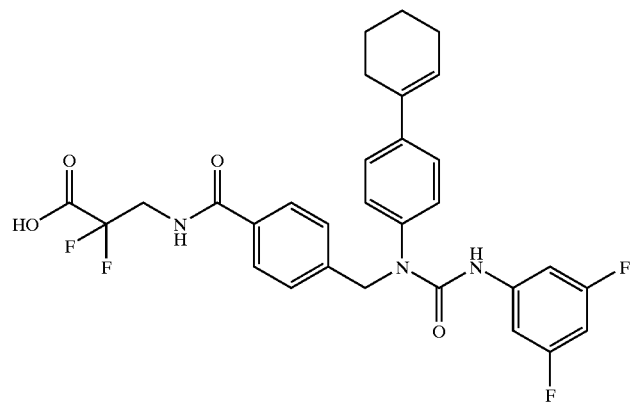
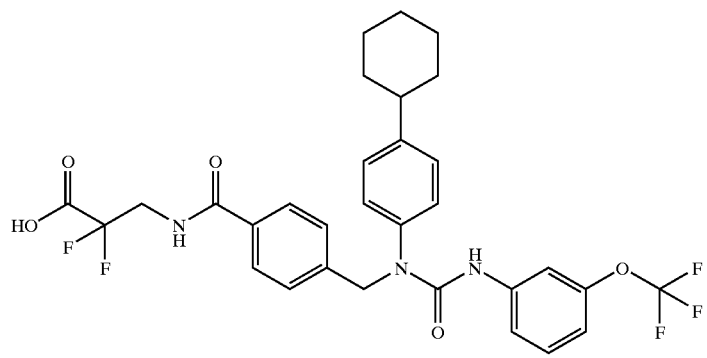

-continued
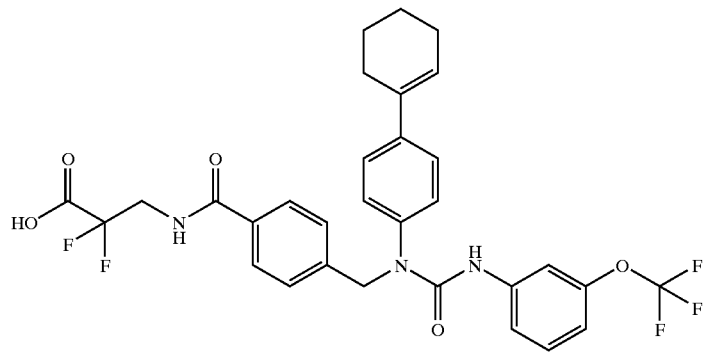
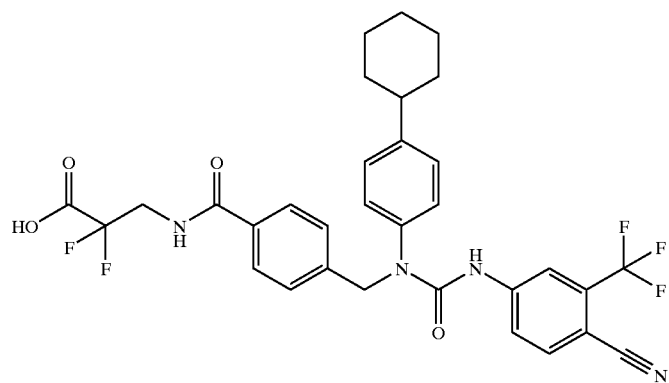
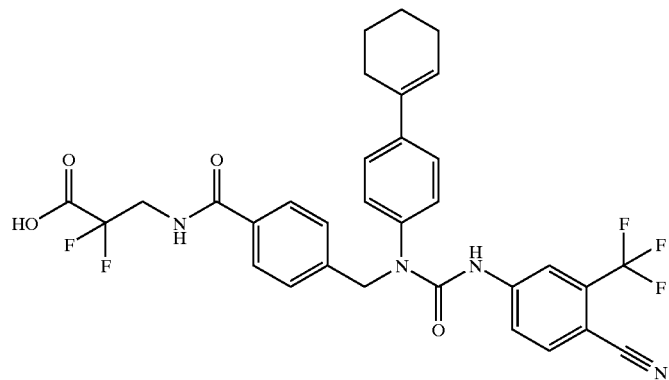
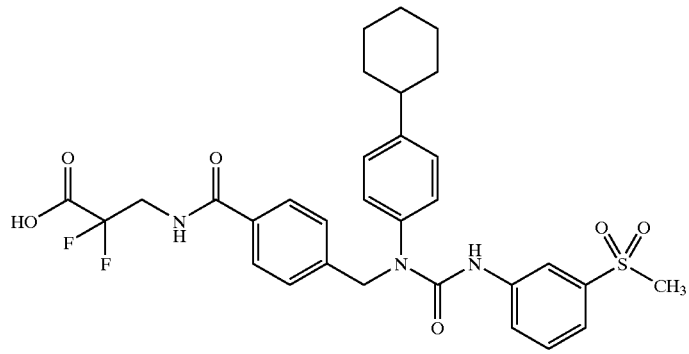

-continued
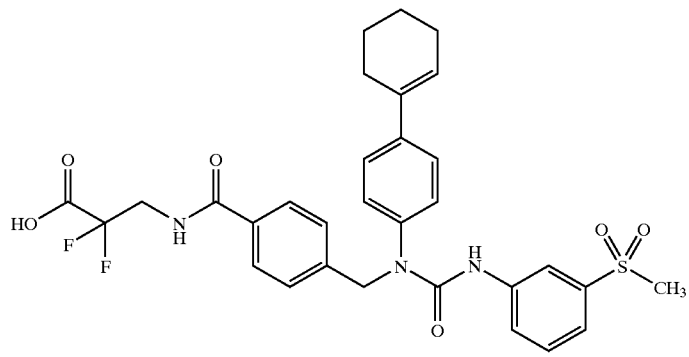
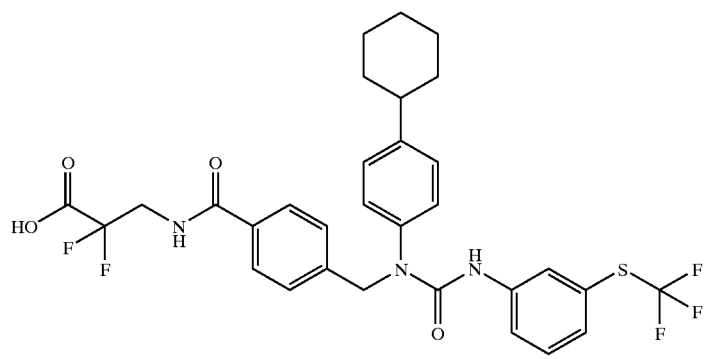
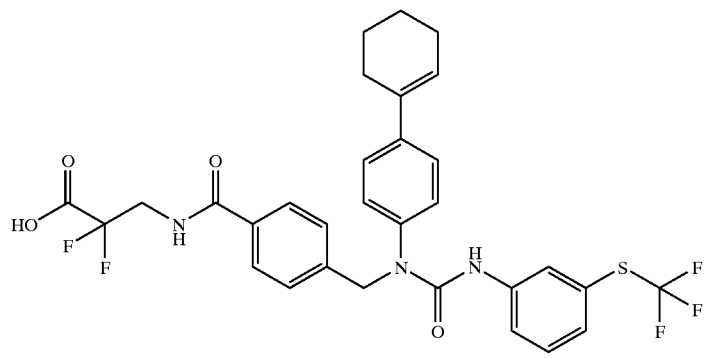
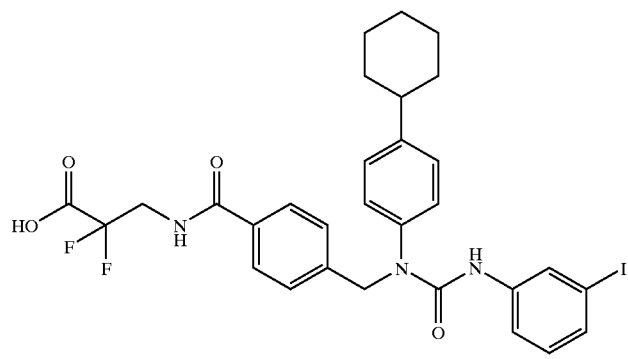

-continued
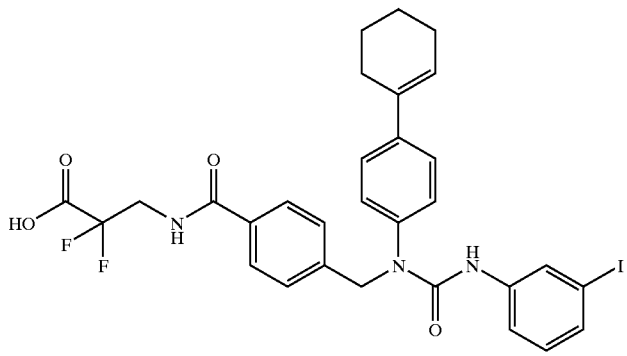
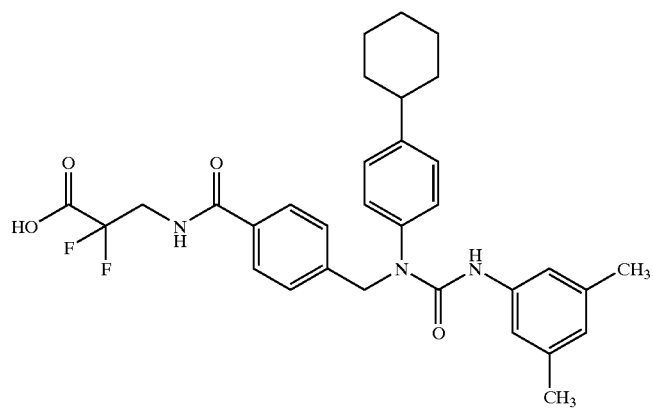
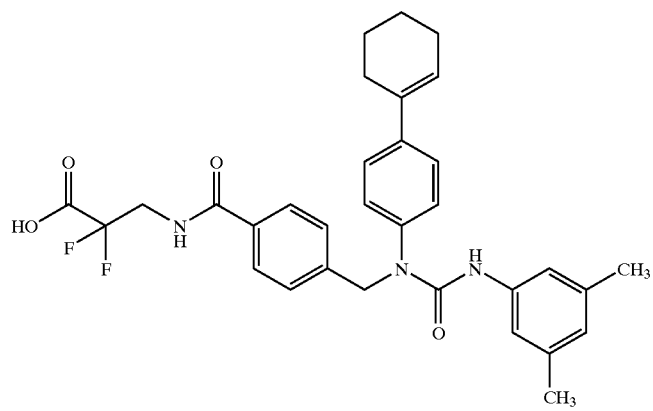
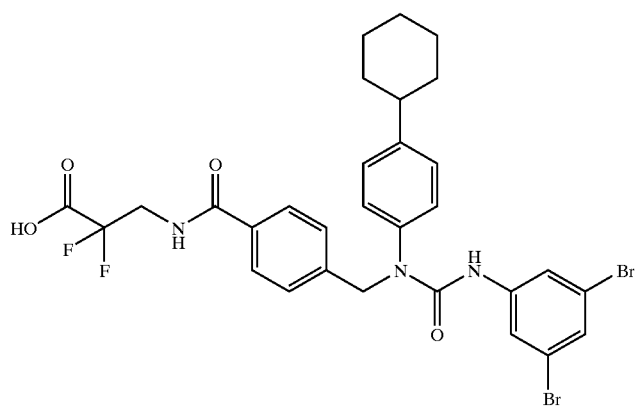

-continued
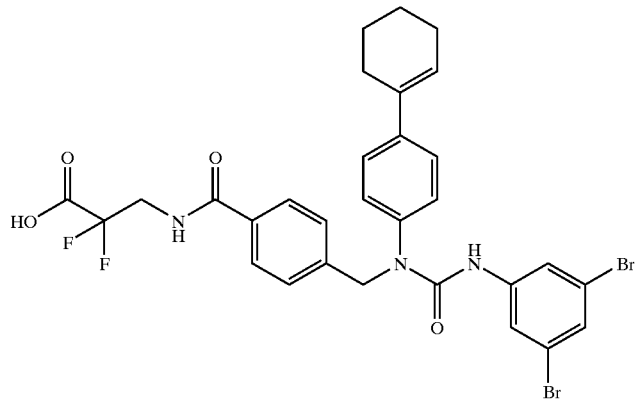
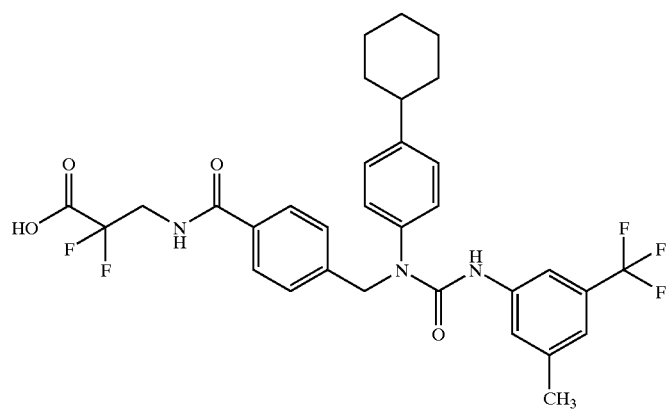
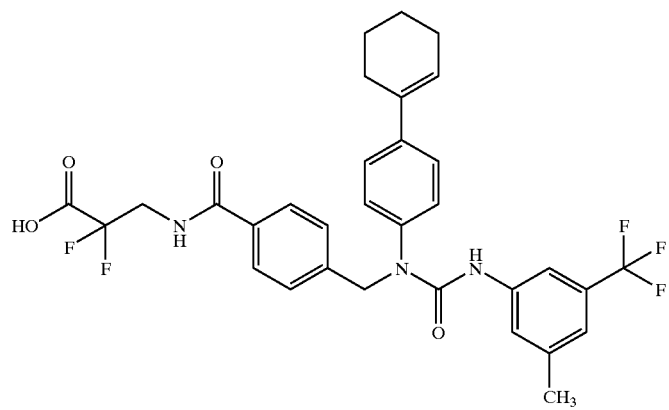
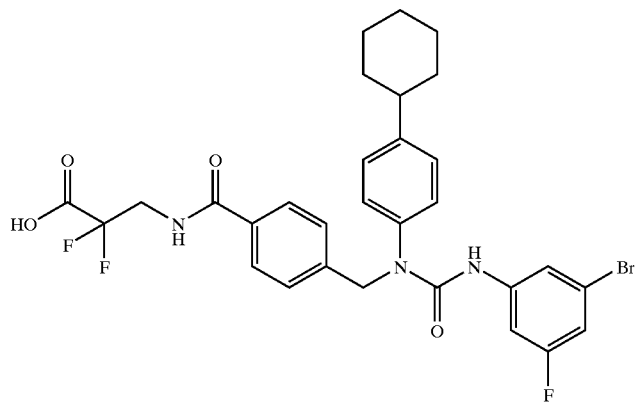

-continued
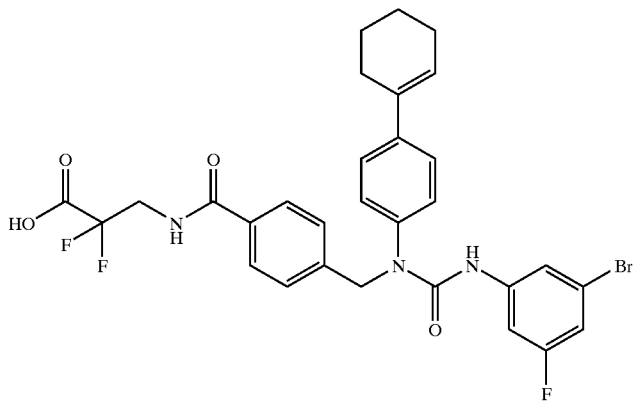
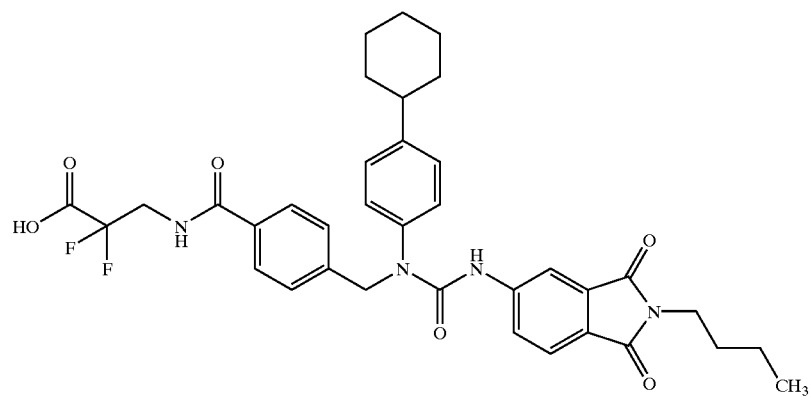
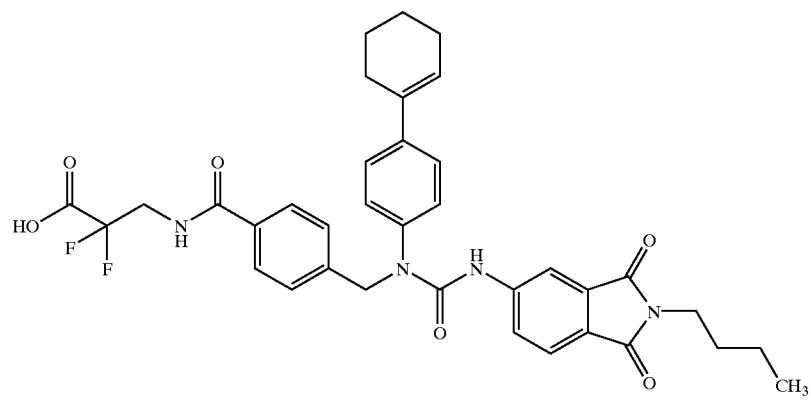
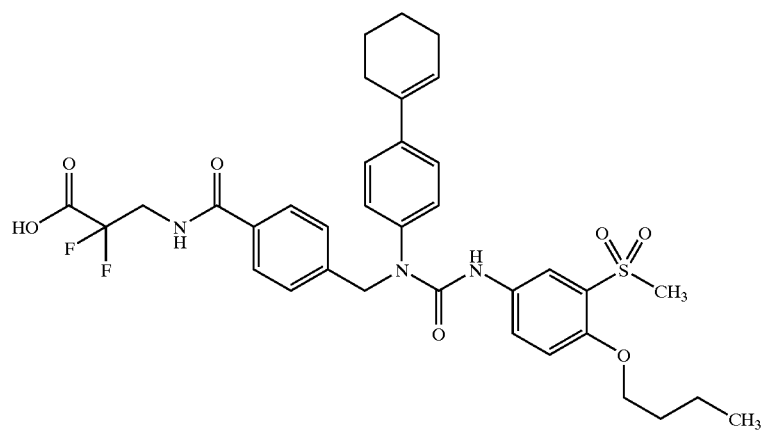

-continued
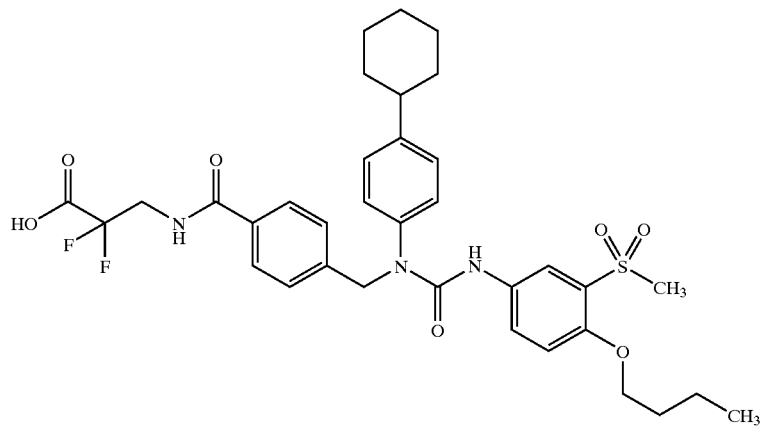
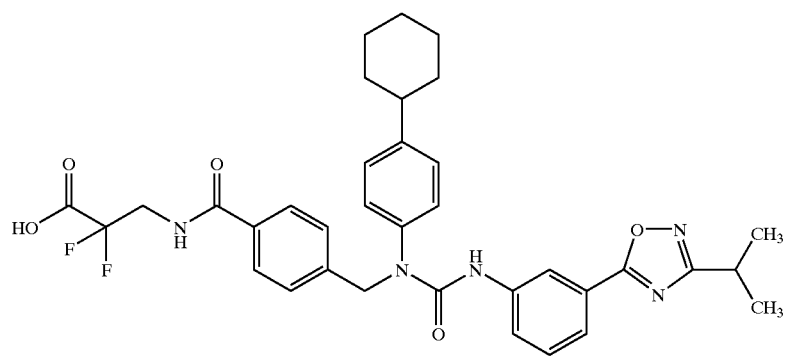
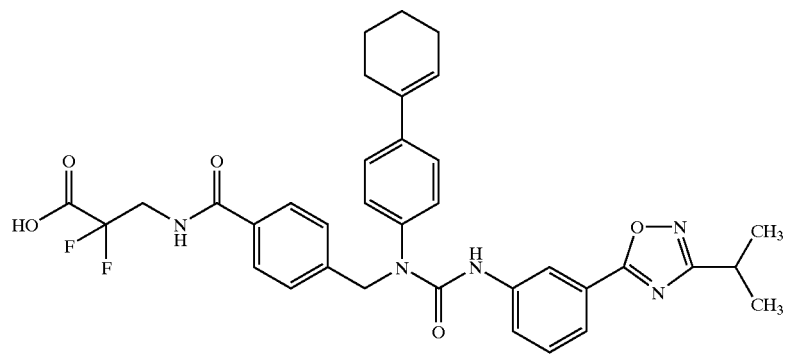
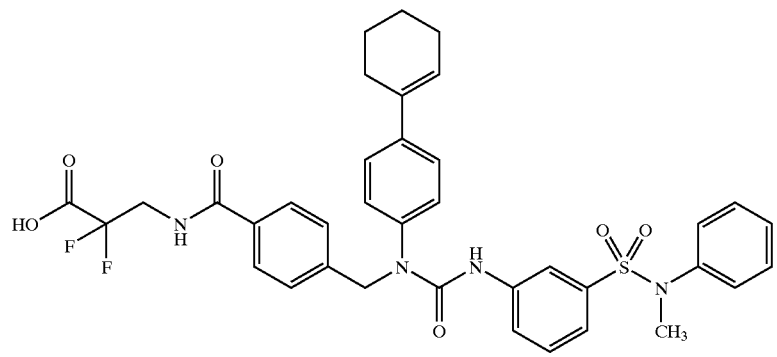

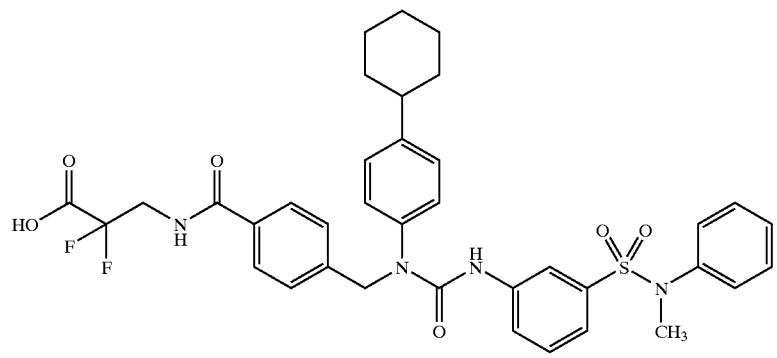
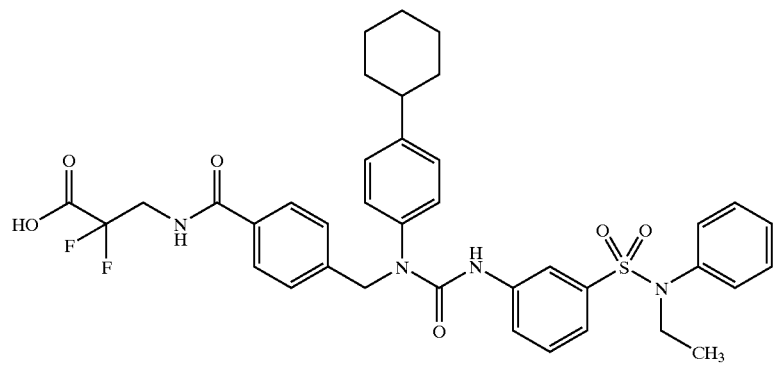
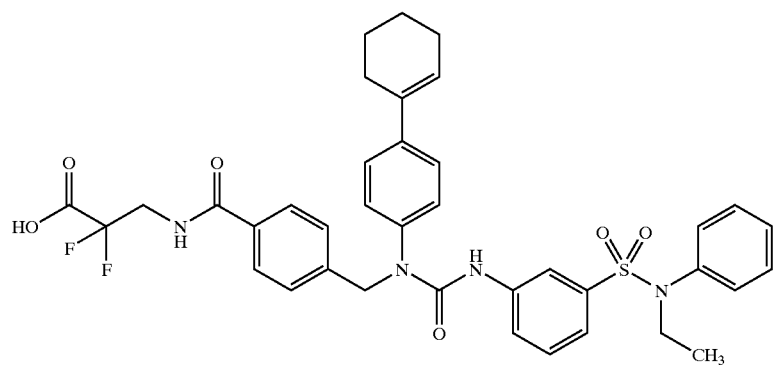
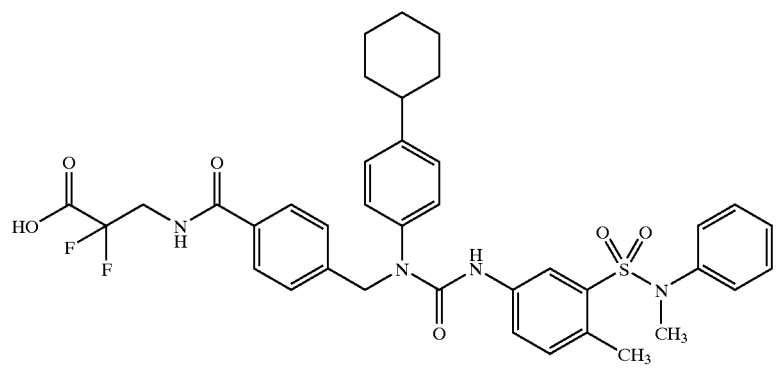

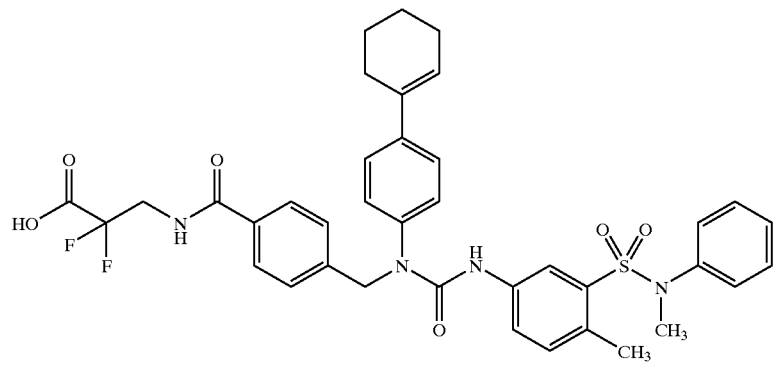
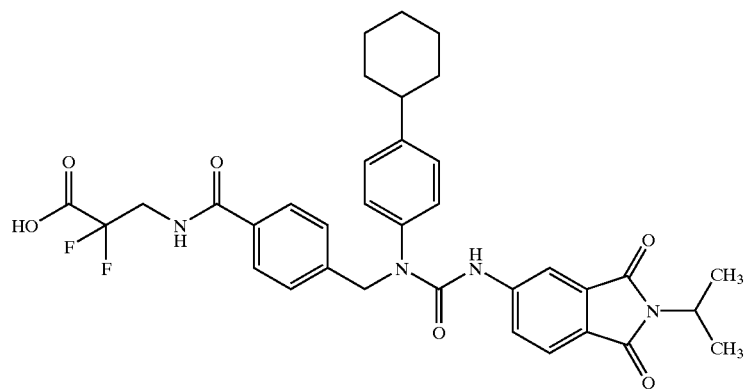
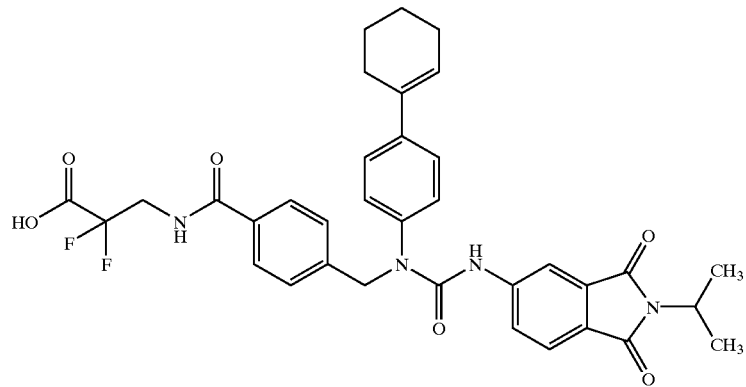
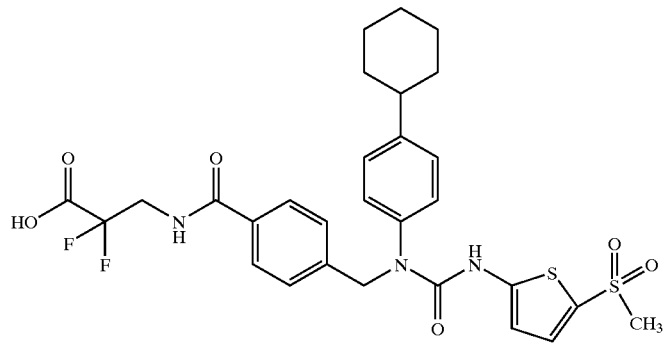

-continued
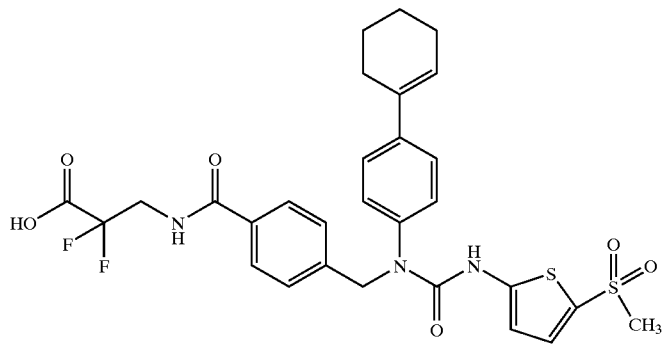
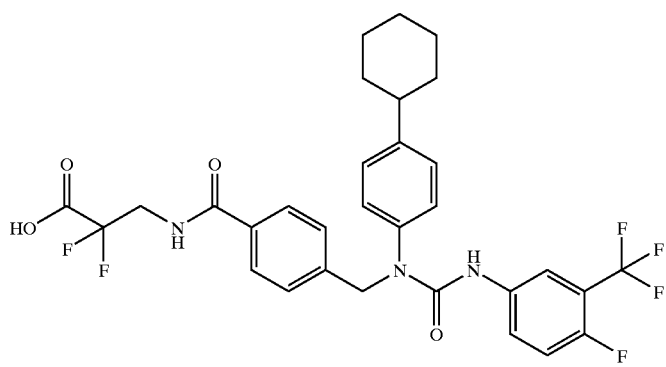
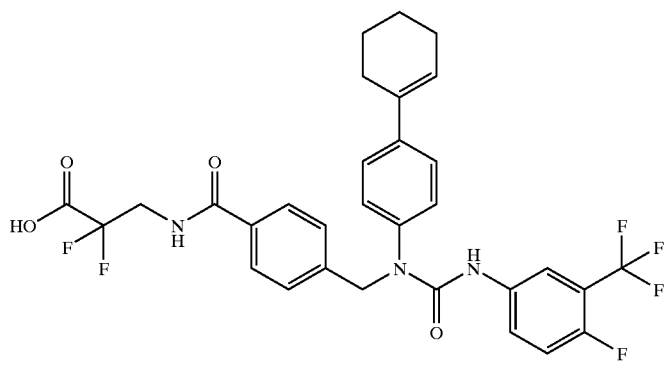
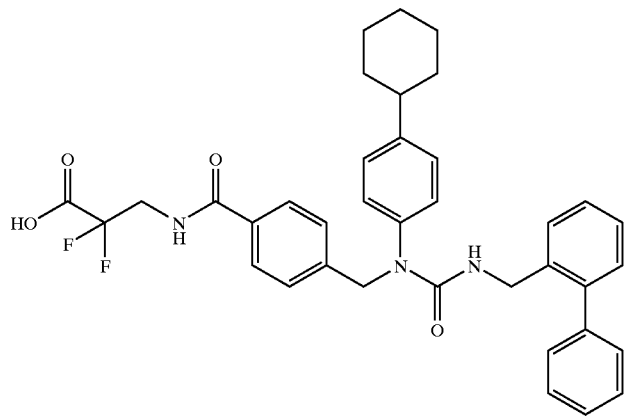

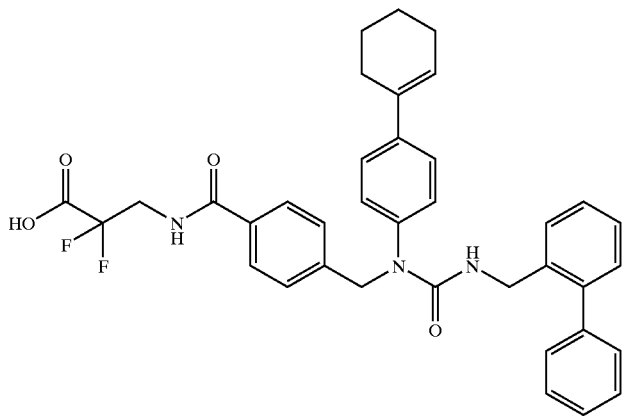
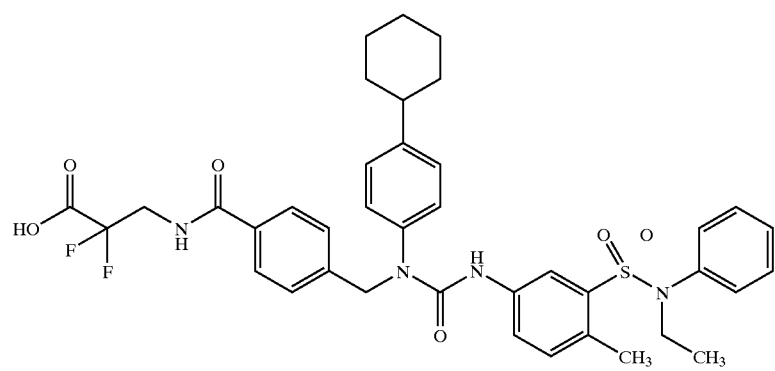
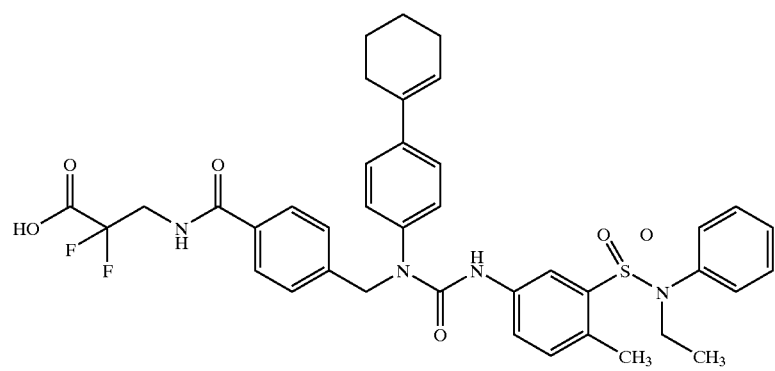
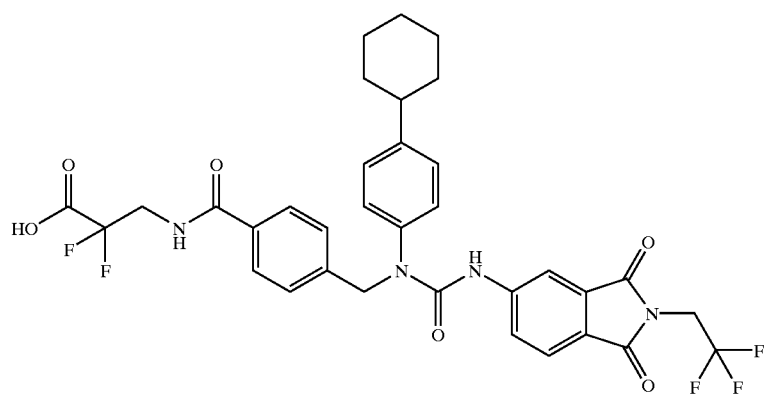

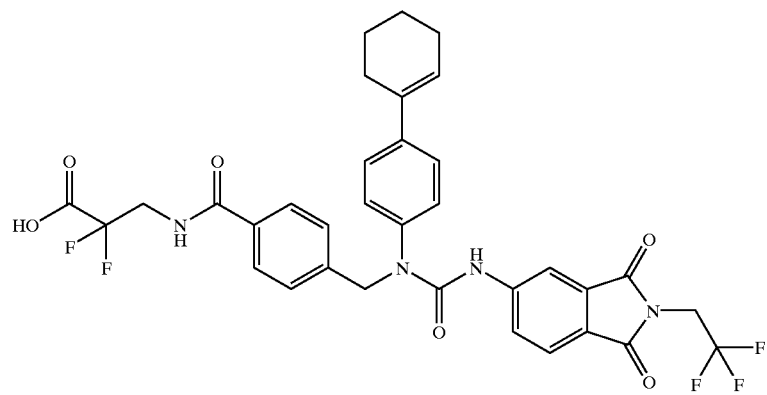
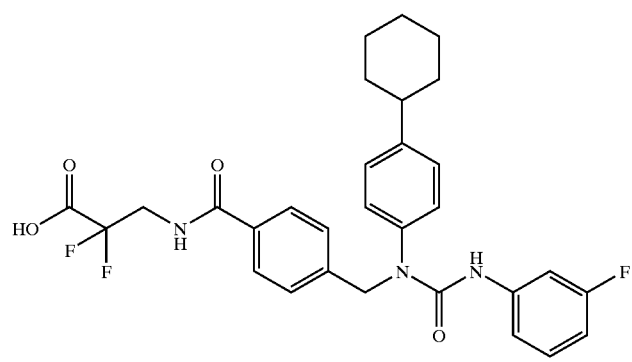
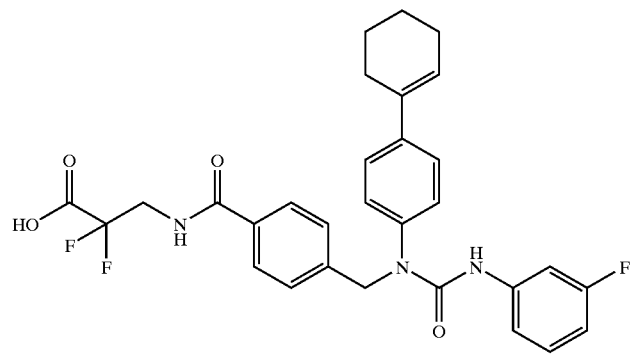
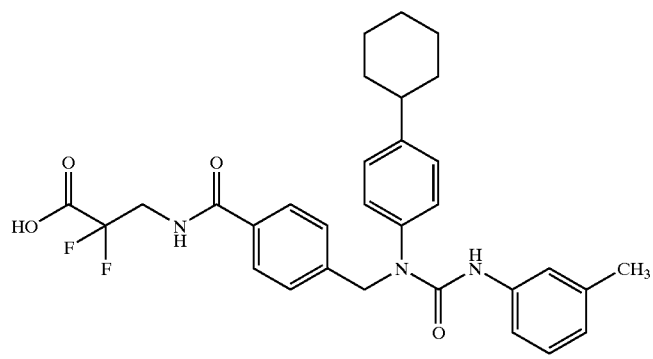

-continued
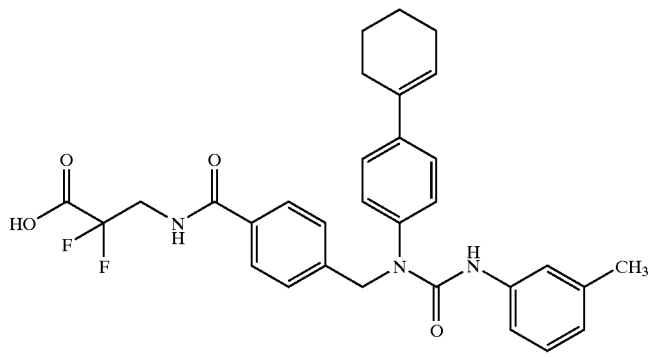
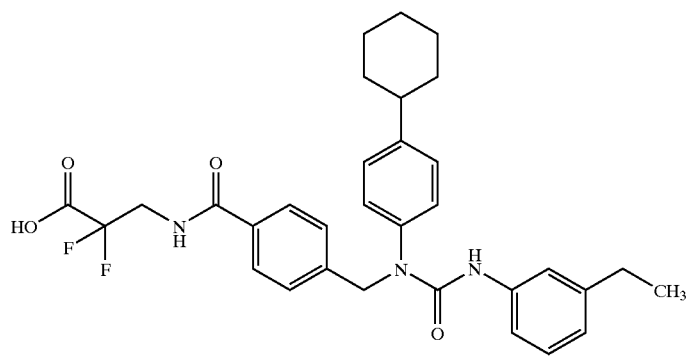
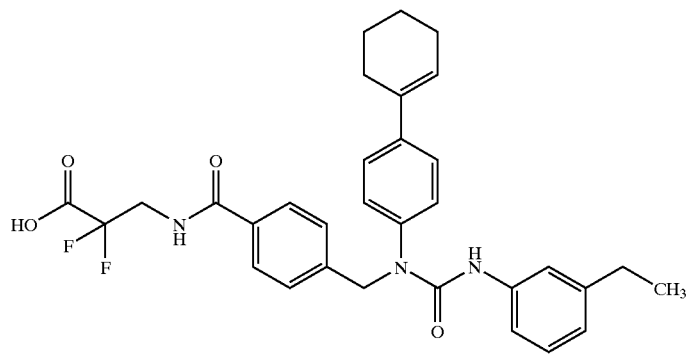
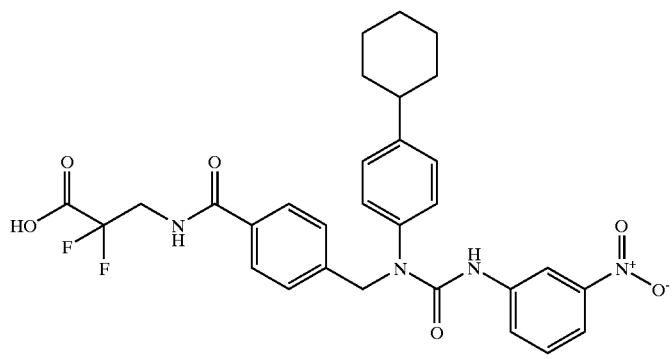

-continued
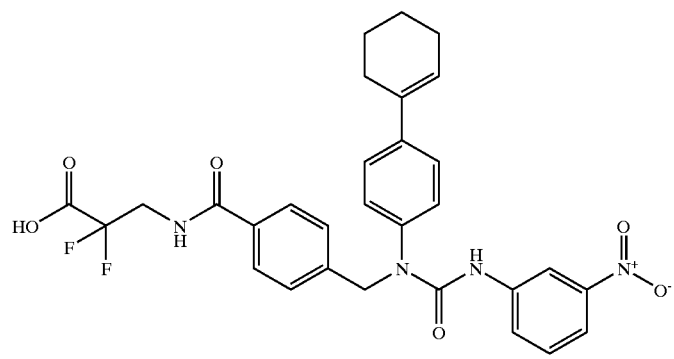
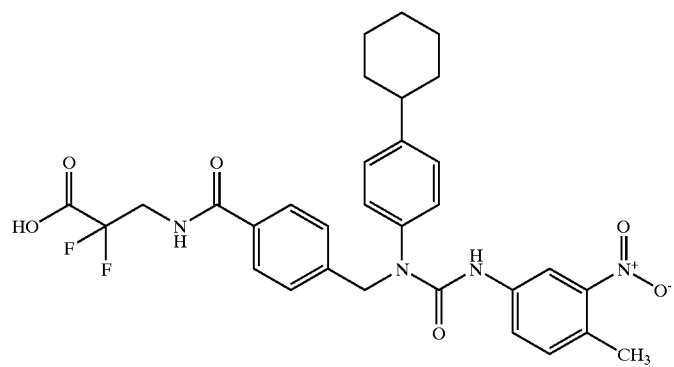
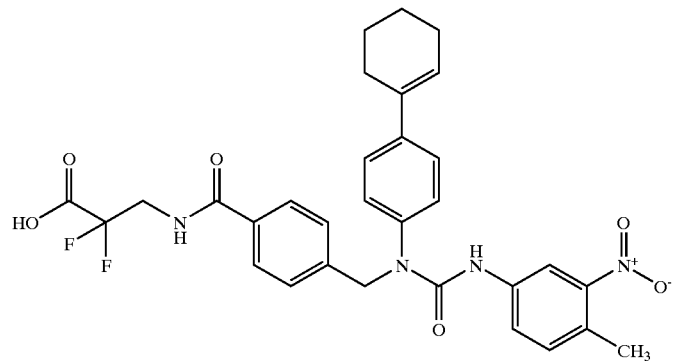
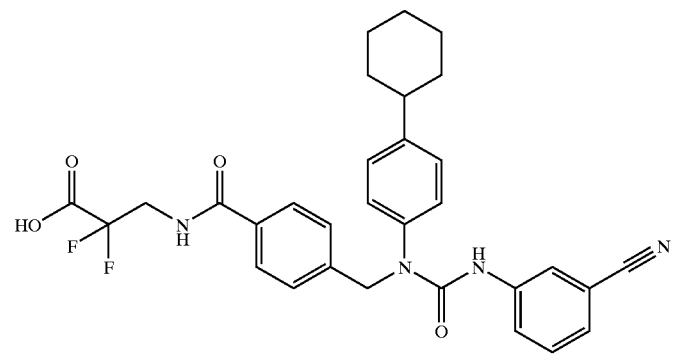

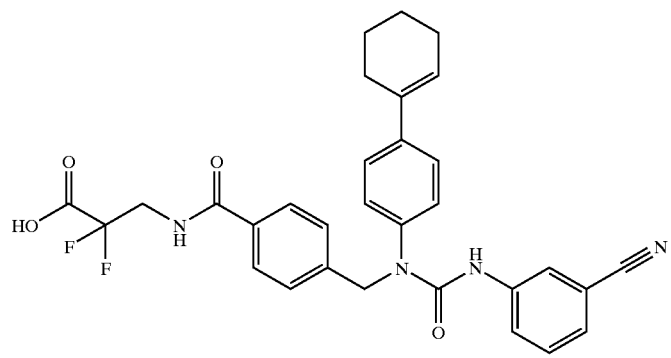
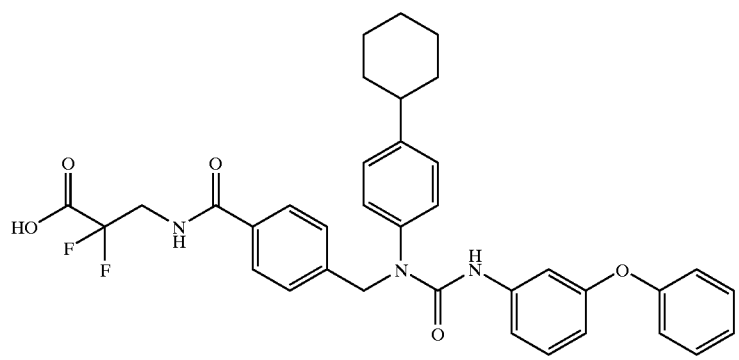
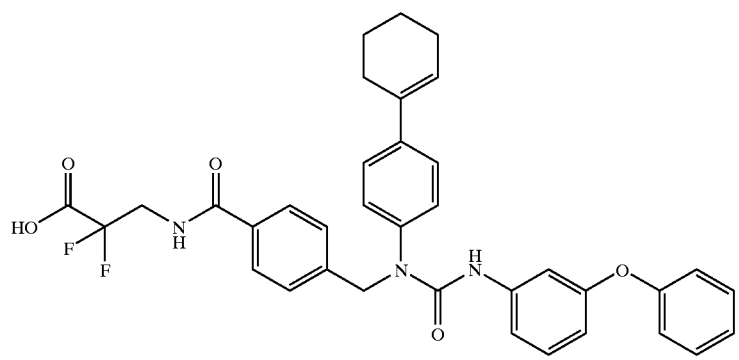
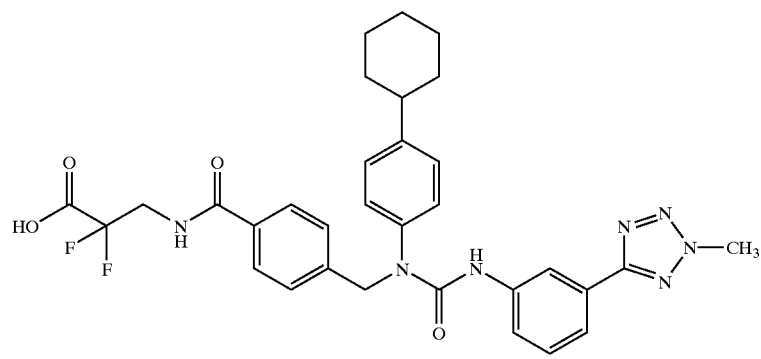

-continued
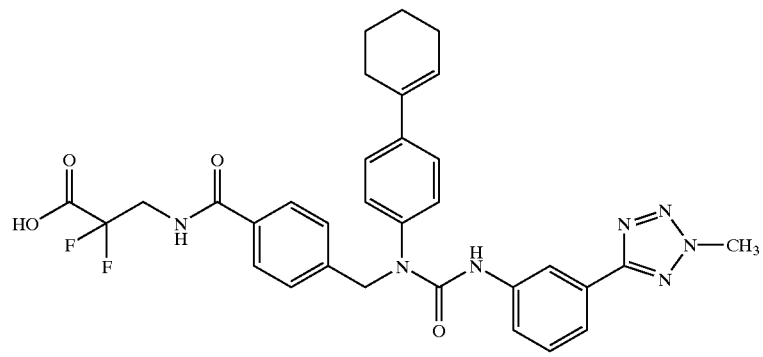
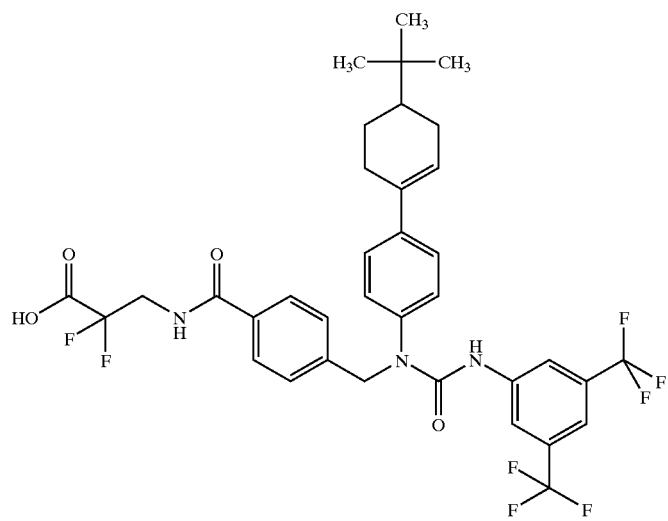
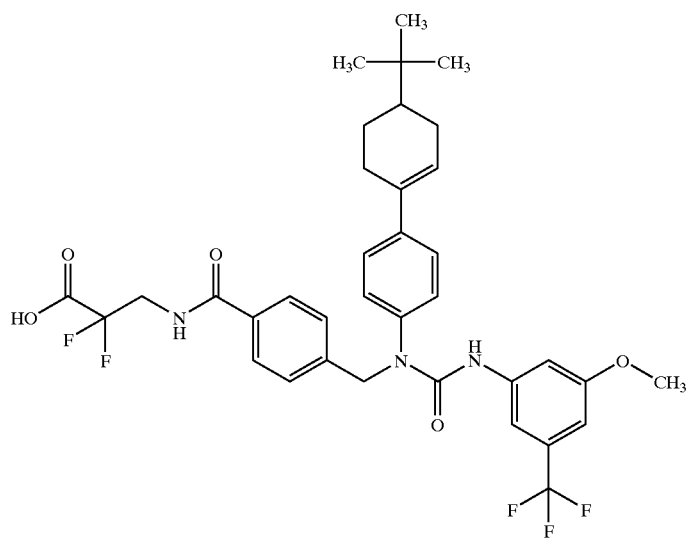

-continued
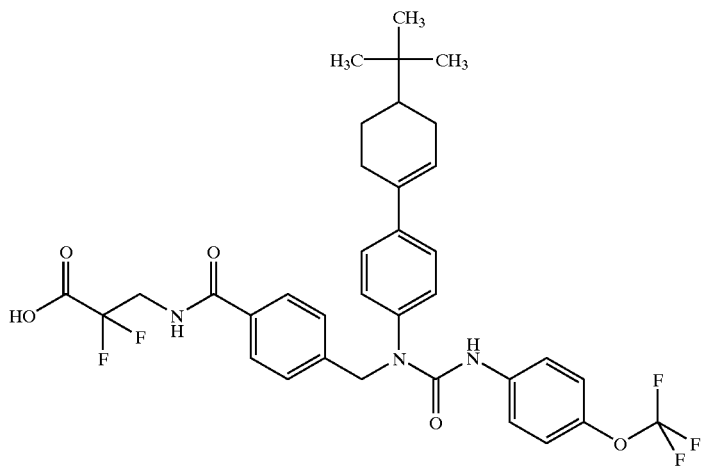
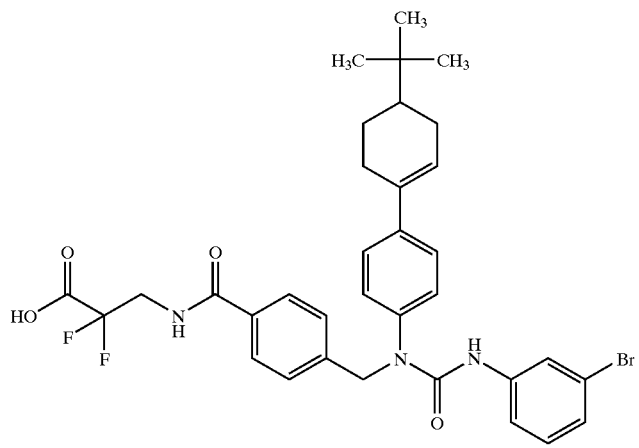
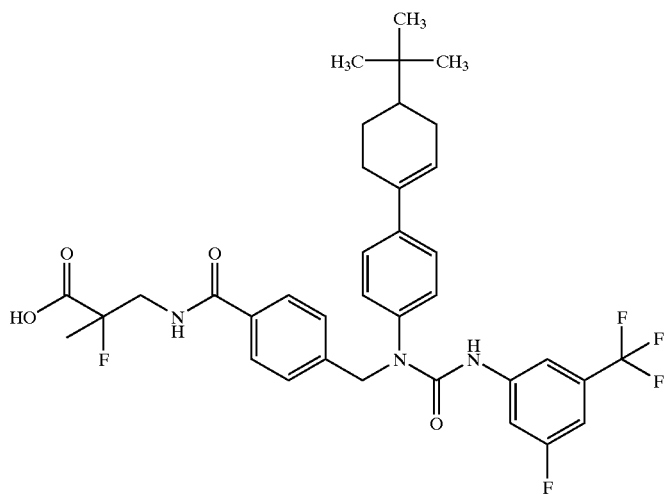

-continued
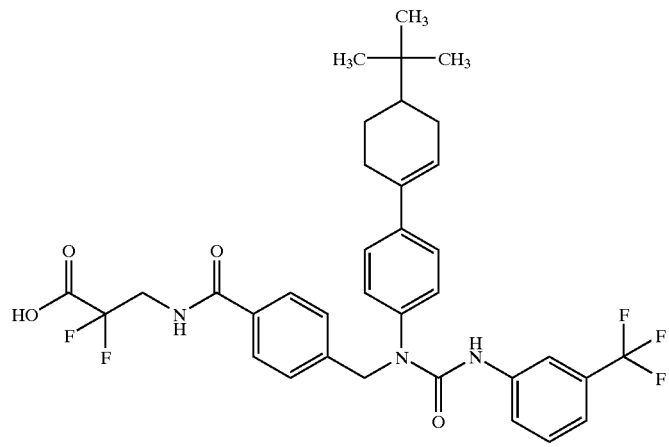
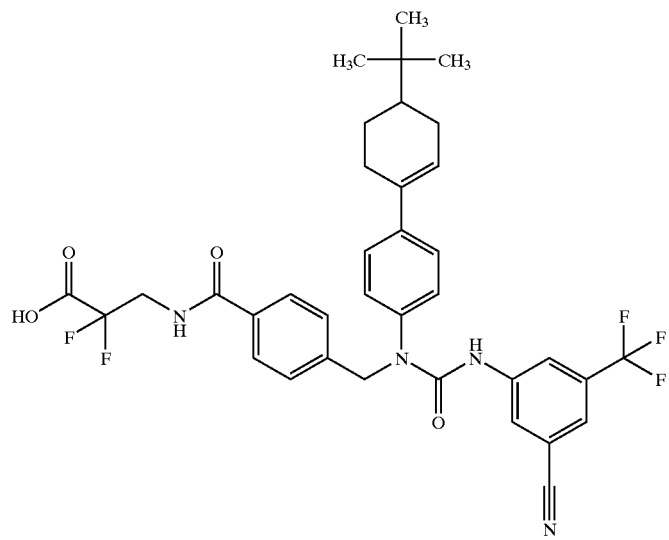
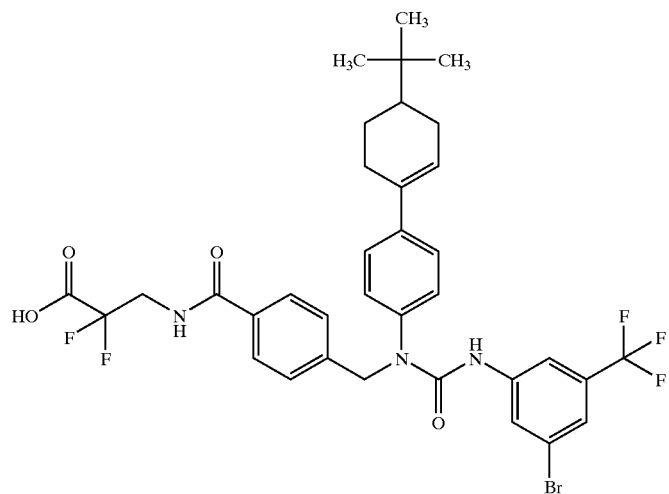

-continued
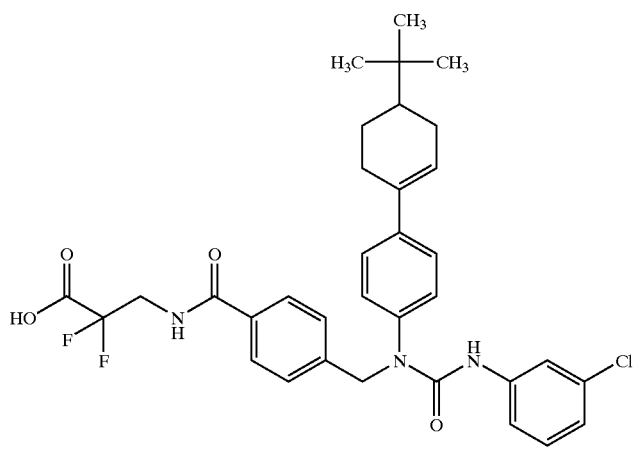
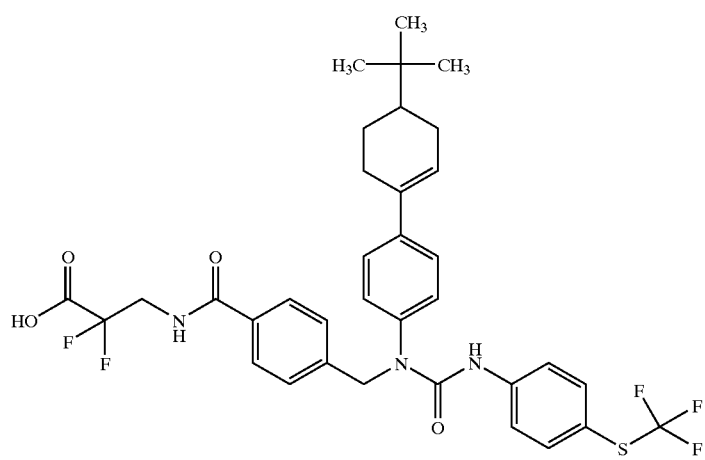
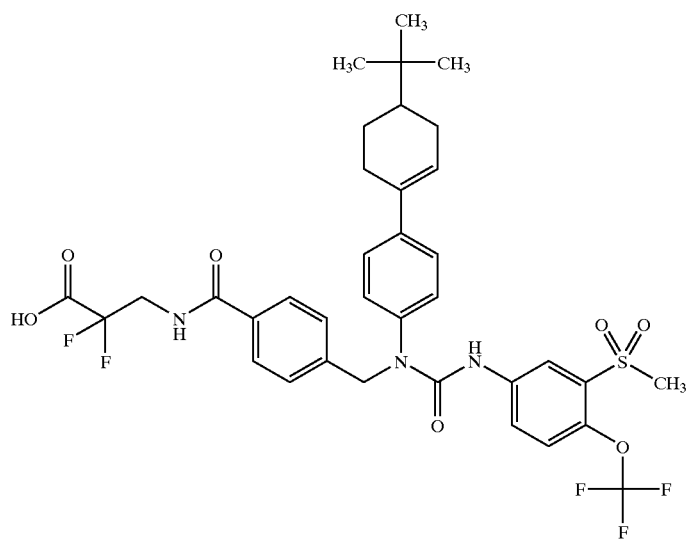

-continued
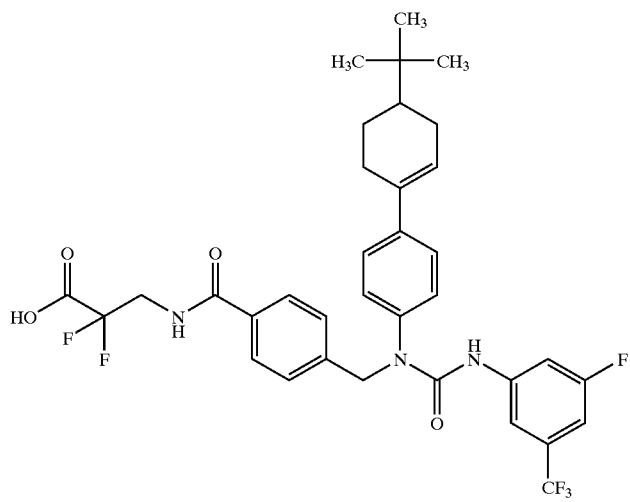
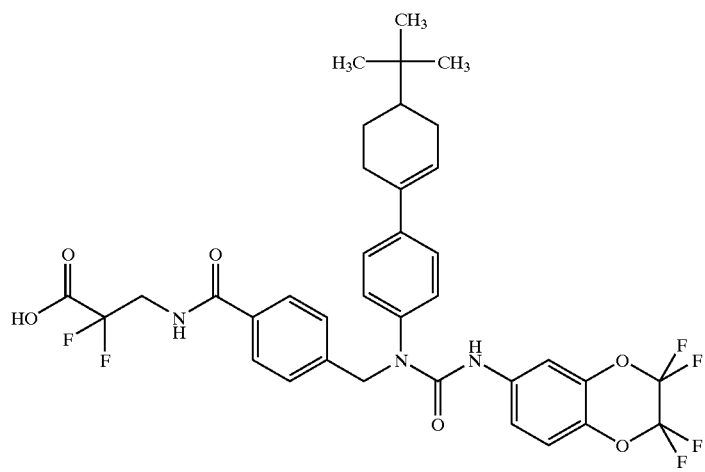
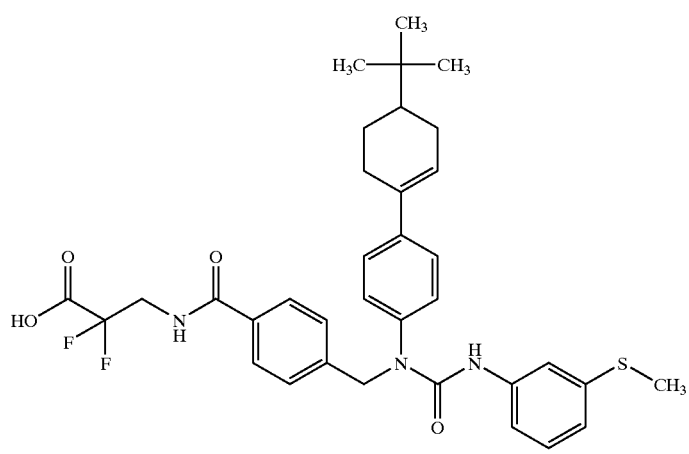

-continued
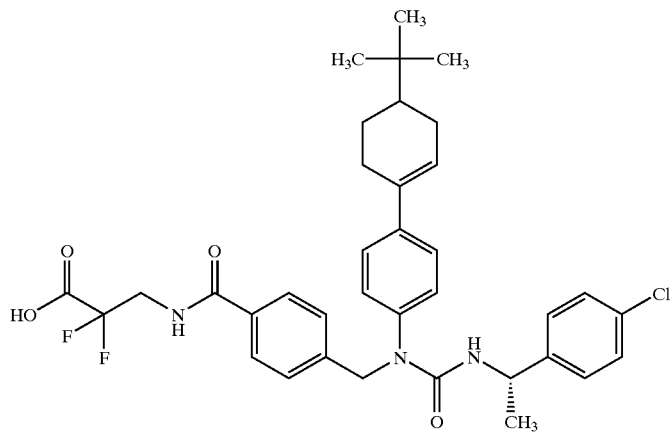
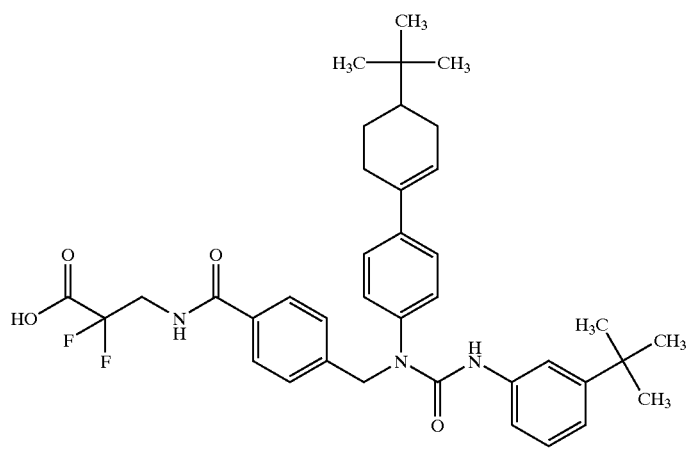
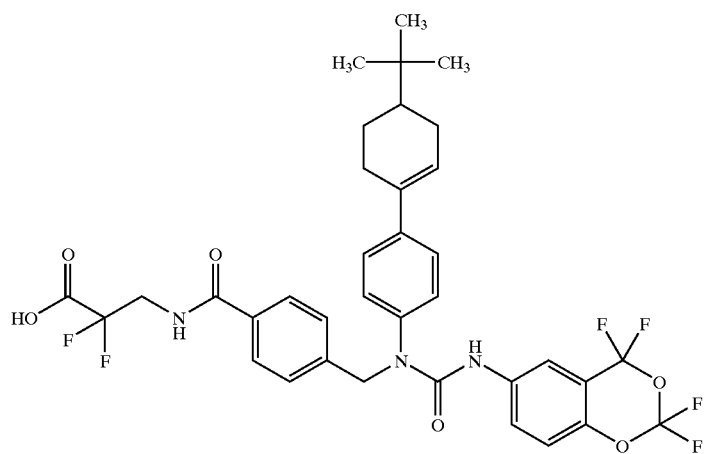

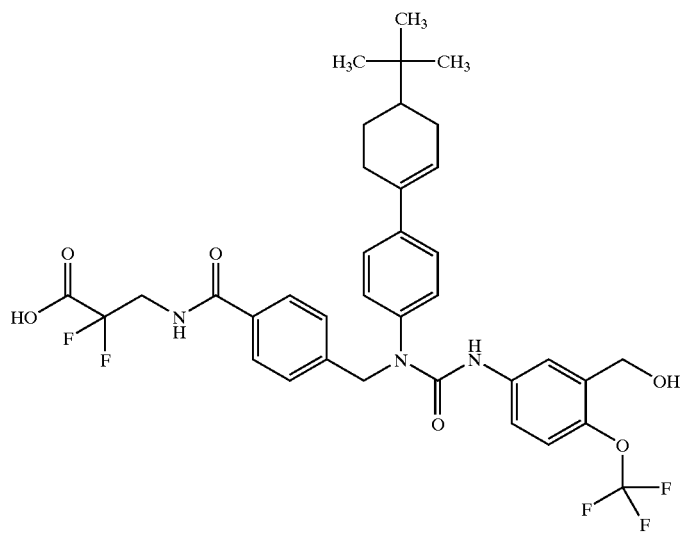
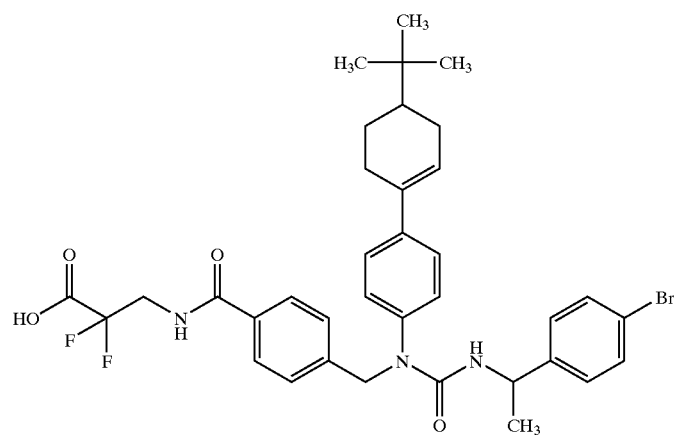
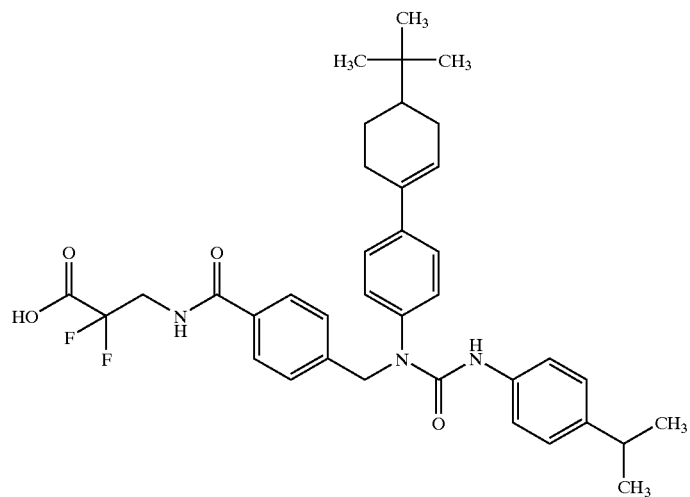

-continued
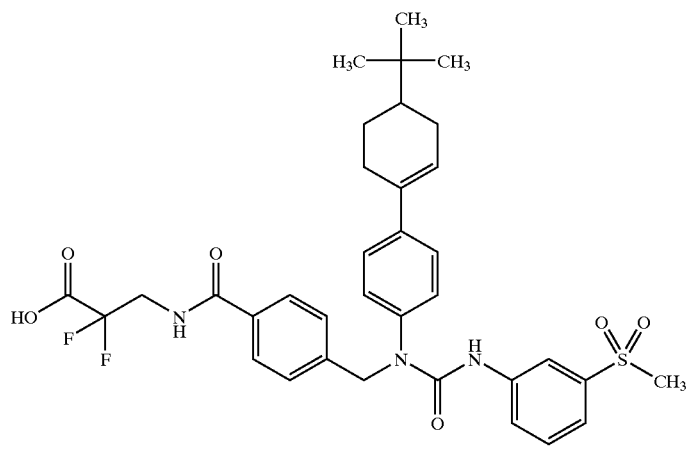
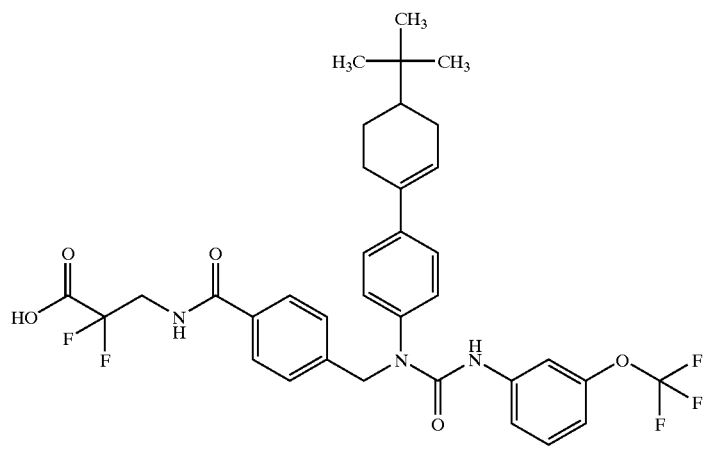
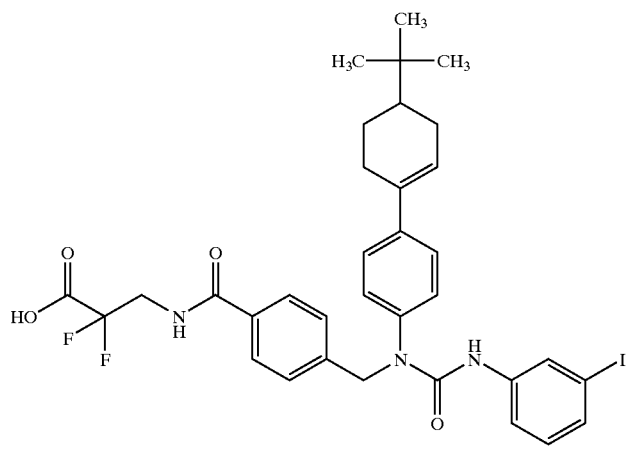

-continued
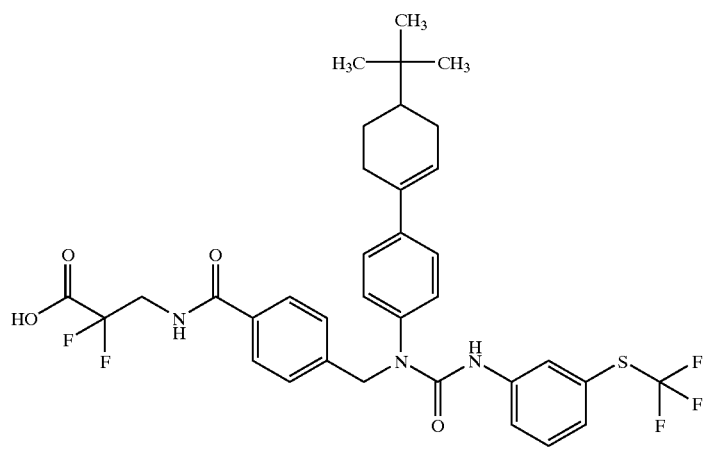
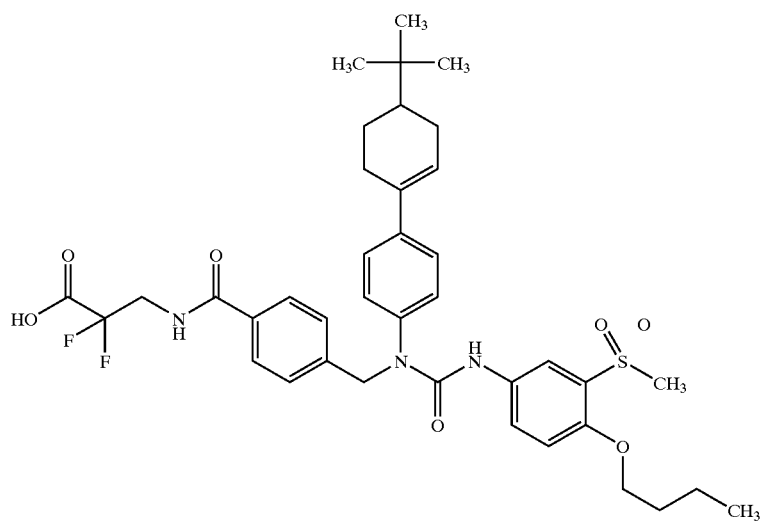
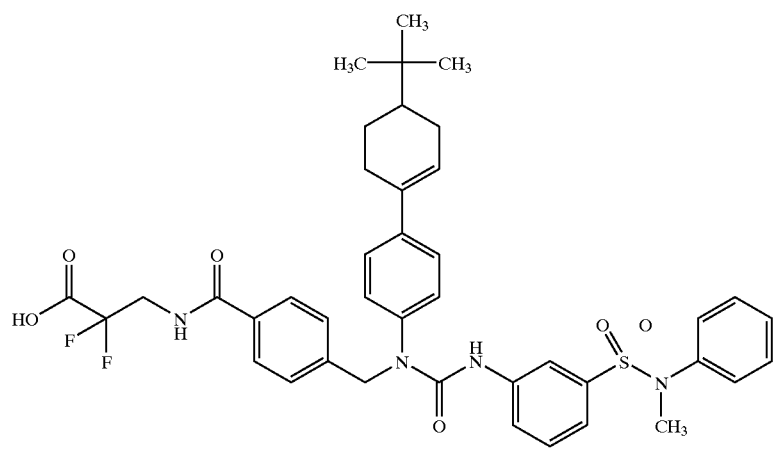

-continued

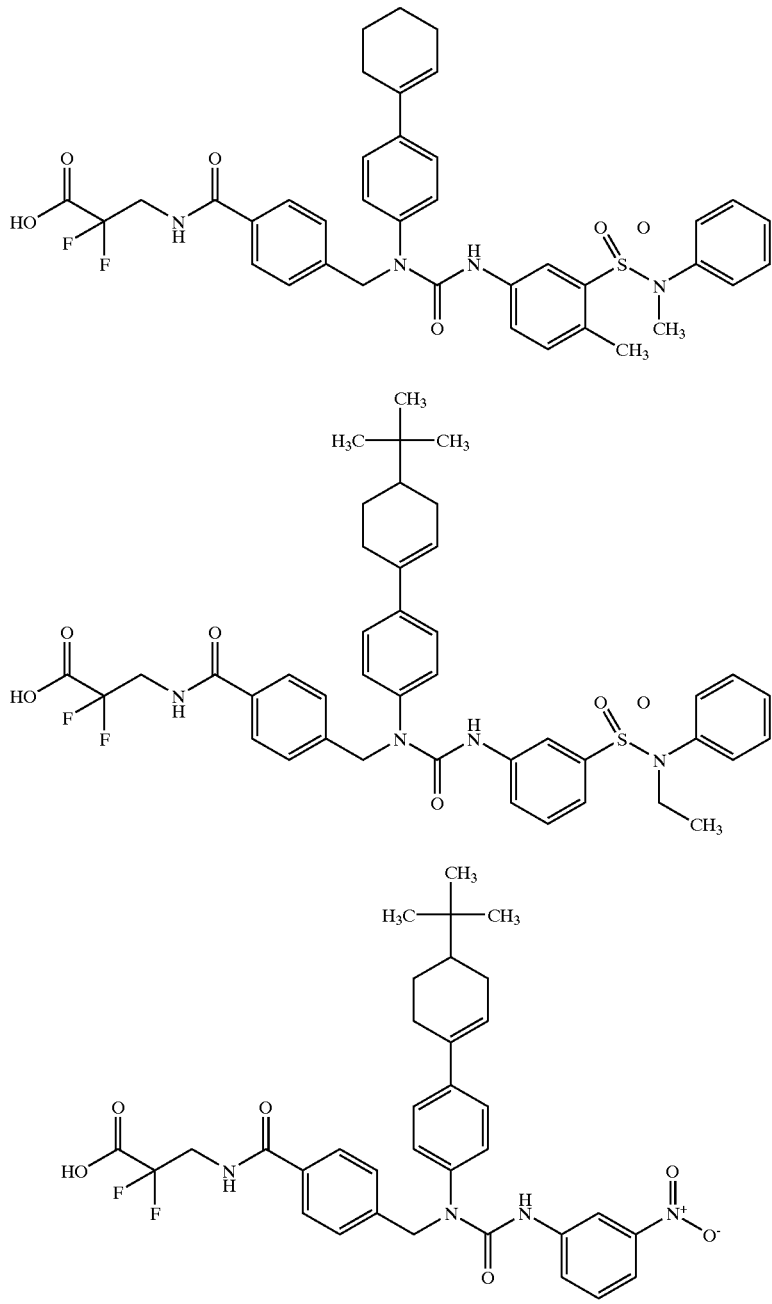

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding is assayed using cloned human receptor (Lok et al., Gene 140, 203–209 (1994)). The receptor inserted in the pLJ6' expression vector using EcoRI/SSt1 restriction sites (Lok et al.) is expressed in a baby hamster kidney cell line (A3 BHK 570–25). Clones are selected in the presence of 0.5 mg/ml G-418 and are shown to be stable for more than 40 passages. The $K_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk A/S)), homogenization by two 10-s bursts using a Polytron PT 10-35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at −80° C. until use.

Glucagon is iodinated according to the chloramine T method (Hunter and Greenwood, Nature 194, 495 (1962)) and purified using anion exchange chromatography (Jørgensen et al., Hormone and Metab. Res. 4, 223–224 (1972). The specific activity is 460 μCi/μg on the day of iodination. Tracer is stored at −18° C. in aliquots and are used immediately after thawing.

Binding assays are carried out in triplicate in filter microtiter plates (MADV N65, Millipore). The buffer used in this assay is 50 mM HEPES, 5 mM EGTA, 5 mM MgCl$_2$, 0.005% tween 20, pH 7.4. Glucagon is dissolved in 0.05 M HCl, added an equal amount (w/w) of human serum albim and freeze-dried. On the day of use, it is dissolved in water and diluted in buffer to the desired concentrations.

Test compounds are dissolved and diluted in DMSO. 140 μl buffer, 25 μl glucagon or buffer, and 10 μl DMSO or test compound are added to each well. Tracer (50.000 cpm) is diluted in buffer and 25 μl are added to each well. 1–4 μg freshly thawed plasma membrane protein diluted in buffer is then added in aliquots of 25 μl to each well. Plates are incubated at 30° C. for 2 hours. Non-specific binding is determined with 10$^{-6}$ M of glucagon. Bound tracer and unbound tracer are then separated by vacuum filtration (Millipore vacuum manifold). The plates are washed with 2×100 μl buffer/well. The plates are air dried for a couple of hours, whereupon the filters are separated from the plates using a Millipore Puncher. The filters are counted in a gamma counter.

Functional Assay (I)

The functional assay is carried out in 96 well microtiter plates (tissue culture plates, Nunc). The resulting buffer concentrations in the assay are 50 mM tris/HCl, 1 mM EGTA, 1.5 mM magnesium sulphate, 1.7 mM ATP, 20 μM GTP, 2 mM IBMX, 0.02% tween-20 and 0.1% human serum albim. pH is 7.4. Glucagon and proposed antagonist are added in aliquots of 35 μl diluted in 50 mM tris/HCl, 1 mM EGTA, 1.85 mM magnesium sulphate, 0.0222% tween-20 and 0.111% human serum albim, pH 7.4. 20 μl of 50 mM tris/HCl, 1 mM EGTA, 1.5 mM magnesium sulphate, 11.8 mM ATP, 0.14 mM GTP, 14 mM IBMX and 0.1% human serum albim, pH 7.4 is added. GTP is dissolved immediately before the assay.

50 μl containing 5 μg of plasma membrane protein is added in a tris/HCl, EGTA, magnesium sulphate, human serum albumin buffer (the actual concentrations are dependent upon the concentration of protein in the stored plasma membranes).

The total assay volume is 140 μl. The plates are incubated for 2 hours at 37° C. with continuous shaking. Reaction is terminated by addition of 25 μl 0.5 N HCl. cAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{251}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0.1 mM Pefabloc), homogenised 2×10 sec using Polytron 10-35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The glucagon binding assay is carried out in opti plates (Polystyrene Microplates, Packard). 50 μl assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μl glucagon or test compound (in DMSO) are added to each well. 50 μl tracer ($^{125}$I-porcine glucagon, 50.000 cpm) and 50 μl membranes (7.5 μg) containing the human glucagon receptor are then added to the wells. Finally 50 μl WGA beads containing 1 mg beads are transferred to the well. The plates are incubated for 4 hours on a shaker and then settled for 8–48 hours. The opti plates are counted in a Topcounter. Non-specific binding is determined with 500 nM of glucagon.

The compounds according to the examples showed IC$_{50}$ values below 1000 nM when tested in the glucagon binding assay (II).

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0.1 mM Pefabloc), homogenised 2×10 sec using Polytron 10-35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The GIP binding assay is carried out in opti plates (Polystyrene Microplates, Packard). 50 μl assay buffer (25 mM HEPES, pH=7.5, 2.5 mM CaCl$_2$, 1.0 mM MgCl$_2$, 0.003% Tween-20, 0.005% bacitracin, 0.05% sodium azide)

and 5 μl GIP or test compound (in DMSO) are added to each well. 50 μl, tracer ($^{125}$I-porcine GIP, 50.000 cpm) and 50 μl membranes (20 μg) containing the human GIP receptor are then added to the wells. Finally 50 μl WGA beads containing 1 mg beads are transferred to the well. The plates are incubated for 3.5 hours on a shaker and then settled for 8–48 hours. The opti plates are counted in a Topcounter. Non-specific binding is determined with 500 nM of GIP.

The compounds according to the examples show a higher affinity for the glucagon receptor compared to the GIP receptor.

What is claimed is:

1. A compound of the general formula (I):

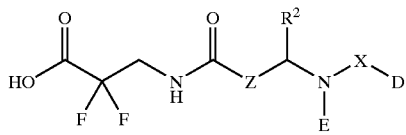
(I)

wherein $R^2$ is hydrogen or $C_{1-6}$-alkyl,

Z is arylene or a divalent radical derived from a 5 or 6 membered heteroaromatic ring containing 1 or 2 heteroatoms selected from nitrogen, oxygen and sulfur, which may optionally be substituted with one or two groups $R^7$ and $R^8$ selected from halogen, —CN, —CF$_3$, —OCF$_3$, —NO$_2$, —OR$^9$, —NR$^9$R$^{10}$ and $C_{1-6}$-alkyl, wherein $R^9$ and $R^{10}$ independently are hydrogen or $C_{1-6}$-alkyl, X is

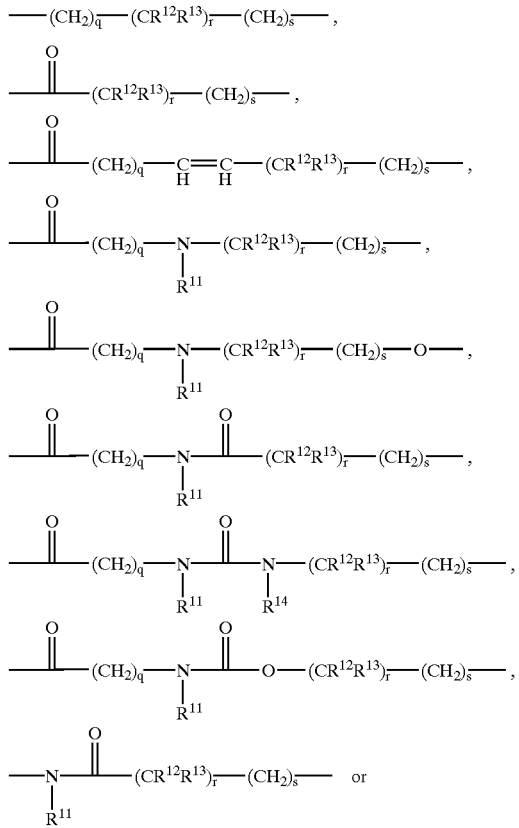

wherein r is 0 or 1, q and s independently are 0, 1, 2 or 3, $R^{11}$, $R^{12}$, $R^{13}$ and $R^{14}$ independently are hydrogen or $C_{1-6}$-alkyl, D is

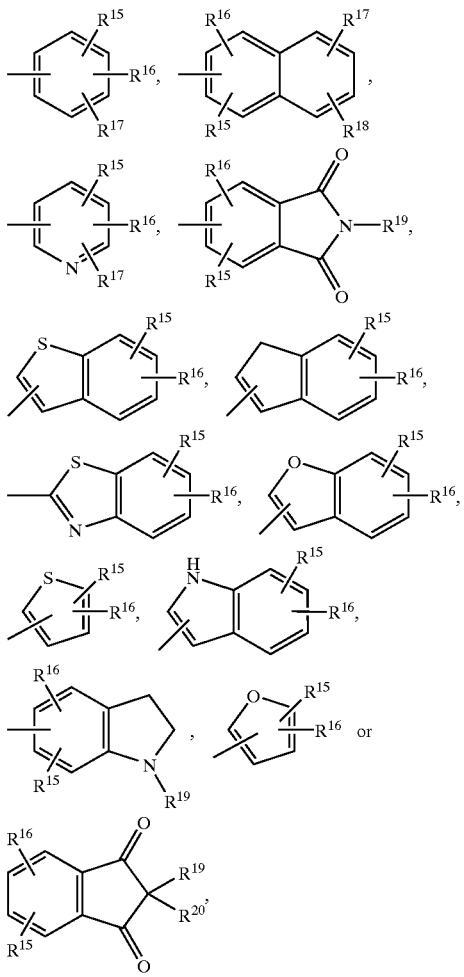

wherein $R^{15}$, $R^{16}$, $R^{17}$ and $R^{18}$ independently are
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —S(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$, $C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{21}$, —NR$^{21}$R$^{22}$ and $C_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$alkynyl, of which the cyclic moieties optionally may be substituted with one or more substituents selected from halogen, —CN, —CF$_3$, —OCF$_3$, —NO$_2$, —OR$^{21}$, —NR$^{21}$R$^{22}$ and C$_{1-6}$-alkyl, wherein R$^{21}$ and R$^{22}$ independently are hydrogen, C$_{1-6}$-alkyl or aryl, or R$^{21}$ and R$^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{15}$ to R$^{18}$ when placed in adjacent positions together may form a bridge —(CR$^{23}$R$^{24}$)$_a$—O—(CR$^{25}$R$^{26}$)$_c$—O—, wherein a is 0, 1 or 2, c is 1 or 2, R$^{23}$, R$^{24}$, R$^{25}$ and R$^{26}$ independently are hydrogen, C$_{1-6}$-alkyl or fluorine, R$^{19}$ and R$^{20}$ independently are hydrogen, C$_{1-6}$-alkyl, C$_{3-8}$cycloalkyl or C$_{3-8}$cycloalkyl-C$_{1-6}$-alkyl, E is

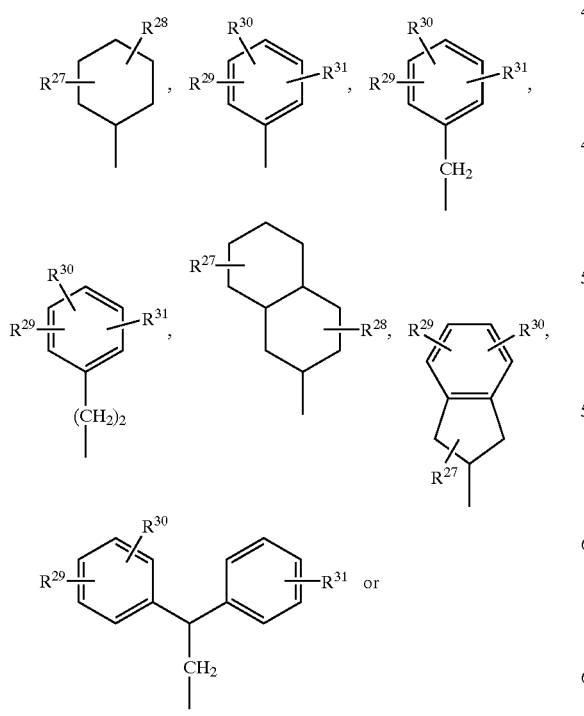

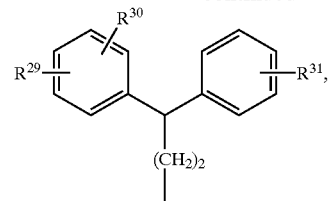

wherein

R$^{27}$ and R$^{28}$ independently are hydrogen, halogen, —CN, —CF$_3$, —OCF$_3$, —OR$^{32}$, —NR$^{32}$R$^{33}$, C$_{1-6}$-alkyl, C$_{3-8}$-cycloalkyl, C$_{4-8}$-cycloalkenyl or aryl, wherein the cyclic moieties optionally may be substituted with one or more substituents selected from halogen, —CN, —CF$_3$, —OCF$_3$, —NO$_2$, —OR$^{32}$, —NR$^{32}$R$^{33}$ and C$_{1-6}$-alkyl, wherein R$^{32}$ and R$^{33}$ independently are hydrogen or C$_{1-6}$-alkyl, or R$^{32}$ and R$^{33}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, R$^{29}$, R$^{30}$ and R$^{31}$ independently are hydrogen, halogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, C$_{1-6}$-alkyl, C$_{2-6}$-alkenyl or C$_{2-6}$-alkynyl, which may optionally be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl, heterocyclyl-C$_{2-6}$-alkynyl, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the cyclic moieties optionally may be substituted with one or more substituents selected from halogen, —CN, —CF$_3$, —OCF$_3$, —NO$_2$, —OR$^{34}$, —NR$^{34}$R$^{35}$ and C$_{1-6}$-alkyl, wherein R$^{34}$ and R$^{35}$ independently are hydrogen, C$_{1-6}$-alkyl or aryl, or R$^{34}$ and R$^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{29}$, R$^{30}$ and R$^{31}$ when attached to the same ring carbon atom or different ring carbon atoms together may form a radical —O—(CH$_2$)$_f$—CR$^{36}$R$^{37}$—(CH$_2$)$_f$—O—, —(CH$_2$)$_f$—CR$^{36}$R$^{37}$—(CH$_2$)$_f$— or —S—(CH$_2$)$_f$—CR$^{36}$R$^{37}$—(CH$_2$)$_f$—S—, wherein
t and l independently are 0, 1, 2, 3, 4 or 5,
$R^{36}$ and $R^{37}$ independently are hydrogen or $C_{1-6}$-alkyl,
as well as any optical or geometric isomer or tautomeric form thereof including mixtures of these or a pharmaceutically acceptable salt thereof.

2. A compound according to claim 1, wherein $R^2$ is hydrogen.

3. A compound according to claim 1, wherein Z is

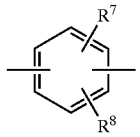

wherein $R^7$ and $R^8$ are selected from —CN, —CF$_3$, —OCF$_2$, —NO$_2$, —OR$^9$, —NR$^9$R$^{10}$, $C_{1-6}$-alkyl and hydrogen and $R^9$ and $R^{10}$ independently are hydrogen or $C_{1-6}$-alkyl.

4. A compound according to claim 3, wherein Z is

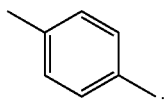

5. A compound according to claim 1, wherein X is

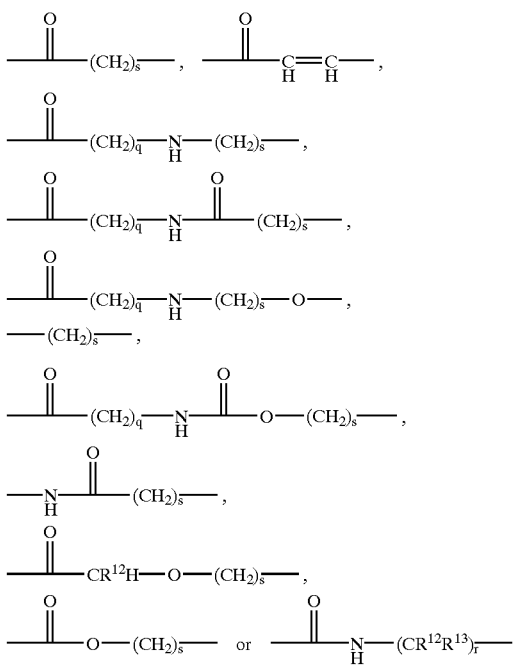

wherein q is 0 or 1, r is 0 or 1, s is 0, 1 or 2, and $R^{12}$ and $R^{13}$ independently are hydrogen or $C_{1-6}$-alkyl.

6. A compound according to claim 5, wherein X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

7. A compound according to claim 6, wherein X is —C(O)NH—, —C(O)NHCH$_2$—, —C(O)NHCH(CH$_3$)—, —C(O)NHCH$_2$CH$_2$—, —C(O)CH$_2$—, —CH$_2$—, —C(O)— or —NHC(O)—.

8. A compound according to claim 7, wherein X is —C(O)NH—.

9. A compound according to claim 1, wherein D is

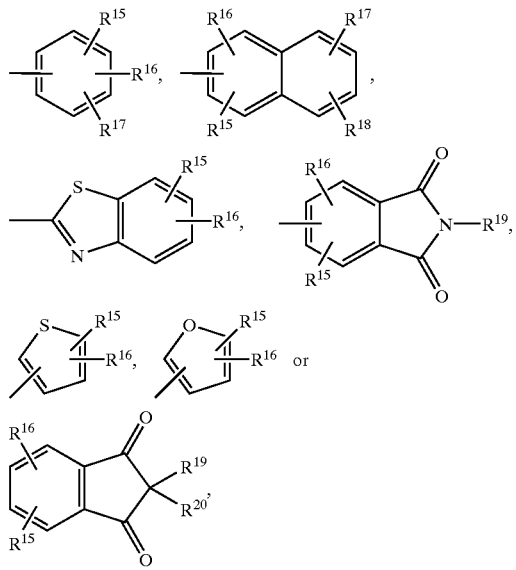

wherein $R^{15}$, $R^{16}$, $R^{17}$, $R^{18}$, $R^{19}$ and $R^{20}$ are as defined in claim 1.

10. A compound according to claim 9, wherein D is

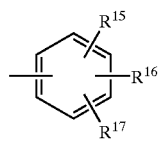

wherein $R^{15}$, $R^{16}$ and $R^{17}$ are as defined in claim 1.

11. A compound according to claim 9, wherein $R^{15}$, $R^{16}$ and $R^{17}$ independently are hydrogen, halogen, —CN, —NO$^2$, —CF$_3$, —OCF$_3$, —SCF$_3$, $C_{1-6}$-alkyl, $C_{1-6}$-alkoxy, —S—$C_{1-6}$-alkyl, —C(O)OR$^{21}$, —C(O)R$^{21}$, —CH$_2$OR$^{21}$, —C(O)NR$^{21}$R$^{22}$, —S(O)$_2$R$^{21}$, —S(O)$_2$CF$_3$, —S(O)$_2$NR$^{21}$R$^{22}$, $C_{3-8}$-cycloalkyl or aryl, or two of the groups $R^{15}$, $R^{16}$ and $R^{17}$ when placed in adjacent positions together form a bridge —(CR$^{23}$R$^{24}$)$_a$—O—(CR$^{25}$R$^{26}$)$_c$—O—, wherein $R^{21}$ and $R^{22}$ independently are hydrogen or $C_{1-6}$-alkyl, and a, c, $R^{23}$, $R^{24}$, $R^{25}$ and $R^{26}$ are as defined in claim 1.

12. A compound according to claim 11, wherein $R^{15}$, $R^{16}$ and $R^{17}$ independently are hydrogen, halogen, —CN, —CF$_3$, —OCF$_3$ or $C_{1-6}$-alkoxy.

13. A compound according to claim 12, wherein $R^{15}$, $R^{16}$ and $R^{17}$ independently are hydrogen, halogen, —CF$_3$ or —OCF$_3$.

14. A compound according to claim 1, wherein E is

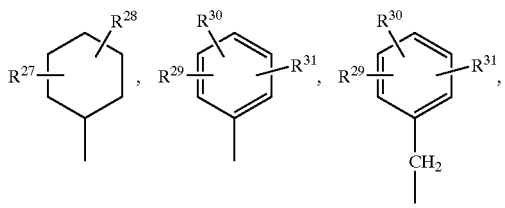

-continued

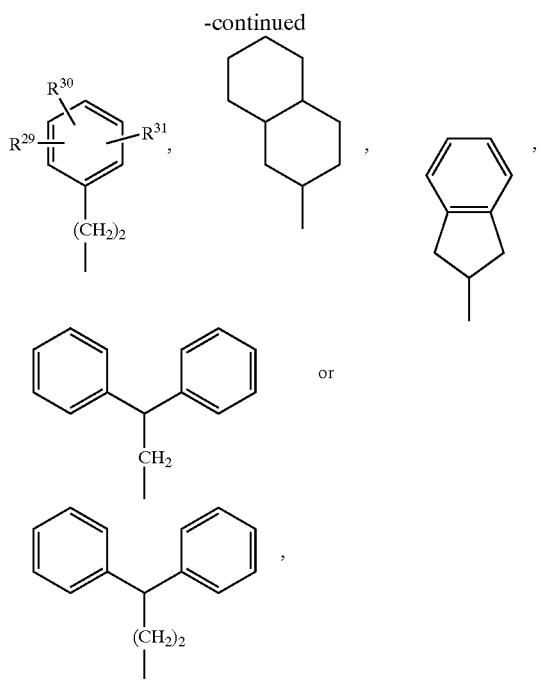

wherein $R^{27}$, $R^{28}$, $R^{29}$, $R^{30}$ and $R^{31}$ are as defined in claim 1.

15. A compound according to claim 14, wherein E is

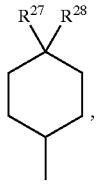

wherein $R^{27}$ and $R^{28}$ are as defined in claim 1.

16. A compound according to claim 14, wherein $R^{27}$ and $R^{28}$ independently are hydrogen, $C_{1-6}$-alkyl, $C_{3-8}$cycloalkyl, $C_{4-8}$-cycloalkenyl or phenyl, which may optionally be substituted as defined in claim 1.

17. A compound according to claim 16, wherein $R^{27}$ is hydrogen and $R^{28}$ is $C_{1-6}$-alkyl, $C_{4-8}$-cycloalkenyl or $C_{3-8}$-cycloalkyl, which may optionally be substituted as defined in claim 1.

18. A compound according to claim 14, wherein E is

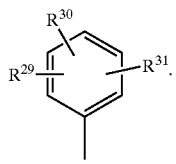

wherein $R^{29}$, $R^{30}$ and $R^{31}$ are as defined in claim 1.

19. A compound according to claim 18, wherein E is

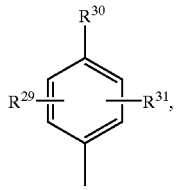

wherein $R^{29}$, $R^{30}$ and $R^{31}$ are as defined in claim 1.

20. A compound according to claim 18, wherein $R^{29}$, $R^{30}$ and $R^{31}$ independently are hydrogen, —CHF$_2$, —CF$_3$, —OCF$_3$, —OCHF$_2$, —OCH$_2$CF$_3$, —OCF$_2$CHF$_2$, —SCF$_3$, —OR$^{34}$, —NR$^{34}$R$^{35}$, —SR$^{34}$, —S(O)R$^{34}$, —S(O)$_2$R$^{34}$, —C(O)NR$^{34}$R$^{35}$, —OC(O)NR$^{34}$R$^{35}$, —NR$^{34}$C(O)R$^{35}$, —OCH$_2$C(O)NR$^{34}$R$^{35}$, —C(O)R$^{34}$ or —C(O)OR$^{34}$, $C_{1-6}$-alkyl, $C_{2-6}$-alkenyl or $C_{2-6}$-alkynyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, $C_{3-8}$-cycloalkyl or $C_{4-8}$-cycloalkenyl,
which may optionally be substituted with one or more substituents selected from halogen, —CN, —CF$_3$, —OCF$_3$, —NO$_2$, —OR$^{34}$, —NR$^{34}$R$^{35}$ and $C_{1-6}$-alkyl, wherein $R^{34}$ and $R^{35}$ independently are hydrogen, $C_{1-6}$-alkyl or aryl, or $R^{34}$ and $R^{35}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds.

21. A compound according to claim 20, wherein $R^{29}$, $R^{30}$ and $R^{31}$ independently are hydrogen, $C_{1-6}$alkoxy, —CF$_3$, —OCF$_3$ or —NR$^{34}$R$^{35}$, wherein $R^{34}$ and $R^{35}$ are as defined in claim 1, or $C_{1-6}$-alkyl, $C_{3-8}$-cycloalkyl or $C_{4-8}$-cycloalkenyl, which are optionally substituted as defined in claim 1.

22. A compound according to claim 21, wherein $R^{29}$, $R^{30}$ and $R^{31}$ independently are hydrogen or $C_{1-6}$alkyl, $C_{3-8}$-cycloalkyl or $C_{4-8}$-cycloalkenyl, which are optionally substituted as defined in claim 1.

23. A compound according to claim 22, wherein $R^{29}$, $R^{30}$ and $R^{31}$ independently are hydrogen, $C_{1-6}$-alkyl, $C_{3-8}$-cycloalkyl or $C_{4-8}$-cycloalkenyl, wherein $C_{3-8}$-cycloalkyl or $C_{4-8}$-cycloalkenyl are optionally substituted with $C_{1-6}$-alkyl.

24. A compound according to claim 23, wherein $R^{29}$ and $R^{31}$ are both hydrogen and $R^{30}$ is $C_{1-6}$-alkyl, $C_{3-8}$-cycloalkyl or $C_{4-8}$-cycloalkenyl, wherein $C_{3-8}$-cycloalkyl or $C_{4-8}$-cycloalkenyl are optionally substituted with $C_{1-6}$-alkyl.

25. A compound according to claim 24, wherein $R^{29}$ and $R^{30}$ are both hydrogen and $R^{30}$ is $C_{1-6}$-alkyl.

26. A compound according to claim 25, wherein $R^{29}$ and $R^{31}$ are both hydrogen and $R^{30}$ is $C_{4-8}$-cycloalkenyl which is optionally substituted with $C_{1-6}$-alkyl.

27. A compound according to claim 1, wherein said compound has an IC$_{50}$ value of no greater than 5 μM as determined by the Glucagon Binding Assay (I) or Glucagon Binding Assay (II).

28. A compound according to claim 27, wherein said compound has an IC$_{50}$ value of less than 1 μM, preferably of less than 500 nM and even more preferred of less than 100 nM as determined by the Glucagon Binding Assay (I) or Glucagon Binding Assay (II).

29. A compound according to claim 1, wherein said compound is an agent useful for the treatment and/or prevention of an indication selected from the group consisting of hyperglycemia, impaired glucose tolerance, Type 2 diabetes, Type 1 diabetes and obesity.

30. A pharmaceutical composition comprising at least one compound according to claim 1 together with one or more pharmaceutically acceptable carriers or excipients.

31. A pharmaceutical composition according to claim 30 in unit dosage form, said composition comprising from about 0.05 mg to about 1000 mg of the compound according to claim 1.

32. A method for the treatment of obesity, said method comprising administering to a subject in need thereof an effective amount of a compound according to claim 1.

33. A pharmaceutical composition according to claim 30 in unit dosage form, said composition comprising from about 0.1 mg to about 500 mg of the compound according to claim 1.

34. A pharmaceutical composition according to claim 30 in unit dosage form, said composition comprising from about 0.5 mg to about 200 mg of the compound according to claim 1.

35. A compound according to claim 27, wherein said compound has an $IC_{50}$ value of less than 500 nM as determined by the Glucagon Binding Assay (I) or Glucagon Binding Assay (II).

36. A compound according to claim 27, wherein said compound has an $IC_{50}$ value of less than 100 nM as determined by the Glucagon Binding Assay (I) or Glucagon Binding Assay (II).

* * * * *